United States Patent
Leamon et al.

(10) Patent No.: US 10,857,234 B2
(45) Date of Patent: Dec. 8, 2020

(54) CARBONIC ANHYDRASE IX INHIBITOR CONJUGATES AND USES THEREOF

(71) Applicant: Endocyte, Inc., West Lafayette, IN (US)

(72) Inventors: Christopher P. Leamon, West Lafayette, IN (US); Iontcho R. Vlahov, West Lafayette, IN (US); Jonathan M. Shillingford, West Lafayette, IN (US); Paul J. Kleindl, Lebanon, IN (US)

(73) Assignee: Endocyte Inc., West Lafayette, IN (US)

( * ) Notice: Subject to any disclaimer, the term of this patent is extended or adjusted under 35 U.S.C. 154(b) by 0 days.

(21) Appl. No.: 16/085,319

(22) PCT Filed: Mar. 16, 2017

(86) PCT No.: PCT/US2017/022755
§ 371 (c)(1),
(2) Date: Sep. 14, 2018

(87) PCT Pub. No.: WO2017/161144
PCT Pub. Date: Sep. 21, 2017

(65) Prior Publication Data
US 2019/0083631 A1 Mar. 21, 2019

Related U.S. Application Data

(60) Provisional application No. 62/309,271, filed on Mar. 16, 2016.

(51) Int. Cl.
| | |
|---|---|
| *A61K 47/54* | (2017.01) |
| *C07K 5/062* | (2006.01) |
| *C07K 5/093* | (2006.01) |
| *C07K 5/113* | (2006.01) |
| *C07K 5/072* | (2006.01) |
| *C07K 5/078* | (2006.01) |
| *A61K 47/65* | (2017.01) |
| *A61K 38/07* | (2006.01) |
| *A61P 35/00* | (2006.01) |

(52) U.S. Cl.
CPC ............ *A61K 47/545* (2017.08); *A61K 38/07* (2013.01); *A61K 47/54* (2017.08); *A61K 47/65* (2017.08); *A61P 35/00* (2018.01); *C07K 5/06043* (2013.01); *C07K 5/06113* (2013.01); *C07K 5/06165* (2013.01); *C07K 5/0819* (2013.01); *C07K 5/1021* (2013.01)

(58) Field of Classification Search
CPC .... A61B 3/1241; A61B 5/0071; A61K 47/54; A61K 47/65; A61K 38/07; A61K 31/433; C09B 11/08
See application file for complete search history.

(56) References Cited

U.S. PATENT DOCUMENTS

| | | |
|---|---|---|
| 7,862,798 B2 | 1/2011 | Leamon et al. |
| 8,541,604 B2 | 9/2013 | Bernardin et al. |
| 9,193,763 B2 | 11/2015 | Low et al. |
| 2009/0043099 A1 | 2/2009 | Reed et al. |
| 2010/0323973 A1 | 12/2010 | Leamon et al. |
| 2011/0321183 A1 | 12/2011 | Ploegh et al. |
| 2012/0270791 A1 | 10/2012 | Leamon et al. |
| 2012/0309045 A1 | 12/2012 | Knutson et al. |
| 2013/0143164 A1 | 6/2013 | Yabuki et al. |
| 2014/0058064 A1 | 2/2014 | Vlahov et al. |
| 2014/0073761 A1 | 3/2014 | Leamon et al. |
| 2014/0234216 A1 | 8/2014 | Schibli et al. |
| 2015/0353580 A1 | 12/2015 | Hutchison et al. |
| 2016/0016993 A1 | 1/2016 | Vlahov et al. |

FOREIGN PATENT DOCUMENTS

| | | | |
|---|---|---|---|
| EP | 2455158 | 5/2012 | |
| WO | 2009089383 A2 | 7/2009 | |
| WO | 2011/098610 | 8/2011 | |
| WO | WO-2012154885 A2 * | 11/2012 | ......... A61K 31/4439 |
| WO | 2015113760 A1 | 8/2015 | |

OTHER PUBLICATIONS

Cecchi et al (J. Med. Chem.vol. 48 pp. 4834-4841. Published 2005). (Year: 2005).*
American Association of Cancer Research News Published Mar. 2015 (Year: 2015).*
Rami et al., (Bioorganic and Medicinal Chemistry Letters vol. 18 pp. 836-841 published 2008). (Year: 2008).*
PCT International Search Report and Written Opinion for PCT/US2017/022755, completed on May 10, 2017, 9 pages.
Asakawa et al., "Radiosynthesis to three [11C]ureido-substituted benzenesulfonamides as PET probes for carbonic anhydrase IX in tumors," Biorganic & Medicinal Chem. Ltrs., 21:7017-7020 (2011).
Extended European Search Report (EESR) issued in EP Appl. No. 17767563.4 (dated Sep. 19, 2019).
Partial Supplementary European Search Report (EESR) issued in EP Appl. No. 17767541.0 (dated Nov. 5, 2019).
Krall, Nikolas et al., "A Small-Molecule Drug Conjugate for the Treatment of Carbonic Anhydrase IX Expressing Tumors," Angewandte Chemie International Edition, 53(16): Apr. 14, 2014, pp. 4231-4235.

* cited by examiner

*Primary Examiner* — Timothy P Thomas
*Assistant Examiner* — George W Kosturko
(74) *Attorney, Agent, or Firm* — Barnes & Thornburg LLP

(57) ABSTRACT

The present disclosure relates to compositions and methods of carbonic anhydrase IX inhibitors. The present disclosure also relates to targeting conjugates of carbonic anhydrase IX inhibitors as therapeutics and imaging agents. The present disclosure also relates to the use of targeting conjugates of carbonic anhydrase IX inhibitors in imaging methods and cancer therapy.

20 Claims, 9 Drawing Sheets

CARBONIC ANHYDRASE IX INHIBITOR CONJUGATES AND USES THEREOF

CROSS REFERENCE TO RELATED APPLICATION

This application is a national stage entry under 35 U.S.C. § 371(c) of PCT International Application No. PCT/US2017/022755, filed on Mar. 16, 2017, which claims the benefit under 35 U.S.C. § 119(e) of U.S. Provisional Application No. 62/309,271, filed on Mar. 16, 2016, the entire disclosures of which are incorporated herein by reference.

FIELD

The present disclosure relates to compositions and methods of carbonic anhydrase IX inhibitors. The present disclosure also relates to targeting conjugates of carbonic anhydrase IX inhibitors as therapeutics and imaging agents. The present disclosure also relates to the use of targeting conjugates of carbonic anhydrase IX inhibitors in imaging methods and cancer therapy.

BACKGROUND

The microenvironment can greatly affect the phenotype of cancer cells within a tumor. One such microenvironmental effect is hypoxia due to poorly formed vasculature present within tumors (See for example Noman M Z, Hasmim M, Messai Y, Terry S, Kieda C, Janji B, Chouaib S. Hypoxia: a key player in anti-tumor immune response. A review in the Theme: Cellular Responses to Hypoxia. *Am J Physiol Cell Physiol.* 2015, 309(1):C569-0579). Studies have shown that 1% to 1.5% of all genes are regulated by hypoxia (Harris A L. Hypoxia—a key regulatory factor in tumour growth. *Nat Rev Cancer.* 2002. 2(1):38-47). Not surprisingly then, hypoxic cancer cells can exhibit markedly different patterns of gene expression. These changes can lead to differences in sensitivity towards chemotherapeutics when in a hypoxic microenvironment which in turn can lead to increased aggressiveness and recurrence of the cancer (Yamada S, Utsunomiya T, Morine Y, Imura S, Ilcemoto T, Arakawa Y, Kanamoto M, Iwahashi S, Saito Y, Takasu C, Ishikawa D, Shimada M. Expressions of hypoxia-inducible factor-1 and epithelial cell adhesion molecule are linked with aggressive local recurrence of hepatocellular).

Due to the effects of hypoxia, efforts have been made to identify cancer specific hypoxia markers to exploit for selective imaging. One such marker, carbonic anhydrase IX (CA IX) is expressed via the activation of hypoxia-inducible factor-1 (HIF-1). CA IX is a member of a group of metalloproteins, usually containing Zinc that catalyze the reversible hydration of carbon dioxide ($CO_2 + H_2O \rightleftharpoons HCO_3^- + H^+$). CAIX is among the most active CAs for the $CO_2$ hydration reaction, and contains four domains on the basis of sequence similarity: an N-terminal proteoglycan-like (PG) domain, a CA catalytic domain, a transmembrane segment (TM), and an intracytoplasmic (IC) portion. CA IX is expressed in many cancers including lung, colorectal, gastric, pancreatic, breast, cervical, bladder, ovarian, brain, head & neck and oral cavity cancers. Additionally, due to a mutation in the VHL gene that leads to constitutive HIF-1 activation, cancers such as clear cell carcinoma of the kidney have been shown to upregulate CA IX up to 150-fold over basal levels. In normal cells, however, CA IX is only expressed in epithelial cells of the stomach and gallbladder where it appears to be catalytically inactive.

As CA IX has been touted as an excellent target for the specific delivery of imaging agents, both small molecule- and antibody-conjugates have been created to image hypoxic tumors. For example, CA IX-specific ligands have been used to image moue xenograft models of colon, renal and cervical cancers. CA IX-specific antibodies have been used to image mouse xenograft models of clear cell renal, head & neck, colon and cervical cancers in addition to human patients with clear cell renal carcinomas.

Furthermore, while much effort has been made towards CA IX-targeted imaging agents, conversely, very little research has been conducted towards targeting therapeutics to CA IX expressing cancers. The few reports of CA IX-targeted therapies involve the use of anti-CA IX antibodies either directly labeled with a therapeutic radionuclide (Muselaers C H, Oosterwijk E, Bos D L, Oyen W J, Mulders P F, Boerman O C. Optimizaing lutetium 177-anti-carbonic anhydrase IX radioimmunotherapy in an intraperitoneal clear cell renal cell carcinoma xenograft model. *Mol Imaging.* 2014. 13:1-7) or conjugated to drug containing liposomes (Wong B C, Zhang H, Qin L, Chen H, Fang C, Lu A, Yang Z. Carbonic anhydrase IX-directed immunoliposomes for targeted drug delivery to human lung cancer cells in vitro. *Drug Des Devel Ther.* 2014, 8:993-1001). To our knowledge, the efficacy of a small molecule CA IX ligand directly conjugated to a highly potent anti-cancer drug has not been reported in an in vivo mouse xenograft model.

Accordingly, there is need for further development of both CA IX targeted conjugated imaging agents and CA IX targeted therapeutics.

SUMMARY

In some embodiments, the disclosure provides a conjugate of the formula B-L-D, wherein B is a binding ligand of the formula

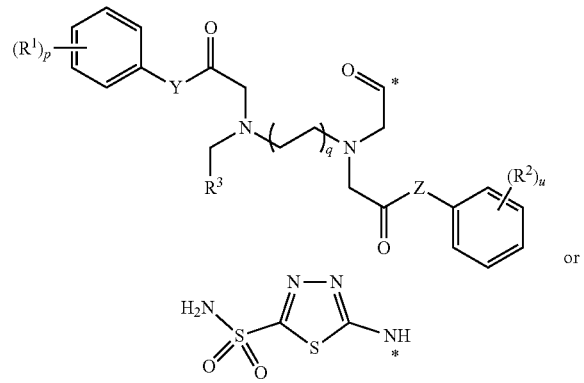

wherein wherein each $R^1$ and $R^2$ is independently selected from the group consisting of H, —$OR^4$, —$OC(O)R^4$, —$OC(O)NR^4R^5$, —$OS(O)R^4$, —$OS(O)_2R^4$, —$SR^4$, —$S(O)R^4$, —$S(O)_2R^4$, —$S(O)NR^4R^5$, —$S(O)_2NR^4R^5$, —$OS(O)NR^4R^5$, —$OS(O)_2NR^4R^5$, —$NR^4R^5$, —$NR^4C(O)R^5$, —$NR^4C(O)OR^5$, —$NR^4C(O)NR^{4'}R^{5'}$, —$NR^4S(O)R^{5'}$, —$NR^4S(O)_2R^{5'}$, —$NR^4S(O)NR^{4'}R^{5'}$, —$NR^4S(O)_2NR^{4'}R^{5'}$, —$C(O)R^4$, —$C(O)OR^4$, and —$C(O)NR^4R^5$;

$R^3$ is selected from the group consisting of H, $C_1$-$C_6$ alkyl, $C_2$-$C_6$ alkenyl, and $C_2$-$C_6$ alkynyl, —$C(O)R^6$, —$C(O)OR^7$, and —$C(O)NR^7R^{7'}$;

Y is —O—, —CH$_2$— or —NR$^8$—;
Z is —O—, —CH$_2$— or —NR$^9$—;
each R$^4$, R$^5$, R$^{4'}$, R$^{5'}$, R$^6$, R$^7$, R$^{7'}$, R$^8$ and R$^9$ is independently selected from the group consisting of H, C$_1$-C$_6$ alkyl, C$_2$-C$_6$ alkenyl, and C$_2$-C$_6$ alkynyl, or R$^6$ and R$^8$ taken together form a covalent bond from R$^3$ to Y to form a six-membered ring;
p is an integer from 1 to 4;
u is an integer from 0 to 4;
q is an integer from 1 to 3; and
* represents a covalent bond to the rest of the conjugate;
L is a linker comprising at least on releasable linker; and
D is a drug;
or a pharmaceutically acceptable salt thereof.

In other embodiments, the present disclosure provides a composition comprising a conjugate as described herein, or a pharmaceutically acceptable salt thereof, and optionally at least one pharmaceutically acceptable excipient.

In other embodiments, the present disclosure provides a method of treating cancer in a subject, comprising, a. administering to the subject an effective amount of a conjugate described herein; or a pharmaceutically acceptable salt thereof. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate as described herein for use in a method of treating cancer in a subject. In some aspects of these embodiments, the method comprises administering to the subject an amount of the conjugate effective for treating the cancer. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a use of a conjugate as described herein in the preparation of a medicament useful for treating cancer in a subject. In some aspects of these embodiments, the method comprises administering to the subject an amount of the conjugate effective for treating the cells. In some aspects of these embodiments, the cancer is selected from the group consisting of lung, colorectal, gastric, pancreatic, breast, cervical, bladder, ovarian, brain, head & neck, oral and kidney cancer.

In other embodiments, the present disclosure provides a conjugate of the formula B-L-I, wherein B is a binding ligand of the formula

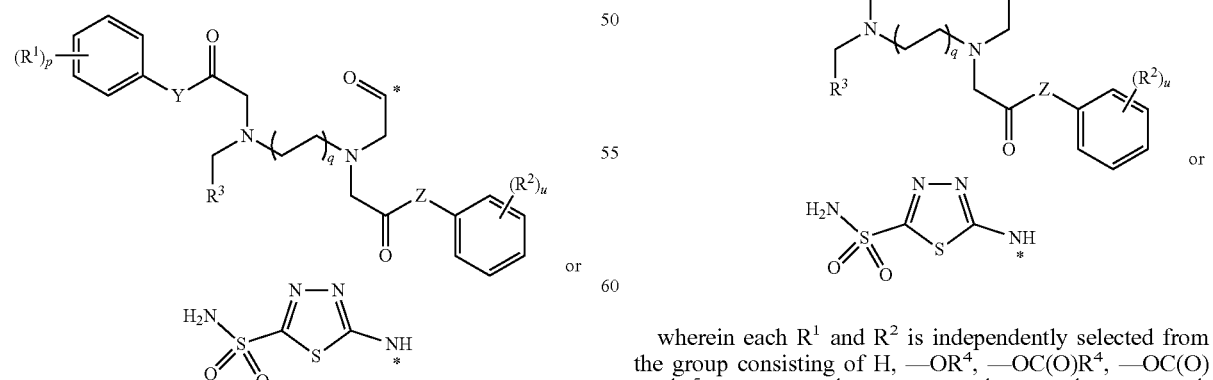

wherein each R$^1$ and R$^2$ is independently selected from the group consisting of H, —OR$^4$, —OC(O)R$^4$, —OC(O)NR$^4$R$^5$, —OS(O)R$^4$, —OS(O)$_2$R$^4$, —SR$^4$, —S(O)R$^4$, —S(O)$_2$R$^4$, —S(O)NR$^4$R$^5$, —S(O)$_2$NR$^4$R$^5$, —OS(O)NR$^4$R$^5$, —OS(O)$_2$NR$^4$R$^5$, —NR$^4$R$^5$, —NR$^4$C(O)R$^5$, —NR$^4$C(O)OR$^5$, —NR$^4$C(O)NR$^4$R$^{5'}$, —NR$^4$S(O)R$^{5'}$, —NR$^4$S(O)$_2$R$^{5'}$, —NR$^4$S(O)N$^4$R$^{5'}$, —NR$^4$S(O)$_2$NR$^4$R$^{5'}$, —C(O)R$^4$, —C(O)OR$^4$, and —C(O)NR$^4$R$^5$;
R$^3$ is selected from the group consisting of H, C$_1$-C$_6$ alkyl, C$_2$-C$_6$ alkenyl, and C$_2$-C$_6$ alkynyl, —C(O)R$^6$, —C(O)OR$^7$, and —C(O)NR$^7$R$^{7'}$;
Y is —O—, —CH$_2$— or —NR$^8$—;
Z is —O—, —CH$_2$— or —NR$^9$—;
each R$^4$, R$^5$, R$^{4'}$, R$^{5'}$, R$^6$, R$^7$, R$^{7'}$, R$^8$ and R$^9$ is independently selected from the group consisting of H, C$_1$-C$_6$ alkyl, C$_2$-C$_6$ alkenyl, and C$_2$-C$_6$ alkynyl, or R$^6$ and R$^8$ taken together form a covalent bond from R$^3$ to Y to form a six-membered ring;
p is an integer from 1 to 4;
u is an integer from 0 to 4;
q is an integer from 1 to 3; and
* represents a covalent bond to the rest of the conjugate;
L is a linker; and
I is an imaging agent;
or a pharmaceutically acceptable salt thereof.

In other embodiments, the present disclosure provides a method of imaging a population of cells in vitro, comprising a. contacting the cells with a conjugate as described herein to provide labelled cells, and b. visualizing the labelled cells with a fluorescent light source.

In other embodiments, the present disclosure provides conjugate for use in a method of imaging a population of cells in vitro. In some aspects of these embodiments, the method comprises a. contacting the cells with a conjugate according to any one of claims 52 to 55, to provide labelled cells, and b. visualizing the labelled cells with a fluorescent light source.

Embodiments of the invention are further described by the following enumerated clauses. It will be understood that any of the embodiments described herein can be used in connection with any other embodiments described herein to the extent that the embodiments do not contradict one another.

1. A conjugate of the formula B-L-D, wherein B is a binding ligand of the formula wherein each R$^1$ and R$^2$ is independently selected from the group consisting of H, —OR$^4$, —OC(O)R$^4$, —OC(O)NR$^4$R$^5$, —OS(O)R$^4$, —OS(O)$_2$R$^4$, —SR$^4$, —S(O)R$^4$, —S(O)$_2$R$^4$, —S(O)NR$^4$R$^5$, —S(O)$_2$NR$^4$R$^5$, —OS(O)NR$^4$R$^5$, —OS(O)$_2$NR$^4$R$^5$, —NR$^4$R$^5$, —NR$^4$C(O)R$^5$, —NR$^4$C(O)OR$^5$, —NR$^4$C(O)NR$^4$R$^{5'}$, —NR$^4$S(O)R$^{5'}$, —NR⁴S(O)₂R⁵', —NR⁴S(O)NR⁴'R⁵', —NR⁴S(O)₂NR⁴'R⁵', —C(O)R⁴, —C(O)OR⁴, and —C(O)NR⁴R⁵;

R³ is selected from the group consisting of H, C₁-C₆ alkyl, C₂-C₆ alkenyl, and C₂-C₆ alkynyl, —C(O)R⁶, —C(O)OR⁷, and —C(O)NR⁷R⁷';

Y is —O—, —CH₂— or —NR⁸—;

Z is —O—, —CH₂— or —NR⁹—;

each R⁴, R⁵, R⁴', R⁵', R⁶, R⁷, R⁷', R⁸ and R⁹ is independently selected from the group consisting of H, C₁-C₆ alkyl, C₂-C₆ alkenyl, and C₂-C₆ alkynyl, or R⁶ and R⁸ taken together form a covalent bond from R³ to Y to form a six-membered ring;

p is an integer from 1 to 4;
u is an integer from 0 to 4;
q is an integer from 1 to 3; and
* represents a covalent bond to the rest of the conjugate;
L is a linker comprising at least one releasable linker; and
D is a drug;
or a pharmaceutically acceptable salt thereof.

2. The conjugate of clause 1, or a pharmaceutically acceptable salt thereof, wherein p is 1.

3. The conjugate of clause 1 or 2, or a pharmaceutically acceptable salt thereof, wherein u is 1.

4. The conjugate of any one of the preceding clauses, or a pharmaceutically acceptable salt thereof, wherein q is 1.

5. The conjugate of any one of the preceding clauses, or a pharmaceutically acceptable salt thereof, wherein R¹ is —S(O)₂NR⁴R⁵.

6. The conjugate of any one of the preceding clauses, or a pharmaceutically acceptable salt thereof, wherein R¹ is —S(O)₂NR⁴R⁵ in the para-position of the ring to which R¹ is attached.

7. The conjugate of any one of the preceding clauses, or a pharmaceutically acceptable salt thereof, wherein R² is —S(O)₂NR⁴R⁵.

8. The conjugate of any one of the preceding clauses, or a pharmaceutically acceptable salt thereof, wherein R² is —S(O)₂NR⁴R⁵ in the para-position of the ring to which R² is attached.

9. The conjugate of any one of the preceding clauses, or a pharmaceutically acceptable salt thereof, wherein R⁴ and R⁵ are H.

10. The conjugate of any one of the preceding clauses, or a pharmaceutically acceptable salt thereof, wherein R³ is —C(O)OR⁶.

11. The conjugate of any one of the preceding clauses, or a pharmaceutically acceptable salt thereof, wherein R⁶ is H or —CH₃, or R⁶ and R⁸ taken together form a covalent bond from R³ to Y to form a six-membered ring.

12. The conjugate of any one of the preceding clauses, or a pharmaceutically acceptable salt thereof, wherein Y is —NR⁸—.

13. The conjugate of any one of the preceding clauses, or a pharmaceutically acceptable salt thereof, wherein Z is —NR⁹—.

14. The conjugate of any one of the preceding clauses, or a pharmaceutically acceptable salt thereof, wherein R⁹ is H or —CH₃.

15. The conjugate of any one of the preceding clauses, or a pharmaceutically acceptable salt thereof, wherein R⁸ is H or —CH₃, or R⁶ and R⁸ taken together form a covalent bond from R³ to Y to form a six-membered ring.

16. The conjugate of any one of the preceding clauses, or a pharmaceutically acceptable salt thereof, wherein B is of the formula

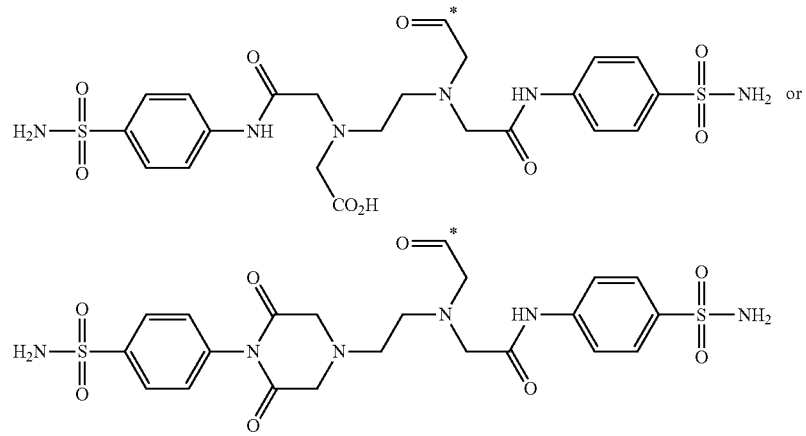

17. The conjugate of any one of the preceding clauses, or a pharmaceutically acceptable salt thereof, wherein the linker comprises at least one amino acid.

18. The conjugate of any one of the preceding clauses, or a pharmaceutically acceptable salt thereof, wherein the linker comprises at least one amino acid selected from the group consisting of Lys, Asn, Thr, Ser, Ile, Met, Pro, His, Gln, Arg, Gly, Asp, Glu, Ala, Val, Phe, Leu, Tyr, Cys, and Trp.

19. The conjugate of any one of the preceding clauses, or a pharmaceutically acceptable salt thereof, wherein the linker comprises at least two amino acids independently selected from the group consisting of Lys, Asp and Cys.

20. The conjugate of any one of the preceding clauses, or a pharmaceutically acceptable salt thereof, wherein the linker comprises an amino acid portion of the formula Asp-Asp.

21. The conjugate of any one of the preceding clauses, or a pharmaceutically acceptable salt thereof, wherein the linker comprises an amino acid portion of the formula Asp-Asp-Asp.

22. The conjugate of any one of clauses 1 to 19, or a pharmaceutically acceptable salt thereof, wherein the linker comprises an amino acid portion of the formula Lys-Asp-Lys-Asp-Lys.

23. The conjugate of any one of the preceding clauses, or a pharmaceutically acceptable salt thereof, wherein the at least one releasable linker is selected from the group consisting of

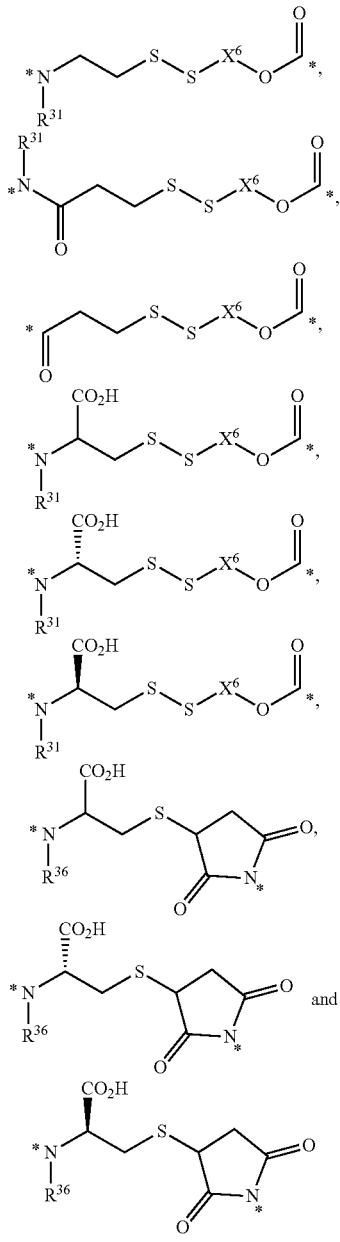

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)_{NR}^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{36}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{37}$, —$OC(O)R^{37}$, —$OC(O)NR^{37}R^{37'}$, —$OS(O)R^{37}$, —$OS(O)_2R^{37}$, —$SR^{37}$, —$S(O)R^{37}$, —$S(O)_2R^{37}$, —$S(O)NR^{37}R^{37'}$, —$S(O)_2NR^{37}R^{37'}$, —$OS(O)NR^{37}R^{37'}$, —$OS(O)_2NR^{37}R^{37'}$, —$NR^{37}R^{37'}$, —$NR^{37}C(O)R^{38}$, —$NR^{37}C(O)OR^{38}$, —$NR^{37}C(O)NR^{38}R^{38'}$, —$NR^{37}S(O)R^{38}$, —$NR^{37}S(O)_2R^{38}$, —$NR^{37}S(O)NR^{38}R^{38'}$, —$NR^{37}S(O)_2NR^{38}R^{38'}$, —$C(O)R^{37}$, —$C(O)OR^{37}$ or —$C(O)NR^{37}R^{37'}$;

$R^{37}$, $R^{37'}$, $R^{38}$ and $R^{38'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and each * represents a covalent bond to the rest of the conjugate.

24. The conjugate of any one of the preceding clauses, or a pharmaceutically acceptable salt thereof, wherein the at least one releasable linker is of the formula

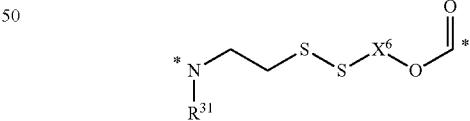

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)$ $NR^{33}R^{33'}$, $-NR^{32}S(O)R^{33}$, $-NR^{32}S(O)_2R^{33}$, $-NR^{32}S(O)$ $NR^{33}R^{33'}$, $-NR^{32}S(O)_2NR^{33}R^{33'}$, $-C(O)R^{32}$, $-C(O)OR^{32}$ or $-C(O)NR^{32}R^{32'}$;

each $X^6$ is independently $C_1-C_6$ alkyl or $C_6-C_{10}$ aryl-($C_1$-$C_6$ alkyl), wherein each hydrogen atom in $C_1-C_6$ alkyl and $C_6-C_{10}$ aryl-($C_1-C_6$ alkyl) is independently optionally substituted by halogen, $C_1-C_6$ alkyl, $C_2-C_6$ alkenyl, $C_2-C_6$ alkynyl, $C_3-C_6$ cycloalkyl, 3- to 7-membered heterocycloalkyl, $C_6-C_{10}$ aryl, 5- to 7-membered heteroaryl, $-OR^{34}$, $-OC(O)R^{34}$, $-OC(O)NR^{34}R^{34'}$, $-OS(O)R^{34}$, $-OS(O)_2R^{34}$, $-SR^{34}$, $-S(O)R^{34}$, $-S(O)_2R^{34}$, $-S(O)NR^{34}R^{34'}$, $-S(O)_2NR^{34}R^{34'}$, $-OS(O)NR^{34}R^{34'}$, $-OS(O)_2NR^{34}R^{34'}$, $-NR^{34}R^{34'}$, $-NR^{34}C(O)R^{35}$, $-NR^{34}C(O)OR^{35}$, $-NR^{34}C(O)NR^{35}R^{35'}$, $-NR^{34}S(O)R^{35}$, $-NR^{34}S(O)_2R^{35}$, $-NR^{34}S(O)NR^{35}R^{35'}$, $-NR^{34}S(O)_2NR^{35}R^{35'}$, $-C(O)R^{34}$, $-C(O)OR^{34}$ or $-C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, $C_1-C_7$ alkyl, $C_2-C_7$ alkenyl, $C_2-C_7$ alkynyl, $C_3-C_6$ cycloalkyl, 3- to 7-membered heterocycloalkyl, $C_6-C_{10}$ aryl, and 5- to 7-membered heteroaryl; and each * represents a covalent bond to the rest of the conjugate.

25. The conjugate of any one of the preceding clauses, or a pharmaceutically acceptable salt thereof, wherein the at least one releasable linker is of the formula

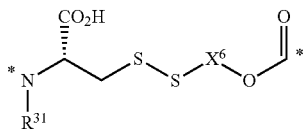

wherein each $R^{31}$ is independently selected from the group consisting of H, $C_1-C_6$ alkyl, $C_2-C_6$ alkenyl, $C_2-C_6$ alkynyl and $C_3-C_6$ cycloalkyl, wherein each hydrogen atom in $C_1-C_6$ alkyl, $C_2-C_6$ alkenyl, $C_2-C_6$ alkynyl and $C_3-C_6$ cycloalkyl is independently optionally substituted by halogen, $C_1-C_6$ alkyl, $C_2-C_6$ alkenyl, $C_2-C_6$ alkynyl, $C_3-C_6$ cycloalkyl, 3- to 7-membered heterocycloalkyl, $C_6-C_{10}$ aryl, 5- to 7-membered heteroaryl, $-OR^{32}$, $-OC(O)R^{32}$, $-OC(O)NR^{32}R^{32'}$, $-OS(O)R^{32}$, $-OS(O)_2R^{32}$, $-SR^{32}$, $-S(O)R^{32}$, $-S(O)_2R^{32}$, $-S(O)NR^{32}R^{32'}$, $-S(O)_2NR^{32}R^{32'}$, $-OS(O)NR^{32}R^{32'}$, $-OS(O)_2NR^{32}R^{32'}$, $-NR^{32}R^{32'}$, $-NR^{32}C(O)R^{33}$, $-NR^{32}C(O)OR^{33}$, $-NR^{32}C(O)NR^{33}R^{33'}$, $-NR^{32}S(O)R^{33}$, $-NR^{32}S(O)_2R^{33}$, $-NR^{32}S(O)NR^{33}R^{33'}$, $-NR^{32}S(O)_2NR^{33}R^{33'}$, $-C(O)R^{32}$, $-C(O)OR^{32}$ or $-C(O)NR^{32}R^{32'}$;

each $X^6$ is independently $C_1-C_6$ alkyl or $C_6-C_{10}$ aryl-($C_1$-$C_6$ alkyl), wherein each hydrogen atom in $C_1-C_6$ alkyl and $C_6-C_{10}$ aryl-($C_1-C_6$ alkyl) is independently optionally substituted by halogen, $C_1-C_6$ alkyl, $C_2-C_6$ alkenyl, $C_2-C_6$ alkynyl, $C_3-C_6$ cycloalkyl, 3- to 7-membered heterocycloalkyl, $C_6-C_{10}$ aryl, 5- to 7-membered heteroaryl, $-OR^{34}$, $-OC(O)R^{34}$, $-OC(O)NR^{34}R^{34'}$, $-OS(O)R^{34}$, $-OS(O)_2R^{34}$, $-SR^{34}$, $-S(O)R^{34}$, $-S(O)_2R^{34}$, $-S(O)NR^{34}R^{34'}$, $-S(O)_2NR^{34}R^{34'}$, $-OS(O)NR^{34}R^{34'}$, $-OS(O)_2NR^{34}R^{34'}$, $-NR^{34}R^{34'}$, $-NR^{34}C(O)R^{35}$, $-NR^{34}C(O)OR^{35}$, $-NR^{34}C(O)NR^{35}R^{35'}$, $-NR^{34}S(O)R^{35}$, $-NR^{34}S(O)_2R^{35}$, $-NR^{34}S(O)NR^{35}R^{35'}$, $-NR^{34}S(O)_2NR^{35}R^{35'}$, $-C(O)R^{34}$, $-C(O)OR^{34}$ or $-C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, $C_1-C_7$ alkyl, $C_2-C_7$ alkenyl, $C_2-C_7$ alkynyl, $C_3-C_6$ cycloalkyl, 3- to 7-membered heterocycloalkyl, $C_6-C_{10}$ aryl, and 5- to 7-membered heteroaryl; and each * represents a covalent bond to the rest of the conjugate.

26. The conjugate of any one of the preceding clauses, or a pharmaceutically acceptable salt thereof, wherein the at least one releasable linker is of the formula

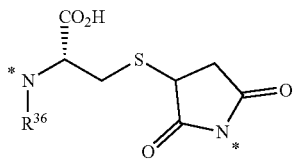

each $R^{36}$ is independently selected from the group consisting of H, $C_1-C_6$ alkyl, $C_2-C_6$ alkenyl, $C_2-C_6$ alkynyl and $C_3-C_6$ cycloalkyl, wherein each hydrogen atom in $C_1-C_6$ alkyl, $C_2-C_6$ alkenyl, $C_2-C_6$ alkynyl and $C_3-C_6$ cycloalkyl is independently optionally substituted by halogen, $C_1-C_6$ alkyl, $C_2-C_6$ alkenyl, $C_2-C_6$ alkynyl, $C_3-C_6$ cycloalkyl, 3- to 7-membered heterocycloalkyl, $C_6-C_{10}$ aryl, 5- to 7-membered heteroaryl, $-OR^{37}$, $-OC(O)R^{37}$, $-OC(O)NR^{37}R^{37'}$, $-OS(O)R^{37}$, $-OS(O)_2R^{37}$, $-SR^{37}$, $-S(O)R^{37}$, $-S(O)_2R^{37}$, $-S(O)NR^{37}R^{37'}$, $-S(O)_2NR^{37}R^{37'}$, $-OS(O)NR^{37}R^{37'}$, $-OS(O)_2NR^{37}R^{37'}$, $-NR^{37}R^{37'}$, $-NR^{37}C(O)R^{38}$, $-NR^{37}C(O)OR^{38}$, $-NR^{37}C(O)NR^{38}R^{38'}$, $-NR^{37}S(O)R^{38}$, $-NR^{37}S(O)_2R^{38}$, $-NR^{37}S(O)NR^{38}R^{38'}$, $-NR^{37}S(O)_2NR^{38}R^{38'}$, $-C(O)R^{37}$, $-C(O)OR^{37}$ or $-C(O)NR^{37}R^{37'}$;

$R^{37}$, $R^{37'}$, $R^{38}$ and $R^{38'}$ are each independently selected from the group consisting of H, $C_1-C_7$ alkyl, $C_2-C_7$ alkenyl, $C_2-C_7$ alkynyl, $C_3-C_6$ cycloalkyl, 3- to 7-membered heterocycloalkyl, $C_6-C_{10}$ aryl and 5- to 7-membered heteroaryl; and each * represents a covalent bond to the rest of the conjugate.

27. The conjugate of any one of the preceding clauses, or a pharmaceutically acceptable salt thereof, wherein the linker comprises one or more spacer linkers ($L^2$) selected from the group consisting of $C_1-C_6$ alkyl, $-(CR^{39}R^{39'})_rC(O)-$, $-(CR^{39}R^{39'})_rOC(O)-$, $-C(O)(CR^{39}R^{39'})_r-$, $-C(O)O(CR^{39}R^{39'})_r-$, $-NR^{39}R^{39'}C(O)(CR^{39}R^{39'})_r-$, $-(CH_2)_rNR^{39}-$, $-NR^{39}(CH_2)_r-$, $-NR^{39}(CH_2)_rNR^{39'}-$, $-(OCR^{39}R^{39'}CR^{39}R^{39'})_rC(O)-$, $-(OCR^{39}R^{39'}CR^{39}R^{39'}CR^{39}R^{39'})_rC(O)-$, $-OC(O)(CR^{44}R^{44'})_r-$, $-C(O)(CR^{44}R^{44'})_r-$, $-NR^{42}CR^{43}R^{43'}CR^{43}R^{43'}(OCR^{44}R^{44'}CR^{44}R^{44'})_r-$, $-CR^{43}R^{43'}CR^{43}R^{43'}(OCR^{44}R^{44'}CR^{44}R^{44'})_rNR^{42}-$, $-NR^{42}C_6-C_{10}$ $aryl(C_1-C_6$ $alkyl)OC(O)-$, $-C(O)CR^{43}R^{43'}CR^{43}R^{43'}(OCR^{44}R^{44'}CR^{44}R^{44'})_rNR^{42}-$, $-NR^{42}CR^{43}R^{43'}CR^{43}R^{43'}(OCR^{44}R^{44'}CR^{44}R^{44'})_rC(O)-$, and $-NR^{42}CR^{43}R^{43'}CR^{43}R^{43'}(CR^{44}=CR^{44'})_r-$; wherein each $R^{39}$ and $R^{39'}$ is independently selected from the group consisting of H, halogen, $C_1-C_6$ alkyl, $C_2-C_6$ alkenyl, $C_2-C_6$ alkynyl, $C_3-C_6$ cycloalkyl, 3- to 7-membered heterocycloalkyl, $C_6-C_{10}$ aryl, 5- to 7-membered heteroaryl, $-OR^{40}$, $-OC(O)R^{40}$, $-OC(O)NR^{40}R^{40'}$, $-OS(O)R^{40}$, $-OS(O)_2R^{40}$, $-SR^{40}$, $-S(O)R^{40}$, $-S(O)_2R^{40}$, $-S(O)NR^{40}R^{40'}$, $-S(O)_2NR^{40}R^{40'}$, $-OS(O)NR^{40}R^{40'}$, $-OS(O)_2NR^{40}R^{40'}$, $-NR^{40}R^{40'}$, $-NR^{40}C(O)R^{41}$, $-NR^{40}C(O)OR^{41}$, $-NR^{40}C(O)NR^{41}R^{41'}$, $-NR^{40}S(O)$ $R^{41'}$, —$NR^{40}S(O)_2R^{41}$, —$NR^{40}S(O)NR^{41}R^{41'}$, —$NR^{40}S(O)_2NR^{41}R^{41'}$, —$C(O)R^{40}$, —$C(O)OR^{40}$ and —$C(O)NR^{40}R^{40'}$;

$R^{40}$, $R^{40'}$, $R^{41}$ and $R^{41'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and r in each instance is an integer from 1 to 40;

$R^{42}$ is selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{45}$, —$OC(O)R^{45}$, —$OC(O)NR^{45}R^{45'}$, —$OS(O)R^{45}$, —$OS(O)_2R^{45}$, —$SR^{45}$, —$S(O)R^{45}$, —$S(O)_2R^{45}$, —$S(O)NR^{45}R^{45'}$, —$S(O)_2NR^{45}R^{45'}$, —$OS(O)NR^{45}R^{45'}$, —$OS(O)_2NR^{45}R^{45'}$, —$NR^{45}R^{45'}$, —$NR^{45}C(O)R^{46}$, —$NR^{45}C(O)OR^{46}$, —$NR^{45}C(O)NR^{46}R^{46'}$, —$NR^{45}S(O)R^{46}$, —$NR^{45}S(O)_2R^{46}$, —$NR^{45}S(O)NR^{46}R^{46'}$, —$NR^{45}S(O)_2NR^{46}R^{46'}$, —$C(O)R^{45}$, —$C(O)OR^{45}$ or —$C(O)NR^{45}R^{45'}$, each $R^{43}$, $R^{43'}$, $R^{44}$ and $R^{44'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{47}$, —$OC(O)R^{47}$, —$OC(O)NR^{47}R^{47'}$, —$OS(O)R^{47}$, —$OS(O)_2R^{47}$, —$SR^{47}$, —$S(O)R^{47}$, —$S(O)_2R^{47}$, —$S(O)NR^{47}R^{47'}$, —$S(O)_2NR^{47}R^{47'}$, —$OS(O)NR^{47}R^{47'}$, —$OS(O)_2NR^{47}R^{47'}$, —$NR^{47}R^{47'}$, —$NR^{47}C(O)R^{48}$, —$NR^{47}C(O)OR^{48}$, —$NR^{47}C(O)NR^{48}R^{48'}$, —$NR^{47}S(O)R^{48}$, —$NR^{47}S(O)_2R^{48}$, —$NR^{47}S(O)NR^{48}R^{48'}$, —$NR^{47}S(O)_2NR^{48}R^{48'}$, —$C(O)R^{47}$, —$C(O)OR^{47}$ or —$C(O)NR^{47}R^{47'}$;

$R^{45}$, $R^{45'}$, $R^{46}$, $R^{46'}$, $R^{47}$, $R^{47'}$, $R^{48}$ and $R^{48'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and t is in each instance an integer from 1 to 40.

28. The conjugate of any one of the preceding clauses, or a pharmaceutically acceptable salt thereof, wherein the linker comprises a hydrazine.

29. The conjugate of clause 1, or a pharmaceutically acceptable salt thereof, comprising the formula

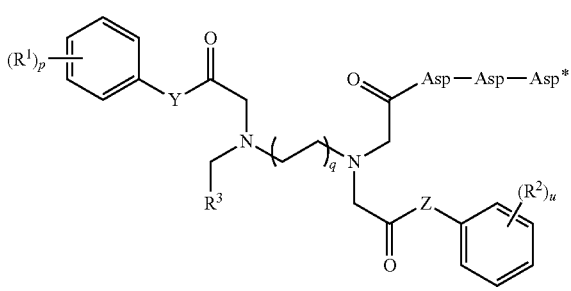

wherein * represents a covalent bond to the rest of the conjugate.

30. The conjugate of clause 1, or a pharmaceutically acceptable salt thereof, comprising the formula

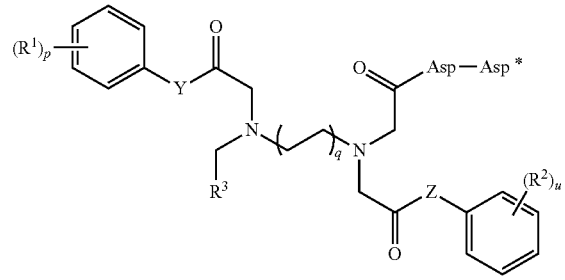

wherein * represents a covalent bond to the rest of the conjugate.

31. The conjugate of clause 1, or a pharmaceutically acceptable salt thereof, comprising the formula

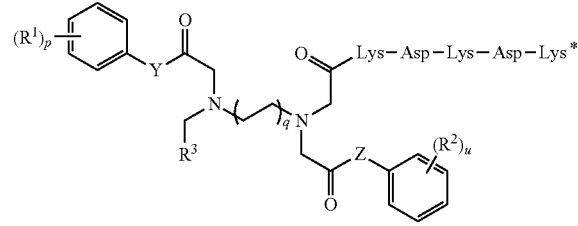

wherein * represents a covalent bond to the rest of the conjugate.

32. The conjugate of clause 1, or a pharmaceutically acceptable salt thereof, comprising the formula

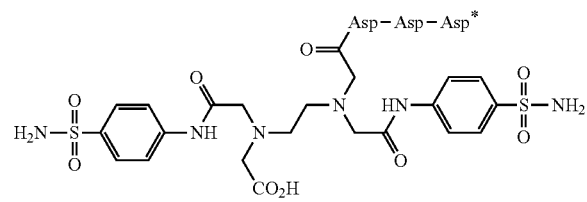

wherein * represents a covalent bond to the rest of the conjugate.

33. The conjugate of clause 1, or a pharmaceutically acceptable salt thereof, comprising the formula

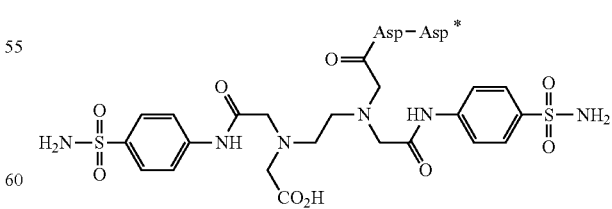

wherein * represents a covalent bond to the rest of the conjugate.

34. The conjugate of clause 1, or a pharmaceutically acceptable salt thereof, comprising the formula

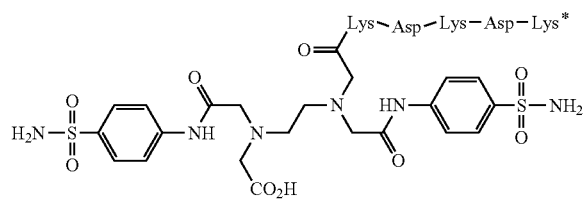

wherein * represents a covalent bond to the rest of the conjugate.

35. The conjugate of clause 1, or a pharmaceutically acceptable salt thereof, comprising the formula

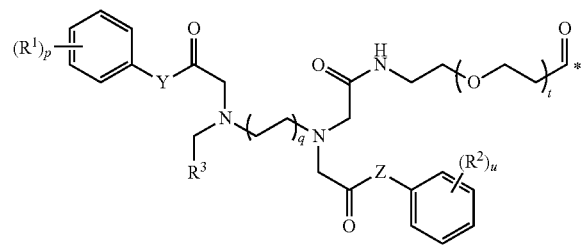

wherein t is an integer from 1 to 40, and * represents a covalent bond to the rest of the conjugate.

36. The conjugate of clause 1, or a pharmaceutically acceptable salt thereof, comprising the formula

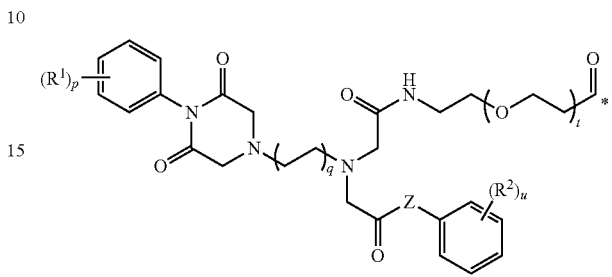

wherein t is an integer from 1 to 40, and * represents a covalent bond to the rest of the conjugate.

37. The conjugate of clause 1, or a pharmaceutically acceptable salt thereof, comprising the formula

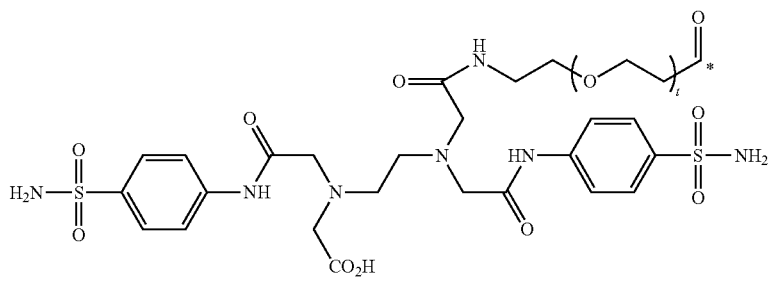

wherein t is an integer from 1 to 40, and * represents a covalent bond to the rest of the conjugate.

38. The conjugate of clause 1, or a pharmaceutically acceptable salt thereof, comprising the formula

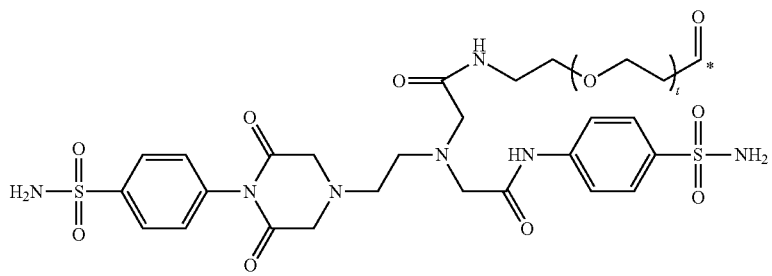

wherein t is an integer from 1 to 40, and * represents a covalent bond to the rest of the conjugate.

39. The conjugate of clause 1, or a pharmaceutically acceptable salt thereof, comprising the formula

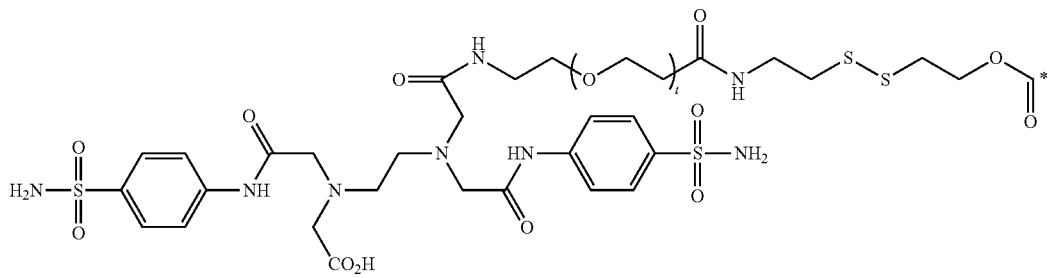

wherein t is an integer from 1 to 40, and * represents a covalent bond to the rest of the conjugate.

40. The conjugate of clause 1, or a pharmaceutically acceptable salt thereof, comprising the formula

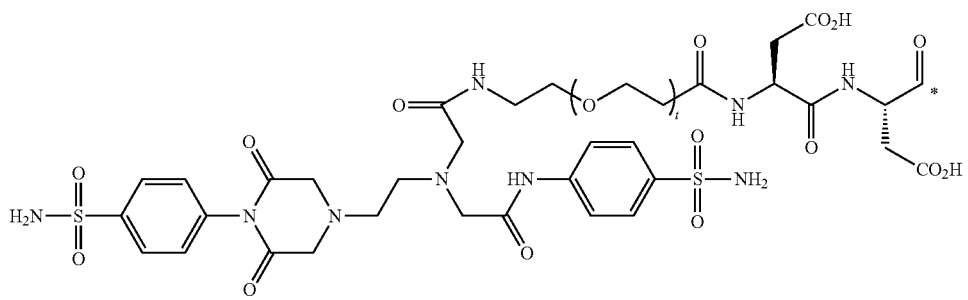

wherein t is an integer from 1 to 40, and * represents a covalent bond to the rest of the conjugate.

41. The conjugate of clause 1, or a pharmaceutically acceptable salt thereof, comprising the formula

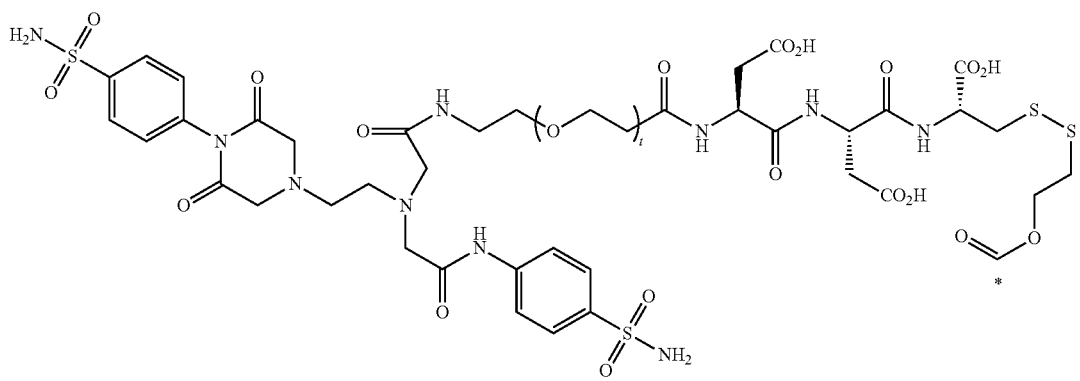

wherein t is an integer from 1 to 40, or

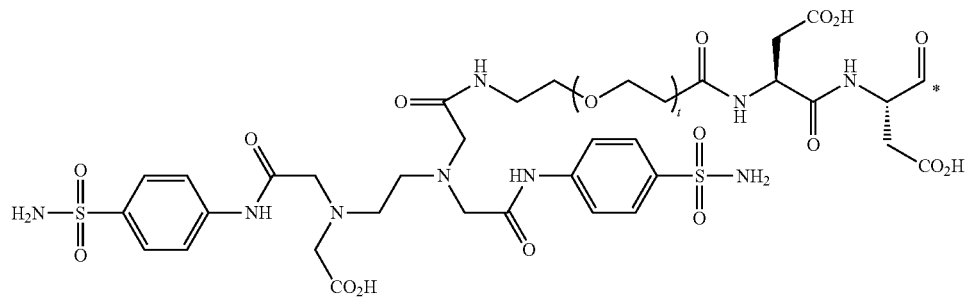

wherein t is an integer from 1 to 40, or

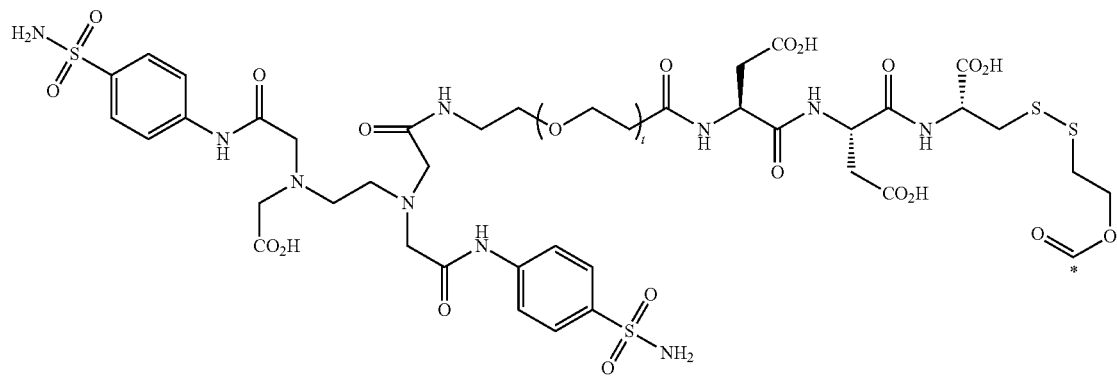

wherein t is an integer from 1 to 40, and * represents a covalent bond to the rest of the conjugate.

42. The conjugate of any one of clauses 27 to 41, or a pharmaceutically acceptable salt thereof, wherein t is 12.

43. The conjugate of any one of the preceding clauses, wherein D is selected from the group consisting of a vinca alkaloid, a cryptophycin, bortezomib, thiobortezomib, a tubulysin, aminopterin, rapamycin, paclitaxel, docetaxel, doxorubicin, daunorubicin, everolimus, α-amanatin, verucarin, didemnin B, geldanomycin, purvalanol A, ispinesib, budesonide, dasatinib, an epothilone, a maytansine, and a tyrosine kinase inhibitor.

44. The conjugate of any one of the preceding clauses, or a pharmaceutically acceptable salt thereof, wherein the drug is a tubulysin.

45. The conjugate of any one of the preceding clauses, or a pharmaceutically acceptable salt thereof, wherein the drug is a tetrapeptide of the formula

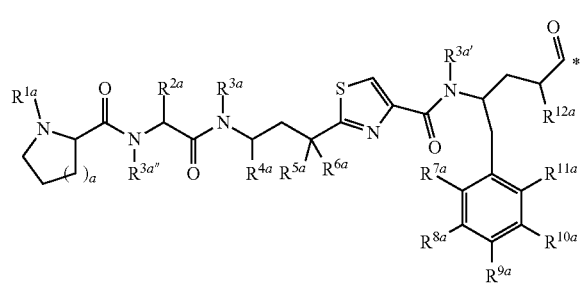

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —$OC(O)R^{13a}$, —$OC(O)NR^{13a}R^{13a'}$, —$OS(O)R^{13a}$, —$OS(O)_2R^{13a}$, —$SR^{13a}$, —$SC(O)R^{13a}$, —$S(O)R^{13a}$, —$S(O)_2R^{13a}$, —$S(O)_2OR^{13a}$, —$S(O)NR^{13a}R^{13a'}$, —$S(O)_2NR^{13a}R^{13a'}$, —$OS(O)NR^{13a}R^{13a'}$, —$OS(O)_2NR^{13a}R^{13a'}$, —$NR^{13a}R^{13a'}$, —$NR^{13a}C(O)R^{14a}$, —$NR^{13a}C(O)OR^{14a}$, —$NR^{13a}C(O)NR^{14a}R^{14a'}$, —$NR^{13a}S(O)R^{14a}$, —$NR^{13a}S(O)_2R^{14a}$, —$NR^{13a}S(O)NR^{13a}R^{14a'}$, —$NR^{13a}S(O)_2NR^{14a}R^{14a'}$, —$P(O)(OR^{13a})_2$, —$C(O)R^{13a}$, —$C(O)OR^{13a}$ or —$C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —$NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —$NR^{16a}R^{16a'}$, —$C(O)R^{16a}$, —$C(O)OR^{16a}$ or —$C(O)NR^{16a}R^{16a'}$; or $R^{3a}$ and $R^{6a}$ taken together with the carbon atom to which they are attached form a —C(O)—;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17a}$, —$SR^{17a}$, —$S(O)_2R^{17a}$, —$NR^{17a}R^{17a'}$, —$P(O)(OR^{17a})_2$, —$C(O)R^{17a}$, —$C(O)OR^{17a}$ and —$C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —$OR^{18a}$, —$SR^{18a}$, —$NR^{18a}R^{18a'}$, —$C(O)R^{18a}$, —$C(O)OR^{18a}$ or —$C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $12^{18a}$ and $12^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19a}$, —$P(O)(OR^{19a})_2$, and —$S(O)_2OR^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

46. The conjugate of any one of the preceding clauses, or a pharmaceutically acceptable salt thereof, wherein D is a tetrapeptide of the formula

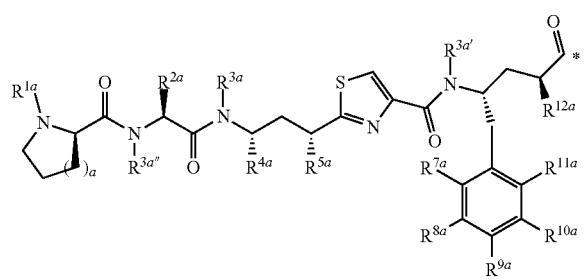

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{13a}$, —$OC(O)R^{13a}$, —$OC(O)NR^{13a}R^{13a'}$, —$OS(O)R^{13a}$, —$OS(O)_2R^{13a}$, —$SR^{13a}$, —$SC(O)R^{13a}$, —$S(O)R^{13a}$, —$S(O)_2R^{13a}$, —$S(O)_2R^{13a}$, —$S(O)NR^{13a}R^{13a'}$, —$S(O)_2NR^{13a}R^{13a'}$, —$OS(O)NR^{13a}R^{13a'}$, —$OS(O)_2NR^{13a}R^{13a'}$, —$NR^{13a}R^{13a'}$, —$NR^{13a}C(O)NR^{14a}$, —$NR^{13a}C(O)OR^{14a}$, —$NR^{13a}C(O)$ $NR^{14a}R^{14a'}$, —$NR^{13a}S(O)R^{14a}$, —$NR^{13a}S(O)_2R^{14a}$, —$NR^{13a}S(O)NR^{13a}R^{14a'}$, —$NR^{13a}S(O)_2NR^{14a}R^{14a'}$, —$P(O)(OR^{13a})_2$, —$C(O)R^{13a}$, —$C(O)OR^{13a}$ or —$C(O)NR^{13a}R^{13a'}$;

$R^{5a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ is selected from the group consisting of H, halogen, $C_1$-$C_6$ alkyl, $C_2$-$C_6$ alkenyl, $C_2$-$C_6$ alkynyl, —$OR^{15a}$, —$SR^{15a}$ and —$NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, —$OR^{16a}$, —$SR^{16a}$, —$NR^{16a}R^{16a'}$, —$C(O)R^{16a}$, —$C(O)OR^{16a}$ or —$C(O)NR^{16a}R^{16a'}$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17a}$, —$SR^{17a}$, —$S(O)_2OR^{17a}$, —$NR^{17a}R^{17a'}$, —$P(O)(OR^{17a})_2$, —$C(O)R^{17a}$, —$C(O)OR^{17a}$ and —$C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, —$OR^{18a}$, —$SR^{18a}$, —$NR^{18a}R^{18a'}$, —$C(O)R^{18a}$, —$C(O)OR^{18a}$ or —$C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, —OH, —SH, —$NH_2$ or —$CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl —$C(O)R^{19a}$, —$P(O)(OR^{19a})_2$, and —$S(O)_2OR^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

47. The conjugate of any one of the preceding clauses, or a pharmaceutically acceptable salt thereof, wherein D is a tetrapeptide of the formula

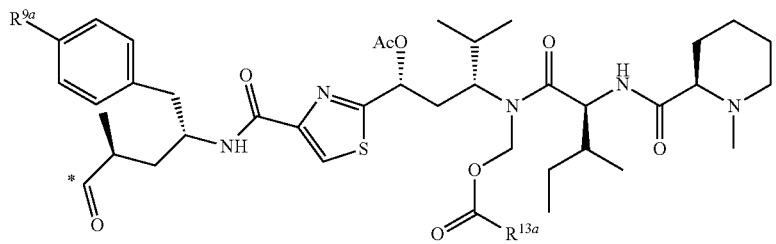

wherein $R^{9a}$ is selected from the group consisting of H, halogen, $C_1$-$C_6$ alkyl, $C_2$-$C_6$ alkenyl, $C_2$-$C_6$ alkynyl, —CN, —$NO_2$, —NCO, —$OR^{17a}$, —$SR^{17a}$, —$S(O)_2OR^{17a}$, —$NR^{17a}R^{17a=}$, —$P(O)(OR^{17a})_2$, —$C(O)R^{17a}$, —$C(O)$ $OR^{17a}$ and $-C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $-OR^{18a}$, $-SR^{18a}$, $-NR^{18a}R^{18a'}$, $-C(O)R^{18a}$, $-C(O)OR^{18a}$ or $-C(O)NR^{18a}R^{18a'}$;

each $R^{13a}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $-OH$, $-SH$, $-NH_2$ or $-CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl $-C(O)R^{19a}$, $-P(O)(OR^{19a})_2$, and $-S(O)_2OR^{19a}$, each $R^{19a}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl; and

* represents a covalent bond to the rest of the conjugate.

48. The conjugate of any one of the preceding clauses, or a pharmaceutically acceptable salt thereof, wherein the drug is a naturally occurring tubulysin.

49. The conjugate of any one of the preceding clauses, or a pharmaceutically acceptable salt thereof, wherein the drug is selected from the group consisting of tubulysin A, tubulysin B, tubulysin C, tubulysin D, tubulysin E, tubulysin F, tubulysin G, tubulysin H and tubulysin I.

50. The conjugate of any one of the preceding clauses, or a pharmaceutically acceptable salt thereof, wherein the drug is tubulysin B.

51. The conjugate of any one of the preceding clauses, or a pharmaceutically acceptable salt thereof, wherein the drug is of the formula

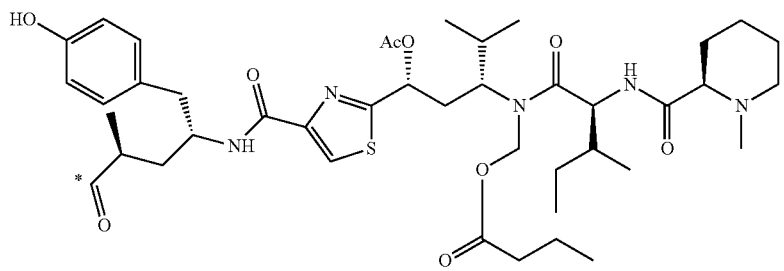 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C=O)cs1)C(C)C]

wherein * represents a covalent bond to the rest of the conjugate.

52. The conjugate of any one of the preceding clauses, or a pharmaceutically acceptable salt thereof, wherein the drug is of the formula

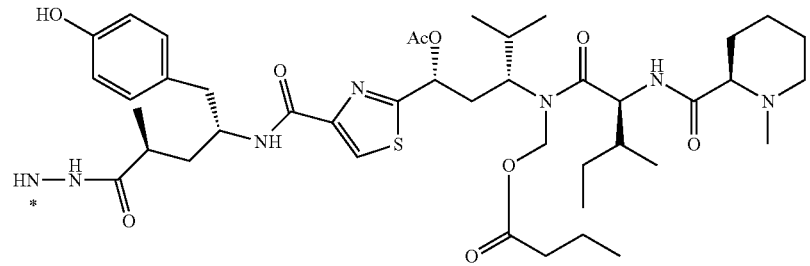 [SMILES: CCCC(=O)OCN(C(=O)[C@@H](NC(=O)[C@H]1CCCCN1C)C(C)CC)[C@H](C[C@@H](OC(C)=O)c1nc(C(=O)N[C@@H](Cc2ccc(O)cc2)C[C@H](C)C(=O)NN)cs1)C(C)C]

wherein * represents a covalent bond to the rest of the conjugate.

53. The conjugate of clause 1, selected from the group consisting of

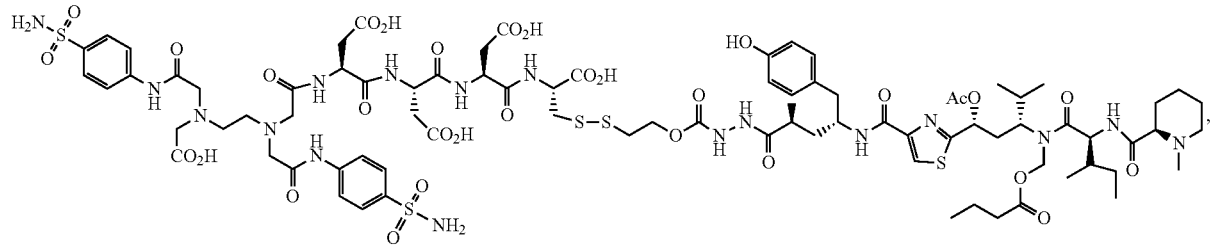

-continued
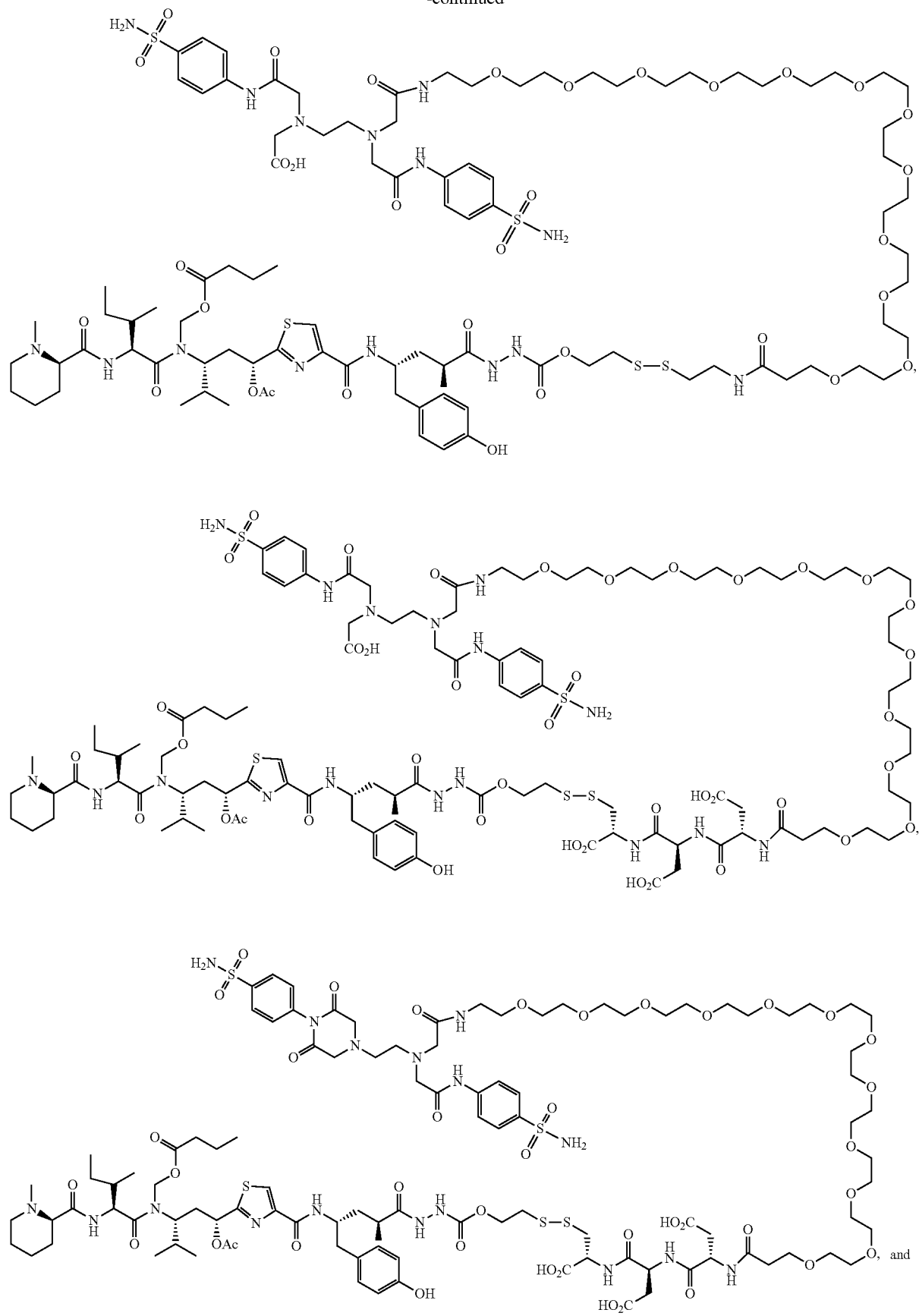

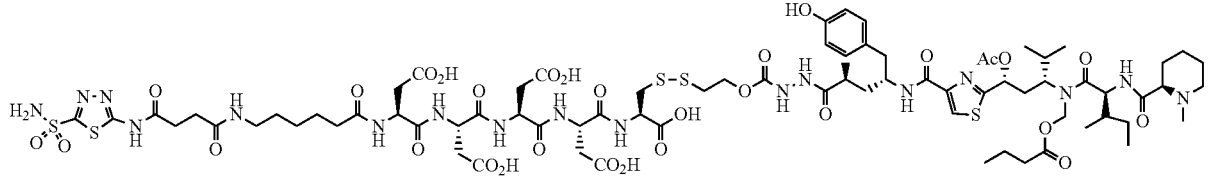

or a pharmaceutically acceptable salt thereof.

54. A pharmaceutical composition comprising a conjugate of any of the preceding clauses, or a pharmaceutically acceptable salt thereof, and optionally at least one pharmaceutically acceptable excipient.

55. A conjugate of the formula B-L-I, wherein B is a binding ligand of the formula

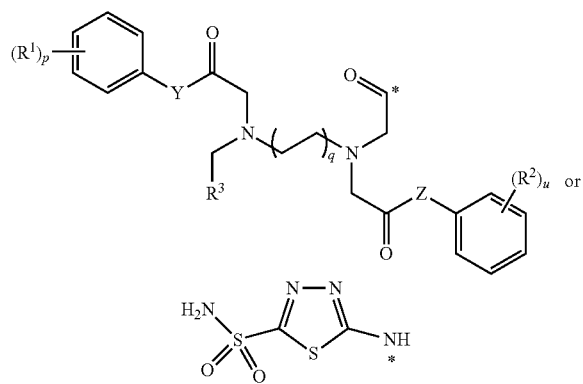

wherein each $R^1$ and $R^2$ is independently selected from the group consisting of H, —$OR^4$, —$OC(O)R^4$, —OC(O)$NR^4R^5$, —OS(O)$R^4$, —OS(O)$_2R^4$, —$SR^4$, —S(O)$R^4$, —S(O)$_2R^4$, —S(O)$NR^4R^5$, —S(O)$_2NR^4R^5$, —OS(O)$NR^4R^5$, —OS(O)$_2NR^4R^5$, —$NR^4R^5$, —$NR^4C(O)R^5$, —$NR^4C(O)OR^5$, —$NR^4C(O)NR^{4'}R^{5'}$, —$NR^4S(O)R^{5'}$, —$NR^4S(O)_2R^{5'}$, —$NR^4S(O)NR^{4'}R^{5'}$, —$NR^4S(O)_2NR^{4'}R^{5'}$, —$C(O)R^4$, —$C(O)OR^4$, and —$C(O)NR^4R^5$;

$R^3$ is selected from the group consisting of H, $C_1$-$C_6$ alkyl, $C_2$-$C_6$ alkenyl, and $C_2$-$C_6$ alkynyl, —$C(O)R^6$, —$C(O)OR^7$, and —$C(O)NR^7R^{7'}$;

Y is —O—, —$CH_2$— or —$NR^8$—;

Z is —O—, —$CH_2$— or —$NR^9$—;

each $R^4$, $R^5$, $R^{4'}$, $R^{5'}$, $R^6$, $R^7$, $R^{7'}$, $R^8$ and $R^9$ is independently selected from the group consisting of H, $C_1$-$C_6$ alkyl, $C_2$-$C_6$ alkenyl, and $C_2$-$C_6$ alkynyl, or $R^6$ and $R^8$ taken together form a covalent bond from $R^3$ to Y to form a six-membered ring;

p is an integer from 1 to 4;

u is an integer from 0 to 4;

q is an integer from 1 to 3; and

* represents a covalent bond to the rest of the conjugate;

L is a linker; and

I is an imaging agent;

or a pharmaceutically acceptable salt thereof.

56. The conjugate of clause 55, or a pharmaceutically acceptable salt thereof, wherein B is of the formula

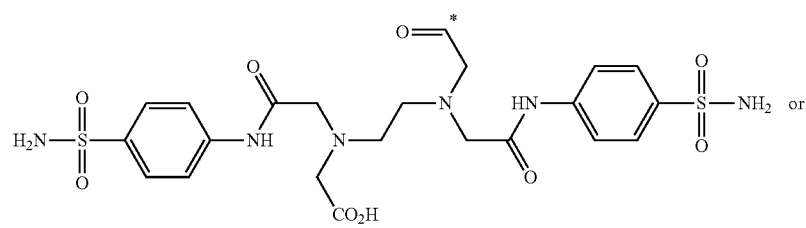

or

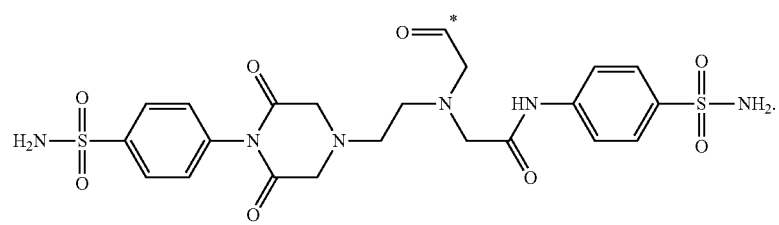

57. The conjugate of clause 55 or 56, or a pharmaceutically acceptable salt thereof, wherein I is a rhodamine dye.
58. The conjugate of any one of clause 55 to 57, selected from the group consisting of
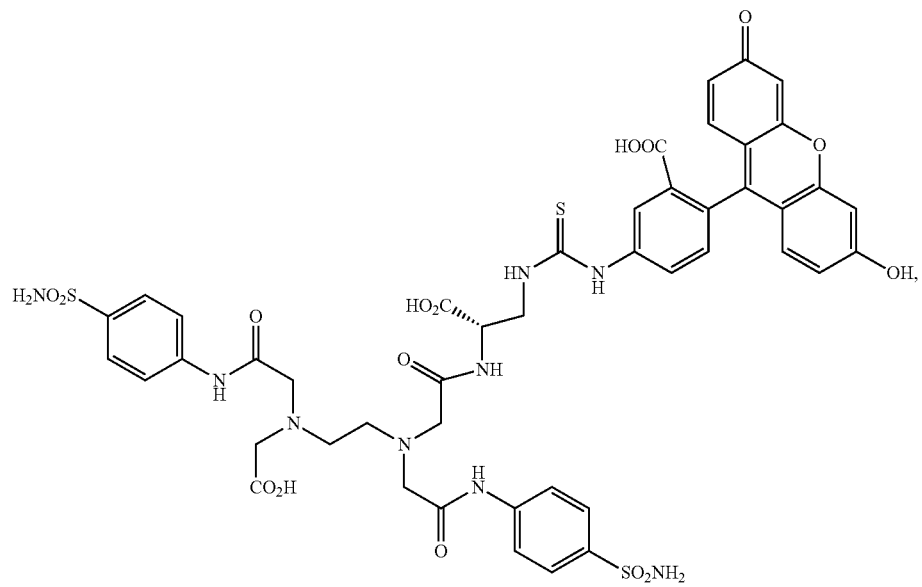
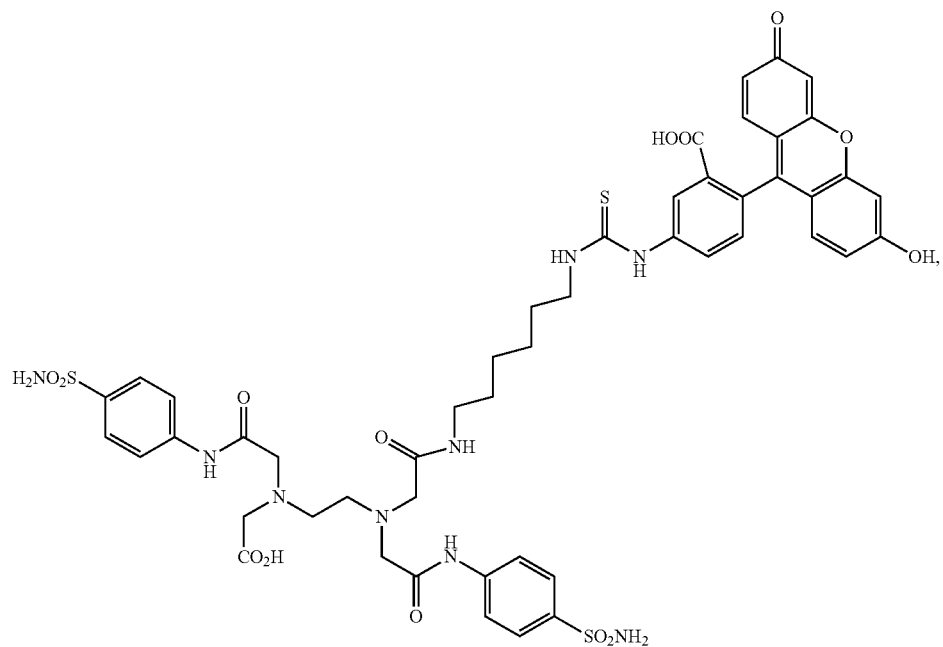

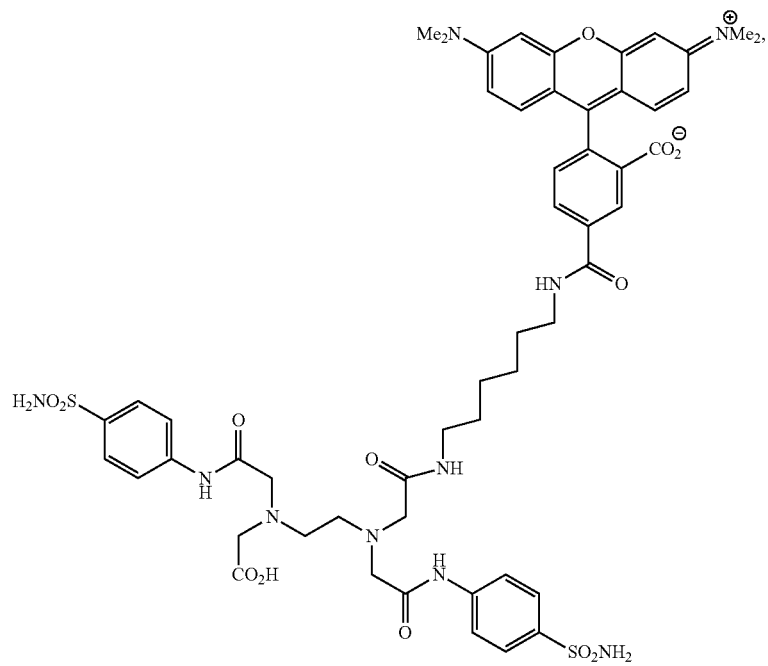
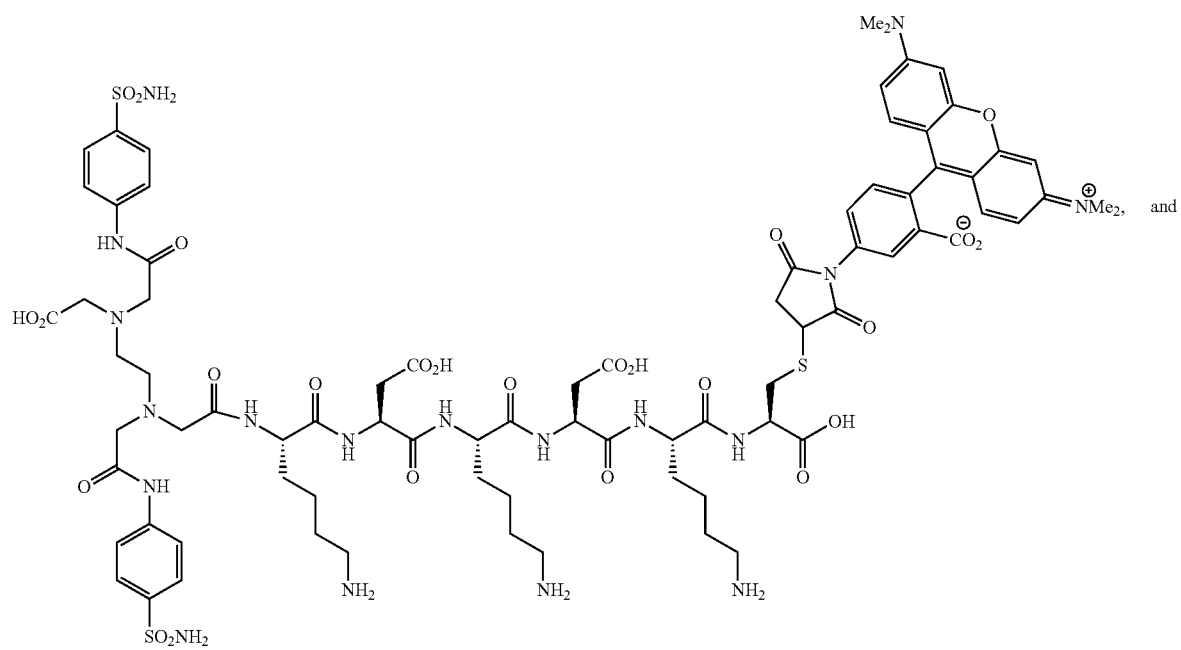

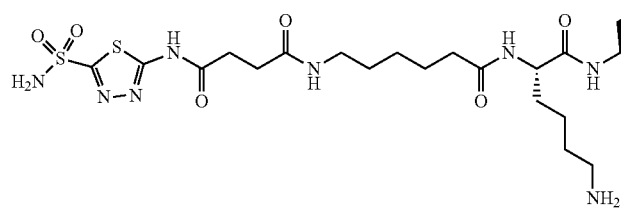
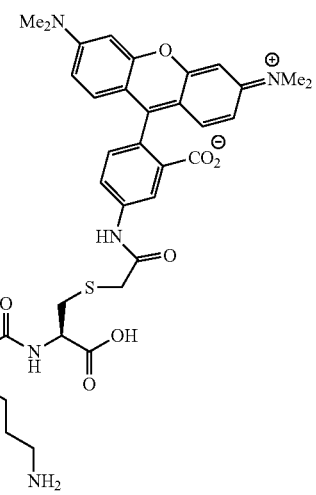

or a pharmaceutically acceptable salt thereof.

59. A method of treating cancer in a subject, comprising,
   a. administering to the subject an effective amount of a conjugate or composition according to any one of clauses 1 to 54; or a pharmaceutically acceptable salt thereof.

60. The method of clause 59, wherein the subject has a CA IX expressing cancer.

61. The method of clause 59 or 60, wherein the cancer is selected from the group consisting of lung, colorectal, gastric, pancreatic, breast, cervical, bladder, ovarian, brain, head & neck, oral and kidney cancer.

62. A conjugate according to any one of clause 1 to 53, or a pharmaceutically acceptable salt thereof, for use in a method of treating cancer in a subject.

63. The conjugate of clause 62, wherein the method comprises administering to the subject an amount of the conjugate effective for treating the cancer.

64. The conjugate of clause 62 or 63, wherein the cancer is selected from the group consisting of lung, colorectal, gastric, pancreatic, breast, cervical, bladder, ovarian, brain, head & neck, oral and kidney cancer.

65. Use of a conjugate according to any one of clauses 1 to 53, or a pharmaceutically acceptable salt thereof, in the preparation of a medicament useful for treating cancer in a subject.

66. The use of clause 65, wherein the method comprises administering to the subject an amount of the conjugate effective for treating the cells.

67. The use of clause 65 or 66, wherein the cancer is selected from the group consisting of lung, colorectal, gastric, pancreatic, breast, cervical, bladder, ovarian, brain, head & neck, oral and kidney cancer.

68. A method of imaging a population of cells in vitro, comprising
   a. contacting the cells with a conjugate according to any one of clauses 55 to 58, to provide labelled cells, and
   b. visualizing the labelled cells with a fluorescent light source.

69. A conjugate according to any one of clauses 55 to 58, for use in a method of imaging a population of cells in vitro.

70. The conjugate of clause 66, wherein the method comprises
   a. contacting the cells with a conjugate according to any one of clauses 55 to 58, to provide labelled cells, and
   b. visualizing the labelled cells with a fluorescent light source.

BRIEF DESCRIPTION OF THE DRAWINGS

FIG. 1 shows the assessment of CA IX protein expression in HT-29 cells and RCC4 cells.

FIG. 5 shows results for the CA IX Competitive Binding Assay (McCoy's 5A Medium+$Zn^2$) in HT29 cells where 2 nM $^{125}$I-EC2674, 2 hr, 37° C., 1.3% $O_2$.

FIG. 7 shows visualization of in vitro binding of a CA IX imaging conjugate in HT-29 cells.

FIG. 8 shows in vivo efficacy studies of CA IX inhibitor conjugates in HT-29 implanted cells.

FIG. 9 shows an in vivo efficacy study of a CA IX inhibitor conjugate in HT-29 implanted cells.

DEFINITIONS

Figure 1A:
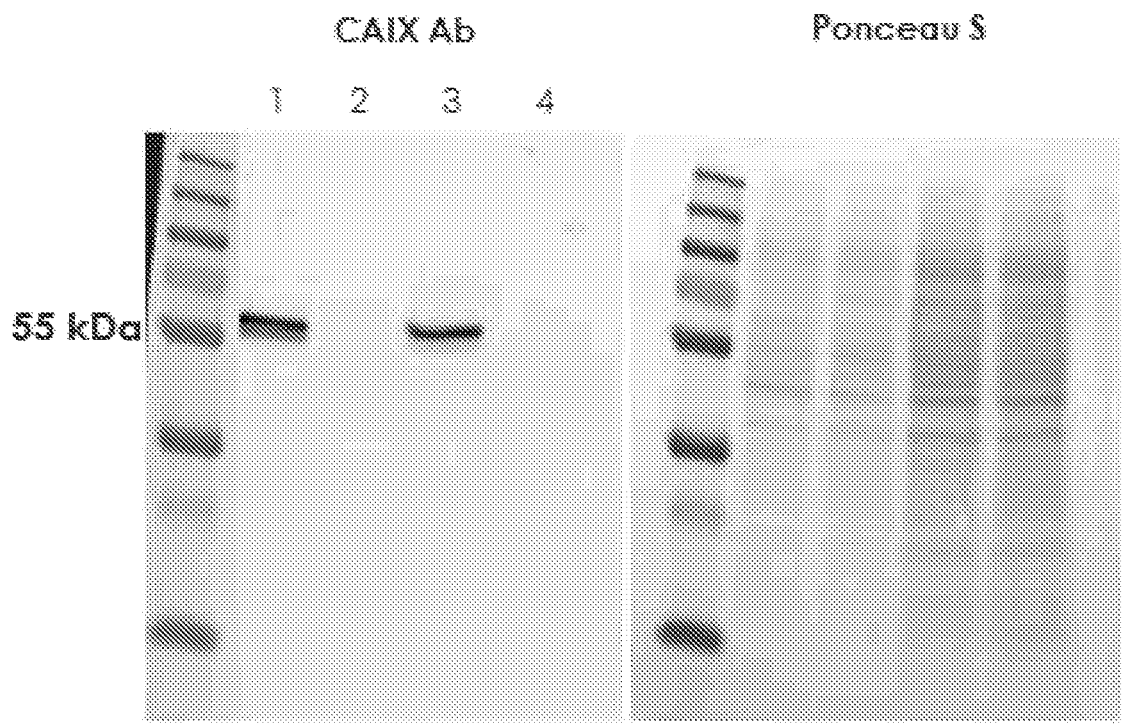
FIG. 1A shows results of CA IX expression analysis in RCC4 cells. Lane 1: RCC4 cells+vector alone; Lane 2: RCC4 cells+VHL; Lane 3: KB cells+200 μM $CoCl_2$ for 24 hr; Lane 4: KB cells, untreated.

As used herein, the term "alkyl" includes a chain of carbon atoms, which is optionally branched and contains from 1 to 20 carbon atoms. It is to be further understood that in certain embodiments, alkyl may be advantageously of limited length, including $C_1$-$C_{12}$, $C_1$-$C_{10}$, $C_1$-$C_8$, $C_1$-$C_7$, $C_1$-$C_6$, and $C_1$-$C_4$, Illustratively, such particularly limited length alkyl groups, including $C_1$-$C_8$, $C_1$-$C_7$, $C_1$-$C_6$, and $C_1$-$C_4$, and the like may be referred to as "lower alkyl." Illustrative alkyl groups include, but are not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl, and the like. Alkyl may be substituted or unsubstituted. Typical substituent groups include cycloalkyl, aryl, heteroaryl, heteroalicyclic, hydroxy, alkoxy, aryloxy, mercapto, alkylthio, arylthio, cyano, halo, carbonyl, oxo, (=O), thiocarbonyl, O-carbamyl, N-carbamyl, O-thiocarbamyl, N-thiocarbamyl, C-amido, N-amido, C-carboxy, O-carboxy, nitro, and amino, or as described in the various embodiments provided herein. It will be understood that "alkyl" may be combined with other groups, such as those provided above, to form a functionalized alkyl. By way of example, the combination of an "alkyl" group, as described herein, with a "carboxy" group may be referred to as a "carboxyalkyl" group. Other non-limiting examples include hydroxyalkyl, aminoalkyl, and the like. In other embodiments, an "alkyl" group can be combined with another group, such as an aryl group, for example $C_6$-$C_{10}$ aryl-($C_1$-$C_6$ alkyl), which provides for a group such as benzyl (i.e. $C_6H_5$—$CH_2$—).

As used herein, the term "alkenyl" includes a chain of carbon atoms, which is optionally branched, and contains from 2 to 20 carbon atoms, and also includes at least one carbon-carbon double bond (i.e. C=C). It will be understood that in certain embodiments, alkenyl may be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkenyl groups, including $C_2$-$C_8$, $C_2$-$C_7$, $C_2$-$C_6$, and $C_2$-$C_4$ may be referred to as lower alkenyl. Alkenyl may be unsubstituted, or substituted as described for alkyl or as described in the various embodiments provided herein. Illustrative alkenyl groups include, but are not limited to, ethenyl, 1-propenyl, 2-propenyl, 1-, 2-, or 3-butenyl, and the like.

As used herein, the term "alkynyl" includes a chain of carbon atoms, which is optionally branched, and contains from 2 to 20 carbon atoms, and also includes at least one carbon-carbon triple bond (i.e. C≡C). It will be understood that in certain embodiments alkynyl may each be advantageously of limited length, including $C_2$-$C_{12}$, $C_2$-$C_9$, $C_2$-$C_8$, $C_2$-$C_7$, $C_2$-$C_6$, and $C_2$-$C_4$. Illustratively, such particularly limited length alkynyl groups, including $C_2$-$C_8$, $C_2$-$C_7$, $C_2$-$C_6$, and $C_2$-$C_4$ may be referred to as lower alkynyl. Alkenyl may be unsubstituted, or substituted as described for alkyl or as described in the various embodiments provided herein. Illustrative alkenyl groups include, but are not limited to, ethynyl, 1-propynyl, 2-propynyl, 1-, 2-, or 3-butynyl, and the like.

As used herein, the term "aryl" refers to an all-carbon monocyclic or fused-ring polycyclic group of 6 to 12 carbon atoms having a completely conjugated pi-electron system. It will be understood that in certain embodiments, aryl may be advantageously of limited size such as $C_6$-$C_{10}$ aryl. Illustrative aryl groups include, but are not limited to, phenyl, naphthalenyl and anthracenyl. The aryl group may be unsubstituted, or substituted as described for alkyl or as described in the various embodiments provided herein.

As used herein, the term "cycloalkyl" refers to a 3 to 15 member all-carbon monocyclic ring, an all-carbon 5-member/6-member or 6-member/6-member fused bicyclic ring, or a multicyclic fused ring (a "fused" ring system means that each ring in the system shares an adjacent pair of carbon atoms with each other ring in the system) group where one or more of the rings may contain one or more double bonds but the cycloalkyl does not contain a completely conjugated pi-electron system. It will be understood that in certain embodiments, cycloalkyl may be advantageously of limited size such as $C_3$-$C_{13}$, $C_3$-$C_6$, $C_3$-$C_6$ and $C_4$-$C_6$. Cycloalkyl may be unsubstituted, or substituted as described for alkyl or as described in the various embodiments provided herein. Illustrative cycloalkyl groups include, but are not limited to, cyclopropyl, cyclobutyl, cyclopentyl, cyclopentenyl, cyclopentadienyl, cyclohexyl, cyclohexenyl, cycloheptyl, adamantyl, norbornyl, norbornenyl, 9H-fluoren-9-yl, and the like.

As used herein, the term "heterocycloalkyl" refers to a monocyclic or fused ring group having in the ring(s) from 3 to 12 ring atoms, in which at least one ring atom is a heteroatom, such as nitrogen, oxygen or sulfur, the remaining ring atoms being carbon atoms. Heterocycloalkyl may optionally contain 1, 2, 3 or 4 heteroatoms. Heterocycloalkyl may also have one of more double bonds, including double bonds to nitrogen (e.g. C=N or N=N) but does not contain a completely conjugated pi-electron system. It will be understood that in certain embodiments, heterocycloalkyl may be advantageously of limited size such as 3- to 7-membered heterocycloalkyl, 5- to 7-membered heterocycloalkyl, and the like. Heterocycloalkyl may be unsubstituted, or substituted as described for alkyl or as described in the various embodiments provided herein. Illustrative heterocycloalkyl groups include, but are not limited to, oxiranyl, thianaryl, azetidinyl, oxetanyl, tetrahydrofuranyl, pyrrolidinyl, tetrahydropyranyl, piperidinyl, 1,4-dioxanyl, morpholinyl, 1,4-dithianyl, piperazinyl, oxepanyl, 3,4-dihydro-2H-pyranyl, 5,6-dihydro-2H-pyranyl, 2H-pyranyl, 1, 2, 3, 4-tetrahydropyridinyl, and the like.

As used herein, the term "heteroaryl" refers to a monocyclic or fused ring group of 5 to 12 ring atoms containing one, two, three or four ring heteroatoms selected from nitrogen, oxygen and sulfur, the remaining ring atoms being carbon atoms, and also having a completely conjugated pi-electron system. It will be understood that in certain embodiments, heteroaryl may be advantageously of limited size such as 3- to 7-membered heteroaryl, 5- to 7-membered heteroaryl, and the like. Heteroaryl may be unsubstituted, or substituted as described for alkyl or as described in the various embodiments provided herein. Illustrative heteroaryl groups include, but are not limited to, pyrrolyl, furanyl, thiophenyl, imidazolyl, oxazolyl, thiazolyl, pyrazolyl, pyridinyl, pyrimidinyl, quinolinyl, isoquinolinyl, purinyl, tetrazolyl, triazinyl, pyrazinyl, tetrazinyl, quinazolinyl, quinoxalinyl, thienyl, isoxazolyl, isothiazolyl, oxadiazolyl, thiadiazolyl, triazolyl, benzimidazolyl, benzoxazolyl, benzthiazolyl, benzisoxazolyl, benzisothiazolyl and carbazoloyl, and the like.

As used herein, "hydroxy" or "hydroxyl" refers to an —OH group.

As used herein, "alkoxy" refers to both an —O-(alkyl) or an —O-(unsubstituted cycloalkyl) group. Representative examples include, but are not limited to, methoxy, ethoxy, propoxy, butoxy, cyclopropyloxy, cyclobutyloxy, cyclopentyloxy, cyclohexyloxy, and the like.

As used herein, "aryloxy" refers to an —O-aryl or an —O-heteroaryl group. Representative examples include, but are not limited to, phenoxy, pyridinyloxy, furanyloxy, thienyloxy, pyrimidinyloxy, pyrazinyloxy, and the like, and the like.

As used herein, "mercapto" refers to an —SH group.

As used herein, "alkylthio" refers to an —S-(alkyl) or an —S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

As used herein, "arylthio" refers to an —S-aryl or an —S-heteroaryl group. Representative examples include, but are not limited to, phenylthio, pyridinylthio, furanylthio, thienylthio, pyrimidinylthio, and the like.

As used herein, "halo" or "halogen" refers to fluorine, chlorine, bromine or iodine.

As used herein, "trihalomethyl" refers to a methyl group having three halo substituents, such as a trifluoromethyl group.

As used herein, "cyano" refers to a —CN group.

As used herein, "sulfinyl" refers to a —S(O)R" group, where R" is any R group as described in the various embodiments provided herein, or R" may be a hydroxyl group.

As used herein, "sulfonyl" refers to a —S(O)$_2$R" group, where R" is any R group as described in the various embodiments provided herein, or R" may be a hydroxyl group.

As used herein, "S-sulfonamido" refers to a —S(O)$_2$NR"R" group, where R" is any R group as described in the various embodiments provided herein.

As used herein, "N-sulfonamido" refers to a —NR"S(O)$_2$R" group, where R" is any R group as described in the various embodiments provided herein.

As used herein, "O-carbamyl" refers to a —OC(O)NR"R" group, where R" is any R group as described in the various embodiments provided herein.

As used herein, "N-carbamyl" refers to an R"OC(O)NR"— group, where R" is any R group as described in the various embodiments provided herein.

As used herein, "O-thiocarbamyl" refers to a —OC(S)NR"R" group, where R" is any R group as described in the various embodiments provided herein.

As used herein, "N-thiocarbamyl" refers to a R"OC(S)NR"— group, where R" is any R group as described in the various embodiments provided herein.

As used herein, "amino" refers to an —NR"R" group, where R" is any R group as described in the various embodiments provided herein.

As used herein, "C-amido" refers to a —C(O)NR"R" group, where R" is any R group as described in the various embodiments provided herein.

As used herein, "N-amido" refers to a R"C(O)NR"— group, where R" is any R group as described in the various embodiments provided herein.

As used herein, "nitro" refers to a —NO$_2$ group.

As used herein, "bond" refers to a covalent bond.

As used herein, "optional" or "optionally" means that the subsequently described event or circumstance may but need not occur, and that the description includes instances where the event or circumstance occurs and instances in which it does not. For example, "heterocycle group optionally substituted with an alkyl group" means that the alkyl may but need not be present, and the description includes situations where the heterocycle group is substituted with an alkyl group and situations where the heterocycle group is not substituted with the alkyl group.

As used herein, "independently" means that the subsequently described event or circumstance is to be read on its own relative to other similar events or circumstances. For example, in a circumstance where several equivalent hydrogen groups are optionally substituted by another group described in the circumstance, the use of "independently optionally" means that each instance of a hydrogen atom on the group may be substituted by another group, where the groups replacing each of the hydrogen atoms may be the same or different. Or for example, where multiple groups exist all of which can be selected from a set of possibilities, the use of "independently" means that each of the groups can be selected from the set of possibilities separate from any other group, and the groups selected in the circumstance may be the same or different.

As used herein, "amino acid" (a.k.a. "AA") means any molecule that includes an alpha-carbon atom covalently bonded to an amino group and an acid group. The acid group may include a carboxyl group. "Amino acid" may include molecules having one of the formulas:

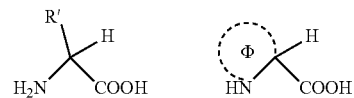

wherein R' is a side group and Φ includes at least 3 carbon atoms. "Amino acid" includes stereoisomers such as the D-amino acid and L-amino acid forms. Illustrative amino acid groups include, but are not limited to, the twenty endogenous human amino acids and their derivatives, such as lysine (Lys), asparagine (Asn), threonine (Thr), serine (Ser), isoleucine (Ile), methionine (Met), proline (Pro), histidine (His), glutamine (Gln), arginine (Arg), glycine (Gly), aspartic acid (Asp), glutamic acid (Glu), alanine (Ala), valine (Val), phenylalanine (Phe), leucine (Leu), tyrosine (Tyr), cysteine (Cys), tryptophan (Trp), phosphoserine (PSER), sulfo-cysteine, arginosuccinic acid (ASA), hydroxyproline, phosphoethanolamine (PEA), sarcosine (SARC), taurine (TAU), carnosine (CARN), citrulline (CIT), anserine (ANS), 1,3-methyl-histidine (ME-HIS), alpha-amino-adipic acid (AAA), beta-alanine (BALA), ethanolamine (ETN), gamma-amino-butyric acid (GABA), beta-amino-isobutyric acid (BAIA), alpha-amino-butyric acid (BABA), L-allo-cystathionine (cystathionine-A; CYSTA-A), L-cystathionine (cystathionine-B; CYSTA-B), cystine, allo-isoleucine (ALLO-ILE), DL-hydroxylysine (hydroxylysine (I)), DL-allo-hydroxylysine (hydroxylysine (2)), ornithine (ORN), homocystine (HCY), and derivatives thereof. In connection with the embodiments described herein, amino acids can be covalently attached to other portions of the conjugates described herein through their alpha-amino and carboxy functional groups (i.e. in a peptide bond configuration), or through their side chain functional groups (such as the side chain carboxy group in glutamic acid) and either their alpha-amino or carboxy functional groups. It will be understood that amino acids, when used in connection with the conjugates described herein, may exist as zwitterions in a conjugate in which they are incorporated.

As used herein, "prodrug" refers to a compound that can be administered to a subject in a pharmacologically inactive form which then can be converted to a pharmacologically active form through a normal metabolic process, such as hydrolysis of an oxazolidine. It will be understood that the metabolic processes through which a prodrug can be converted to an active drug include, but are not limited to, one or more spontaneous chemical reaction(s), enzyme-catalyzed chemical reaction(s), and/or other metabolic chemical reaction(s), or a combination thereof. It will be appreciated that understood that a variety of metabolic processes are known in the art, and the metabolic processes through which the prodrugs described herein are converted to active drugs are non-limiting. A prodrug can be a precursor chemical compound of a drug that has a therapeutic effect on a subject.

As used herein, the term "therapeutically effective amount" refers to an amount of a drug or pharmaceutical agent that elicits the biological or medicinal response in a subject (i.e. a tissue system, animal or human) that is being sought by a researcher, veterinarian, medical doctor or other clinician, which includes, but is not limited to, alleviation of the symptoms of the disease or disorder being treated. In one aspect, the therapeutically effective amount is that amount of an active which may treat or alleviate the disease or symptoms of the disease at a reasonable benefit/risk ratio applicable to any medical treatment. In another aspect, the therapeutically effective amount is that amount of an inactive prodrug which when converted through normal metabolic processes to produce an amount of active drug capable of eliciting the biological or medicinal response in a subject that is being sought.

It is also appreciated that the dose, whether referring to monotherapy or combination therapy, is advantageously selected with reference to any toxicity, or other undesirable side effect, that might occur during administration of one or more of the conjugates described herein. Further, it is appreciated that the co-therapies described herein may allow for the administration of lower doses of conjugates that show such toxicity, or other undesirable side effect, where those lower doses are below thresholds of toxicity or lower in the therapeutic window than would otherwise be administered in the absence of a cotherapy.

As used herein, "administering" includes all means of introducing the conjugates and compositions described herein to the host animal, including, but are not limited to, oral (po), intravenous (iv), intramuscular (im), subcutaneous (sc), transdermal, inhalation, buccal, ocular, sublingual, vaginal, rectal, and the like. The conjugates and compositions described herein may be administered in unit dosage forms and/or formulations containing conventional nontoxic pharmaceutically-acceptable carriers, adjuvants, and/or vehicles.

As used herein "pharmaceutical composition" or "composition" refers to a mixture of one or more of the conjugates described herein, or pharmaceutically acceptable salts, solvates, hydrates thereof, with other chemical components, such as pharmaceutically acceptable excipients. The purpose of a pharmaceutical composition is to facilitate administration of a conjugate to a subject. Pharmaceutical compositions suitable for the delivery of conjugates described and methods for their preparation will be readily apparent to those skilled in the art. Such compositions and methods for their preparation may be found, for example, in 'Remington's Pharmaceutical Sciences', 19th Edition (Mack Publishing Company, 1995).

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

DETAILED DESCRIPTION

In accordance with Applicants' disclosure described herein, the embodiments of the numbered clauses provided in the summary above, or any combination thereof, are contemplated for combination with any of the embodiments described in the Detailed Description section of this patent application.

In each of the foregoing and each of the following embodiments, it is to be understood that the formulae include and represent not only all pharmaceutically acceptable salts of the conjugates, but also include any and all hydrates and/or solvates of the conjugate formulae. It is appreciated that certain functional groups, such as the hydroxy, amino, and like groups form complexes and/or coordination conjugates with water and/or various solvents, in the various physical forms of the conjugates. Accordingly, the above formulae are to be understood to include and represent those various hydrates and/or solvates. It is also to be understood that the non-hydrates and/or non-solvates of the conjugate formulae are described by such formula, as well as the hydrates and/or solvates of the conjugate formulae.

It will be appreciated that CA IX ligands useful in connection with the present disclosure are not particularly limited by structure. Useful CA IX ligand can be any drug or compound that shows binding affinity for CA IX, such as an inhibitor, an antagonist or an agonist.

In some embodiments, the CA IX inhibitor is of the formula

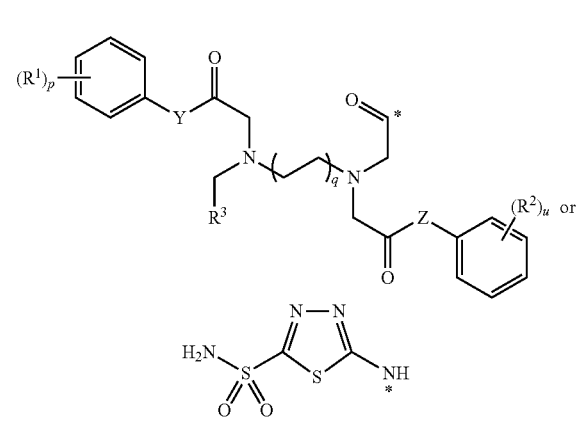

wherein $R^1$, $R^2$, $R^3$, Y, Z, p, u, q and * are as defined herein. In some aspects of these embodiments, p is 1. In some aspects of these embodiments, u is 1. In some aspects of these embodiments, q is 1. In some aspects of these embodiments, $R^1$ is —$S(O)_2NR^4R^5$. In some aspects of these embodiments, $R^1$ is —$S(O)_2NR^4R^5$ in the para-position of the ring to which $R^1$ is attached. In some aspects of these embodiments, $R^2$ is —$S(O)_2NR^4R^5$. In some aspects of these embodiments, $R^2$ is —$S(O)_2NR^4R^5$ in the para-position of the ring to which $R^2$ is attached. In some aspects of these embodiments, $R^4$ and $R^5$ are H. In some aspects of these embodiments, $R^3$ is —$C(O)OR^7$. In some aspects of these embodiments, $R^7$ is H or —$CH_3$. In some aspects of these embodiments, Y is —$NR^8$—. In some aspects of these embodiments, Z is —$NR^9$—. In some aspects of these embodiments, $R^8$ is H or —$CH_3$. In some aspects of these embodiments, $R^9$ is H or —$CH_3$. In some aspects of these embodiments, the CA IX inhibitor is of the formula

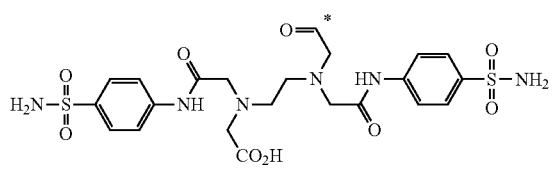 [SMILES: NS(=O)(=O)c1ccc(NC(=O)CN(CC=O)CCN(CC(=O)O)CC(=O)Nc2ccc(S(N)(=O)=O)cc2)cc1]

wherein * is as defined herein.

In some aspects of these embodiments, $R^6$ and $R^8$ taken together form a covalent bond from $R^3$ to Y to form a six-membered ring. In some aspects of these embodiments, the CA IX inhibitor is of the formula

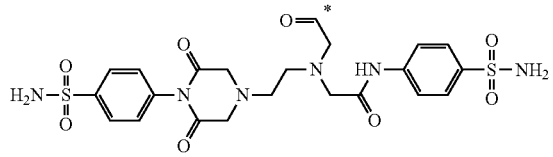 [SMILES: NS(=O)(=O)c1ccc(NC(=O)CN(CC=O)CCN2CC(=O)N(c3ccc(S(N)(=O)=O)cc3)C(=O)C2)cc1]

It will be appreciated that linkers useful in connection with the present disclosure are not particularly limited by structure. The linker can be any linker of from 2 to 100 atoms in length and composed of elements including C, N, O and S that covalently attaches a CA IX inhibitor to an agent. In some embodiments, the linker comprises simple groups, such as alkyl chain portions, ether portions (e.g. PEG), long chain amine portions, amino acid chain portions, a hydrazine portion, and the like, and combinations thereof. In some embodiments, linkers useful in connection with the present disclosure comprise one or more spacer linkers ($L^2$) selected from the group consisting of $C_1$-$C_{12}$ alkyl, —$(CR^{39}R^{39'})_rC(O)$—, —$(CR^{39}R^{39'})_rOC(O)$—, —$C(O)(CR^{39}R^{39'})_r$—, —$C(O)O(CR^{39}R^{39'})_r$—, —$NR^{39}R^{39'}C(O)(CR^{39}R^{39'})_r$—, —$(CH_2)_rNR^{39}$—, —$NR^{39}(CH_2)_r$—, —$NR^{39}(CH_2)_rNR^{39'}$—, —$(OCR^{39}R^{39'}CR^{39}R^{39'})_rC(O)$—, —$(OCR^{39}R^{39'}CR^{39}R^{39'}CR^{39}R^{39'})_rC(O)$—, —$OC(O)(CR^{44}R^{44'})_t$—, —$C(O)(CR^{44}R^{44'})_t$—, —$NR^{42}CR^{43}R^{43'}CR^{43}R^{43'}(OCR^{44}R^{44'}CR^{44}R^{44'})_r$—, —$CR^{43}R^{43'}CR^{43}R^{43'}(OCR^{44}R^{44'}CR^{44}R^{44'})_rNR^{42}$—, —$NR^{42}C_6$-$C_{10}$ aryl($C_1$-$C_6$ alkyl)OC(O)—, —$C(O)CR^{43}R^{43'}CR^{43}R^{43'}(OCR^{44}R^{44'}CR^{44}R^{44'})_rNR^{42}$—, —$NR^{42}CR^{43}R^{43'}CR^{43}R^{43'}(OCR^{44}R^{44'}CR^{44}R^{44'})_rC(O)$—, and —$NR^{42}CR^{43}R^{43'}CR^{43}R^{43'}(CR^{44}=CR^{44'})_t$—; and combinations thereof;

wherein each $R^{39}$ and $R^{39'}$ is independently selected from the group consisting of H, halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{40}$, —$OC(O)R^{40}$, —$OC(O)NR^{40}R^{40'}$, —$OS(O)R^{40}$, —$OS(O)_2R^{40}$, —$SR^{40}$, —$S(O)R^{40}$, —$S(O)_2R^{40}$, —$S(O)NR^{40}R^{40'}$, —$S(O)_2NR^{40}R^{40'}$, —$OS(O)NR^{40}R^{40'}$, —$OS(O)_2NR^{40}R^{40'}$, —$NR^{40}R^{40'}$, —$NR^{40}C(O)R^{41}$, —$NR^{40}C(O)OR^{41}$, —$NR^{40}C(O)NR^{41}R^{41'}$, —$NR^{40}S(O)R^{41}$, —$NR^{40}S(O)_2R^{41}$, —$NR^{40}S(O)NR^{41}R^{41'}$, —$NR^{40}S(O)_2NR^{41}R^{41'}$, —$C(O)R^{40}$, —$C(O)OR^{40}$ and —$C(O)NR^{40}R^{40'}$;

$R^{40}$, $R^{40'}$, $R^{41}$ and $R^{41'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl; and r in each instance is an integer from 1 to 40;

$R^{42}$ is selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{45}$, —$OC(O)R^{45}$, —$OC(O)NR^{45}R^{45'}$, —$OS(O)R^{45}$, —$OS(O)_2R^{45}$, —$SR^{45}$, —$S(O)R^{45}$, —$S(O)_2R^{45}$, —$S(O)NR^{45}R^{45'}$, —$S(O)_2NR^{45}R^{45'}$, —$OS(O)NR^{45}R^{45'}$, —$OS(O)_2NR^{45}R^{45'}$, —$NR^{45}R^{45'}$, —$NR^{45}C(O)R^{46}$, —$NR^{45}C(O)OR^{46}$, —$NR^{45}C(O)NR^{46}R^{46'}$, —$NR^{45}S(O)R^{46}$, —$NR^{45}S(O)_2R^{46}$, —$NR^{45}S(O)NR^{46}R^{46'}$, —$NR^{45}S(O)_2NR^{46}R^{46'}$, —$C(O)R^{45}$, —$C(O)OR^{45}$ or —$C(O)NR^{45}R^{45'}$;

each $R^{43}$, $R^{43'}$, $R^{44}$ and $R^{44'}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{47}$, —$OC(O)R^{47}$, —$OC(O)NR^{47}R^{47'}$, —$OS(O)R^{47}$, —$OS(O)_2R^{47}$, —$SR^{47}$, —$S(O)R^{47}$, —$S(O)_2R^{47}$, —$S(O)NR^{47}R^{47'}$, —$S(O)_2NR^{47}R^{47'}$, —$OS(O)NR^{47}R^{47'}$, —$OS(O)_2NR^{47}R^{47'}$, —$NR^{46}R^{47'}$, —$NR^{47}C(O)R^{48}$, —$NR^{47}C(O)OR^{48}$, —$NR^{47}C(O)NR^{48}R^{48'}$, —$NR^{47}S(O)R^{48}$, —$NR^{47}S(O)_2R^{48}$, —$NR^{47}S(O)NR^{48}R^{48'}$, —$NR^{47}S(O)_2NR^{48}R^{48'}$, —$C(O)R^{47}$, —$C(O)OR^{47}$ or —$C(O)NR^{47}R^{47'}$;

$R^{45}$, $R^{45'}$, $R^{46}$, $R^{46'}$, $R^{47}$, $R^{47'}$, $R^{48}$ and $R^{48'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and t is in each instance an integer from 1 to 40.

In some aspects, the linker comprises at least one $L^2$ of the formula $C_1$-$C_{12}$ alkyl. In some aspects, the linker comprises at least one $L^2$ of the formula —$(CR^{39}R^{39'})_rC(O)$—. In some aspects, the linker comprises at least one $L^2$ of the formula —$(CR^{39}R^{39'})_rOC(O)$—. In some aspects, the linker comprises at least one $L^2$ of the formula —$C(O)(CR^{39}R^{39'})_r$—. In some aspects, the linker comprises at least one $L^2$ of the formula —$C(O)O(CR^{39}R^{39'})_r$—. In some aspects, the linker comprises at least one $L^2$ of the formula —$NR^{39}R^{39'}C(O)(CR^{39}R^{39'})_r$—. In some aspects, the linker comprises at least one $L^2$ of the formula —$(CH_2)_rNR^{39}$—. In some aspects, the linker comprises at least one $L^2$ of the formula —$NR^{39}$ $(CH_2)_t$—. In some aspects, the linker comprises at least one $L^2$ of the formula —$NR^{39}(CH_2)_tNR^{39'}$—. In some aspects, the linker comprises at least one $L^2$ of the formula —$(OCR^{39}R^{39'}CR^{39}R^{39'})_tC(O)$—. In some aspects, the linker comprises at least one $L^2$ of the formula —$(OCR^{39}R^{39'}CR^{39}R^{39'}CR^{39}R^{39'})_tC(O)$—. In some aspects, the linker comprises at least one $L^2$ of the formula —$OC(O)(CR^{44}R^{44'})_t$—. In some aspects, the linker comprises at least one $L^2$ of the formula —$C(O)(CR^{44}R^{44'})_t$—. In some aspects, the linker comprises at least one $L^2$ of the formula —$NR^{42}CR^{43}R^{43'}CR^{43}R^{43'}(OCR^{44}R^{44'}CR^{44}R^{44'})_t$—. In some aspects, the linker comprises at least one $L^2$ of the formula —$CR^{43}R^{43'}CR^{43}R^{43'}(OCR^{44}R^{44'}CR^{44}R^{44'})_tNR^{42}$—. In some aspects, the linker comprises at least one $L^2$ of the formula —$NR^{42}C_6$-$C_{10}$ aryl($C_1$-$C_6$ alkyl)OC(O)—. In some aspects, the linker comprises at least one $L^2$ of the formula —$C(O)CR^{43}R^{43'}CR^{43}R^{43'}(OCR^{44}R^{44'}CR^{44}R^{44'})_tNR^{42}$—. In some aspects, the linker comprises at least one $L^2$ of the formula —$NR^{42}CR^{43}R^{43'}CR^{43}R^{43'}(OCR^{44}R^{44'}CR^{44}R^{44'})_tC(O)$—. In some aspects, the linker comprises at least one $L^2$ of the formula —$NR^{42}CR^{43}R^{43'}CR^{43}R^{43'}(CR^{44}=CR^{44'})_t$—.

In some embodiments, the linker can comprise a chain of amino acids. In some embodiments, the linker can comprise a dipeptide or a tripeptide. In some embodiments, the linker can comprise one or more amino acids selected from the group consisting of Asp, Arg, Lys, Cys and Glu. In some embodiments, the linker can comprise a tripeptide portion that is -Asp-Asp-Asp-. In some embodiments, the linker can comprise a dipeptide portion that is -Asp-Asp-. linker can comprise a tripeptide portion that is -Lys-Asp-Lys-Asp-Lys-. In some embodiments, the linker can comprise a tripeptide portion that is -Asp-Asp-Cys-. In some embodiments, the linker can comprise a tetrapeptide portion that is -Asp-Asp-Asp-Cys-.

In some embodiments, the linker comprises a releasable linker where the term "releasable linker" refers to a linker that includes at least one bond that can be broken under physiological conditions, such as a pH-labile, acid-labile, base-labile, oxidatively labile, metabolically labile, biochemically labile, or enzyme-labile bond. It is appreciated that such physiological conditions resulting in bond breaking do not necessarily include a biological or metabolic process, and instead may include a standard chemical reaction, such as a hydrolysis reaction, for example, at physiological pH, or as a result of compartmentalization into a cellular organelle such as an endosome having a lower pH than cytosolic pH. In some embodiments, the releasable linker comprises a disulfide bond. In some embodiments, the releasable linker comprises a moiety selected from the group consisting of

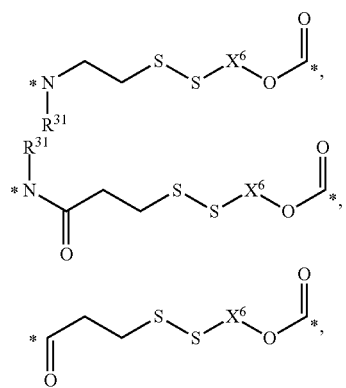

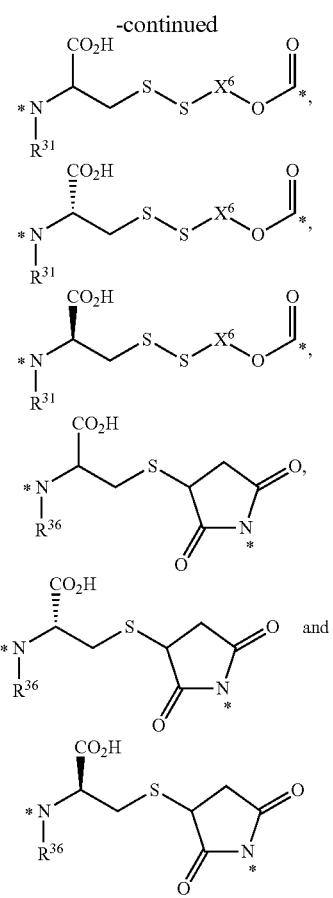

wherein each $R^{31}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{32}$, —$OC(O)R^{32}$, —$OC(O)NR^{32}R^{32'}$, —$OS(O)R^{32}$, —$OS(O)_2R^{32}$, —$SR^{32}$, —$S(O)R^{32}$, —$S(O)_2R^{32}$, —$S(O)NR^{32}R^{32'}$, —$S(O)_2NR^{32}R^{32'}$, —$OS(O)NR^{32}R^{32'}$, —$OS(O)_2NR^{32}R^{32'}$, —$NR^{32}R^{32'}$, —$NR^{32}C(O)R^{33}$, —$NR^{32}C(O)OR^{33}$, —$NR^{32}C(O)NR^{33}R^{33'}$, —$NR^{32}S(O)R^{33}$, —$NR^{32}S(O)_2R^{33}$, —$NR^{32}S(O)NR^{33}R^{33'}$, —$NR^{32}S(O)_2NR^{33}R^{33'}$, —$C(O)R^{32}$, —$C(O)OR^{32}$ or —$C(O)NR^{32}R^{32'}$;

each $X^6$ is independently $C_1$-$C_6$ alkyl or $C_6$-$C_{10}$ aryl-($C_1$-$C_6$ alkyl), wherein each hydrogen atom in $C_1$-$C_6$ alkyl and $C_6$-$C_{10}$ aryl-($C_1$-$C_6$ alkyl) is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{34}$, —$OC(O)R^{34}$, —$OC(O)NR^{34}R^{34'}$, —$OS(O)R^{34}$, —$OS(O)_2R^{34}$, —$SR^{34}$, —$S(O)R^{34}$, —$S(O)_2R^{34}$, —$S(O)NR^{34}R^{34'}$, —$S(O)_2NR^{34}R^{34'}$, —$OS(O)NR^{34}R^{34'}$, —$OS(O)_2NR^{34}R^{34'}$, —$NR^{34}R^{34'}$, —$NR^{34}C(O)R^{35}$, —$NR^{34}C(O)OR^{35}$, —$NR^{34}C(O)NR^{35}R^{35'}$, —$NR^{34}S(O)R^{35}$, —$NR^{34}S(O)_2R^{35}$, —$NR^{34}S(O)NR^{35}R^{35'}$, —$NR^{34}S(O)_2NR^{35}R^{35'}$, —$C(O)R^{34}$, —$C(O)OR^{34}$ or —$C(O)NR^{34}R^{34'}$;

each $R^{32}$, $R^{32'}$, $R^{33}$, $R^{33'}$, $R^{34}$, $R^{34'}$, $R^{35}$ and $R^{35'}$ are independently selected from the group consisting of H, D, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, and 5- to 7-membered heteroaryl;

each $R^{36}$ is independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, —$OR^{37}$, —$OC(O)R^{37}$, —$OC(O)NR^{37}R^{37'}$, —$OS(O)R^{37}$, —$OS(O)_2R^{37}$, —$SR^{37}$, —$S(O)R^{37}$, —$S(O)_2R^{37}$, —$S(O)NR^{37}R^{37'}$, —$S(O)_2NR^{37}R^{37'}$, —$OS(O)NR^{37}R^{37'}$, —$OS(O)_2NR^{37}R^{37'}$, —$NR^{37}R^{37'}$, —$NR^{37}C(O)R^{38}$, —$NR^{37}C(O)OR^{38}$, —$NR^{37}C(O)NR^{38}R^{38'}$, —$NR^{37}S(O)R^{38}$, —$NR^{37}S(O)_2R^{38}$, —$NR^{37}S(O)NR^{38}R^{38'}$, —$NR^{37}S(O)_2NR^{38}R^{38'}$, —$C(O)R^{37}$, —$C(O)OR^{37}$ or —$C(O)NR^{37}R^{37'}$;

$R^{37}$, $R^{37'}$, $R^{38}$ and $R^{38'}$ are each independently selected from the group consisting of H, $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl and 5- to 7-membered heteroaryl; and each * represents a covalent bond to the rest of the conjugate.

In some embodiments, the releasable linker comprises a structure of the formula

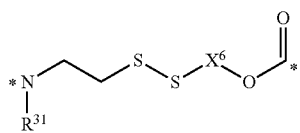

wherein $R^{31}$, $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

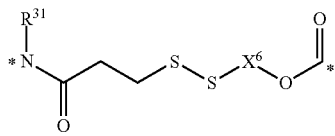

wherein $R^{31}$, $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

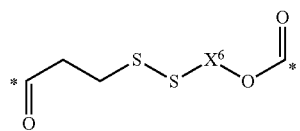

wherein $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

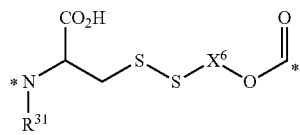

wherein $R^{31}$, $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

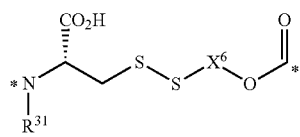

wherein $R^{31}$, $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

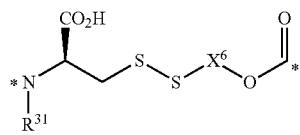

wherein $R^{31}$, $X^6$ and * are as defined herein. It will be appreciated that B and D or I can be covalently attached to the releasable linker shown above, either directly or through additional linker portions, at either end of the linker.

In some embodiments, the releasable linker comprises a structure of the formula

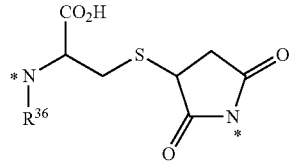

wherein $R^{36}$ and * are as defined herein. It will be appreciated that B and D or I can be covalently attached to the releasable linker shown above, either directly or through additional linker portions, at either end of the linker.

In some embodiments, the releasable linker comprises a structure of the formula

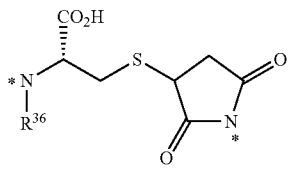

wherein $R^{36}$ and * are as defined herein. It will be appreciated that B and D or I can be covalently attached to the releasable linker shown above, either directly or through additional linker portions, at either end of the linker.

In some embodiments, the releasable linker comprises a structure of the formula

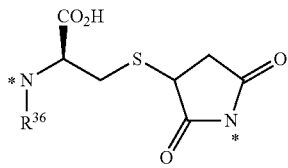

wherein $R^{36}$ and * are as defined herein. It will be appreciated that B and D or I can be covalently attached to the releasable linker shown above, either directly or through additional linker portions, at either end of the linker.

The agent used in connection with any of the conjugates described herein can be any molecule capable of modulating or otherwise modifying cell function, including pharmaceutically active compounds (e.g. a therapeutic agent), or any molecule capable of providing a measurable signal for imaging or visualized cells or tissues (e.g. an imaging agent).

Suitable molecules useful as therapeutic agents include, but are not limited to peptides, oligopeptides, retro-inverso oligopeptides, proteins, protein analogs in which at least one non-peptide linkage replaces a peptide linkage, apoproteins, glycoproteins, enzymes, coenzymes, enzyme inhibitors, amino acids and their derivatives, receptors and other membrane proteins; antigens and antibodies thereto; haptens and antibodies thereto; hormones, lipids, phospholipids, liposomes; toxins; antibiotics; analgesics; bronchodilators; beta-blockers; antimicrobial agents; antihypertensive agents; cardiovascular agents including antiarrhythmics, cardiac glycosides, antianginals and vasodilators; central nervous system agents including stimulants, psychotropics, antimanics, and depressants; antiviral agents; antihistamines; cancer drugs including chemotherapeutic agents; tranquilizers; anti-depressants; H-2 antagonists; anticonvulsants; antinauseants; prostaglandins and prostaglandin analogs; muscle relaxants; anti-inflammatory substances; stimulants; decongestants; antiemetics; diuretics; antispasmodics; antiasthmatics; anti-Parkinson agents; expectorants; cough suppressants; mucolytics; and mineral and nutritional additives.

In some embodiments, the therapeutic agent can be a tubulysin. Natural tubulysins are generally linear tetrapeptides consisting of N-methyl pipecolic acid (Mep), isoleucine (Ile), an unnatural aminoacid called tubuvaline (Tuv), and either an unnatural aminoacid called tubutyrosine (Tut, an analog of tyrosine) or an unnatural aminoacid called tubuphenylalanine (Tup, an analog of phenylalanine).

In some embodiments, the therapeutic agent is a tetrapeptide of the formula

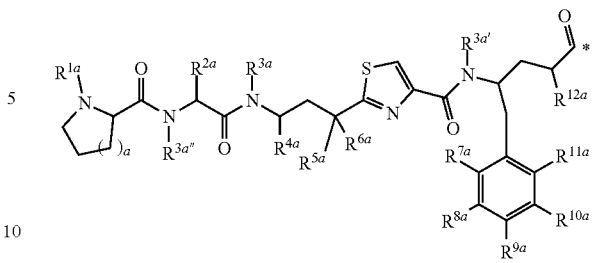

wherein $R^{1a}$, $R^{3a}$, $R^{3a'}$ and $R^{3a''}$ are each independently selected from the group consisting of H, $C_1$-$C_6$ alkyl, $C_2$-$C_6$ alkenyl, $C_2$-$C_6$ alkynyl and $C_3$-$C_6$ cycloalkyl, wherein each hydrogen atom in $C_1$-$C_6$ alkyl, $C_2$-$C_6$ alkenyl, $C_2$-$C_6$ alkynyl and $C_3$-$C_6$ cycloalkyl is independently optionally substituted by halogen, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl, $—OR^{13a}$, $—OC(O)R^{13a}$, $—OC(O)NR^{13a}R^{13a'}$, $—OS(O)R^{13a}$, $—OS(O)_2R^{13a}$, $—SR^{13a}$, $—SC(O)R^{13a}$, $—S(O)R^{13a}$, $—S(O)_2R^{13a}$, $—S(O)_2OR^{13a}$, $—S(O)NR^{13a}R^{13a'}$, $—S(O)_2NR^{13a}R^{13a'}$, $—OS(O)NR^{13a}R^{13a'}$, $—OS(O)_2NR^{13a}R^{13a'}$, $—NR^{13a}R^{13a'}$, $—NR^{13a}C(O)NR^{14a}$, $—NR^{13a}C(O)OR^{14a}$, $—NR^{13a}C(O)NR^{14a}R^{14a'}$, $—NR^{13a}S(O)R^{14a}$, $—NR^{13a}S(O)_2R^{14a}$, $—NR^{13a}S(O)NR^{13a}R^{14a'}$, $—NR^{13a}S(O)_2NR^{14a}R^{14a'}$, $—P(O)(OR^{13a})_2$, $—C(O)R^{13a}$, $—C(O)OR^{13a}$ or $—C(O)NR^{13a}R^{13a'}$;

$R^{2a}$, $R^{4a}$ and $R^{12a}$ are each independently selected from the group consisting of H, $C_1$-$C_6$ alkyl, $C_2$-$C_6$ alkenyl, $C_2$-$C_6$ alkynyl;

$R^{5a}$ and $R^{6a}$ are each independently selected from the group consisting of H, halogen, $C_1$-$C_6$ alkyl, $C_2$-$C_6$ alkenyl, $C_2$-$C_6$ alkynyl, $—OR^{15a}$, $—SR^{15a}$ and $—NR^{15a}R^{15a'}$, wherein each hydrogen atom in $C_1$-$C_6$ alkyl, $C_2$-$C_6$ alkenyl and $C_2$-$C_6$ alkynyl is independently optionally substituted by halogen, $—OR^{16a}$, $—SR^{16a}$, $—NR^{16a}R^{16a'}$, $—C(O)R^{16a}$, $—C(O)OR^{16a}$ or $—CO(O)NR^{16a}R^{16a'}$; or $R^{5a}$ and $R^{6a}$ taken together with the carbon atom to which they are attached form a $—C(O)—$;

each $R^{7a}$, $R^{8a}$, $R^{9a}$, $R^{10a}$ and $R^{11a}$ is independently selected from the group consisting of H, halogen, $C_1$-$C_6$ alkyl, $C_2$-$C_6$ alkenyl, $C_2$-$C_6$ alkynyl, $—CN$, $—NO_2$, $—NCO$, $—OR^{17a}$, $—SR^{17a}$, $—S(O)_2OR^{17a}$, $—NR^{17a}R^{17a'}$, $—P(O)(OR^{17a})_2$, $—C(O)R^{17a}$, $—C(O)OR^{17a}$ and $—C(O)NR^{17a}R^{17a'}$, wherein each hydrogen atom in $C_1$-$C_6$ alkyl, $C_2$-$C_6$ alkenyl and $C_2$-$C_6$ alkynyl is independently optionally substituted by halogen, $—OR^{18a}$, $—SR^{18a}$, $—NR^{18a}R^{18a'}$, $—C(O)R^{18a}$, $—C(O)OR^{18a}$ or $—C(O)NR^{18a}R^{18a'}$;

each $R^{13a}$, $R^{13a'}$, $R^{14a}$, $R^{14a'}$, $R^{15a}$, $R^{15a'}$, $R^{16a}$, $R^{16a'}$, $R^{17a}$ and $R^{17a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl, wherein each hydrogen atom in $C_1$-$C_7$ alkyl, $C_2$-$C_7$ alkenyl, $C_2$-$C_7$ alkynyl, $C_3$-$C_6$ cycloalkyl, 3- to 7-membered heterocycloalkyl, $C_6$-$C_{10}$ aryl, or 5- to 7-membered heteroaryl is independently optionally substituted by halogen, $—OH$, $—SH$, $—NH_2$ or $—CO_2H$;

each $R^{18a}$ and $R^{18a'}$ is independently selected from the group consisting of H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl, 5- to 7-membered heteroaryl $—C(O)R^{19a}$, $—P(O)(OR^{19a})_2$, and $—S(O)_2OR^{19a}$, each $R^{19}$ is independently selected from H, $C_1$-$C_6$ alkyl, $C_2$-$C_6$ alkenyl, $C_2$-$C_6$ alkynyl, $C_3$-$C_6$ cycloalkyl, 3- to 7-membered heterocycloalkyl, $C_6$-$C_{10}$ aryl and 5- to 7-membered heteroaryl;

a is 1, 2 or 3; and

* represents a covalent bond to the rest of the conjugate.

In some embodiments, the therapeutic agent is of the formula

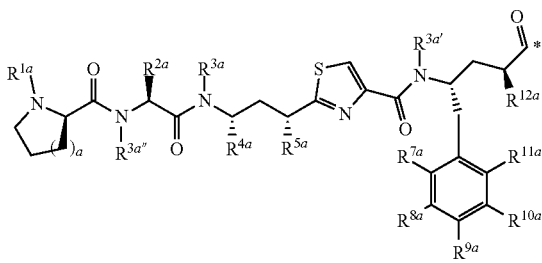

wherein $R^{1a}$, $R^{2a}$, $R^{3a}$, $R^{3a'}$, $R^{3a''}$, $R^{4a}$, $R^{5a}$, $R^{7a}$, $R^{8a}$, $R^{9a}$, $R^{10a}$, $R^{11a}$ and $R^{12a}$ are as described herein, and * represents a covalent bond to the rest of the conjugate.

In another embodiment, the therapeutic agent can be a naturally occurring tubulysin, or analog or derivative thereof, of the following general formula

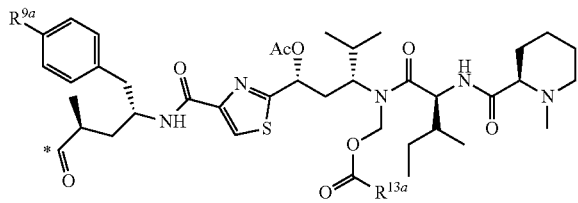

wherein $R^{9a}$ and $R^{13a}$ are as described herein, and * represents a covalent bond to the rest of the conjugate.

Conjugates of each of the foregoing tubulysins are described herein.

In some embodiments, the therapeutic agent can be a naturally occurring tubulysin of the following general formula

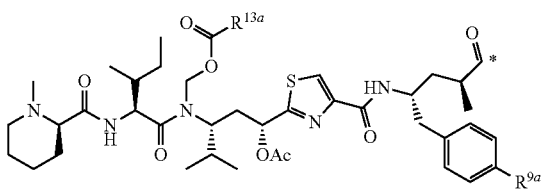

| Factor | $R^{13a}$ | $R^{9a}$ |
|---|---|---|
| A | $(CH_3)_2CHCH_2$ | OH |
| B | $CH_3(CH_2)_2$ | OH |
| C | $CH_3CH_2$ | OH |
| D | $(CH_3)_2CHCH_2$ | H |
| E | $CH_3(CH_2)_2$ | H |
| F | $CH_2CH_3$ | H |
| G | $(CH_3)_2C=CH$ | OH |
| H | $CH_3$ | H |
| I | $CH_3$ | OH | and * represents a covalent bond to the rest of the conjugate

Suitable molecules useful as imaging agents include, but are not limited to, dyes, such as rhodamine dyes and fluorescein dyes, PET imaging agents, or radiolabeled agents, and the like. Examples of rhodamine dyes include, but are not limited to, 5-carboxytetramethylrhodamine (5-TAMRA), rhodamine B, rhodamine 6G, TRITC, Texas Red, rhodamine 123, sulforhodamine 101, and the like. Examples of fluorescein dyes include but are not limited to fluorescein, 5-amino-fluorescein, 6-amino-fluorescein, fluorescein isocyanate (FITC), NHS-fluorescein, Oregon Green, Tokyo Green, Singapore Green, Philadelphia Green, and the like.

In some embodiments, a radiolabeled agent can be used in connection with the conjugate of the present disclosure. In some embodiments, the rhodamine dye or fluorescein dye can be isotopically labelled. Examples of isotopes suitable for inclusion in the conjugates include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulfur, such as $^{35}S$.

Certain isotopically-labelled conjugates, for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with positron emitting isotopes, such as $^{11}C$, $^{18}F$, and $^{13}N$, can be useful in Positron Emission Topography (PET) studies for examining substrate receptor occupancy. Isotopically-labeled conjugates can generally be prepared by conventional techniques known to those skilled in the art or by processes analogous to those described in the accompanying Examples using an appropriate isotopically-labeled reagents in place of the non-labeled reagent previously employed.

In some embodiments, the present disclosure provides methods for imaging a population of cell or tissue, either in vitro or in vivo. It will be appreciated that such in vitro methods can be carried out by any method known in the art. In some embodiments, in vitro imaging methods described herein can include a. contacting a population of cells with a conjugate as described herein that is suitable for imaging to provide the conjugate bound to cells expressing a CA IX protein, and b. visualizing the conjugate bound to cells by irradiation with light. It will be appreciated that visualizing the conjugate bound to cells by irradiation with light can include irradiation at an excitation wavelength and detection at an emission wavelength. Thus, in some embodiments, in vitro imaging methods described herein can include a. contacting a population of cells with a conjugate as described herein that is suitable for imaging to provide the conjugate bound to cells expressing a CA IX protein, b. irradiating the conjugate bound to cells expressing a CA IX protein with an excitation wavelength light, and c. detecting light emitted from the cancer cells at an emission wavelength.

In some embodiments, tissues, such as cancerous tumors, can be imaged according to the methods described herein. For example, in some embodiments, in vivo imaging methods described herein can include a. administering to the patient a conjugate as described herein that is suitable for imaging; or a pharmaceutically acceptable salt thereof, to provide the conjugate bound to cells expressing a CA IX protein; and b. visualizing the conjugate bound to cells expressing a CA IX protein by irradiation with light. It will be appreciated that visualizing the conjugate bound to cells by irradiation with light can include irradiation at an excitation wavelength and detection at an emission wavelength. Thus, in some embodiments, in vivo imaging methods described herein can include a. administering to the patient a conjugate as described herein that is suitable for imaging; or a pharmaceutically acceptable salt thereof, to provide the conjugate bound to cells expressing a CA IX protein; b. irradiating the conjugate bound to cells expressing a CA IX protein with an excitation wavelength light; and c. detecting light emitted from the cancer cells at an emission wavelength. It will be appreciated that visualizing the conjugate bound to cells by irradiation with light can be carried out using any known imaging techniques (diagnostic or otherwise) or instrumentation known in the art.

In one embodiment, the methods described herein can be used for both human clinical medicine and veterinary applications as a "subject". Thus, a "subject" can be administered the conjugates described herein, and can be human ("patient") or, in the case of veterinary applications, can be a laboratory, agricultural, domestic, or wild animal. In one aspect, the subject can be a human patient, a laboratory animal such as a rodent (e.g., mice, rats, hamsters, etc.), a rabbit, a monkey, a chimpanzee, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

In various embodiments, the cancers described herein can be a cancer cell population that is tumorigenic, including benign tumors and malignant tumors, or the cancer can be non-tumorigenic. The cancer can arise spontaneously or by such processes as mutations present in the germline of the patient or somatic mutations, or the cancer can be chemically-, virally-, or radiation-induced. Cancers applicable to the invention described herein include, but are not limited to, a carcinoma, a sarcoma, a lymphoma, a melanoma, a mesothelioma, a nasopharyngeal carcinoma, a leukemia, an adenocarcinoma, and a myeloma.

In some aspects the cancers can be lung cancer, bone cancer, pancreatic cancer, skin cancer, cancer of the head, cancer of the neck, cutaneous melanoma, intraocular melanoma uterine cancer, ovarian cancer, endometrial cancer, leiomyosarcoma, rectal cancer, stomach cancer, colon cancer, breast cancer, triple negative breast cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, non-small cell lung cancer, small cell lung cancer, cancer of the adrenal gland, sarcoma of soft tissue, cancer of the urethra, cancer of the penis, prostate cancer, chronic leukemia, acute leukemia, lymphocytic lymphomas, pleural mesothelioma, cancer of the bladder, Burkitt's lymphoma, cancer of the ureter, cancer of the kidney, renal cell carcinoma, carcinoma of the renal pelvis, neoplasms of the central nervous system (CNS), primary CNS lymphoma, spinal axis tumors, brain stem glioma, pituitary adenoma, cholangiocarcinoma, Hurthle cell thyroid cancer or adenocarcinoma of the gastroesophageal junction.

In other embodiments of the methods described herein, pharmaceutically acceptable salts of the conjugates described herein are provided. Pharmaceutically acceptable salts of conjugates described herein include acid addition and base salts thereof.

Suitable acid addition salts are formed from acids which form non-toxic salts. Illustrative examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts of the conjugates described herein are formed from bases which form non-toxic salts. Illustrative examples include the arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulphate and hemicalcium salts.

In one embodiment, the conjugates described herein may be administered as a formulation in association with one or more pharmaceutically acceptable carriers. The carriers can be excipients. The choice of carrier will to a large extent depend on factors such as the particular mode of administration, the effect of the carrier on solubility and stability, and the nature of the dosage form. Pharmaceutical compositions suitable for the delivery of conjugates as described herein and methods for their preparation will be readily apparent to those skilled in the art. Such compositions and methods for their preparation may be found, for example, in Remington: The Science & Practice of Pharmacy, 21th Edition (Lippincott Williams & Wilkins, 2005), incorporated herein by reference.

In one illustrative aspect, a pharmaceutically acceptable carrier includes any and all solvents, dispersion media, coatings, antibacterial and antifungal agents, isotonic and absorption delaying agents, and the like, and combinations thereof, that are physiologically compatible. In some embodiments, the carrier is suitable for parenteral administration. Pharmaceutically acceptable carriers include sterile aqueous solutions or dispersions and sterile powders for the extemporaneous preparation of sterile injectable solutions or dispersions. Supplementary active compounds can also be incorporated into compositions of the invention.

In various embodiments, liquid formulations may include suspensions and solutions. Such formulations may comprise a carrier, for example, water, ethanol, polyethylene glycol, propylene glycol, methylcellulose or a suitable oil, and one or more emulsifying agents and/or suspending agents. Liquid formulations may also be prepared by the reconstitution of a solid.

In one embodiment, an aqueous suspension may contain the active materials in admixture with appropriate excipients. Such excipients are suspending agents, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally-occurring phosphatide, for example, lecithin; a condensation product of an alkylene oxide with a fatty acid, for example, polyoxyethylene stearate; a condensation product of ethylene oxide with a long chain aliphatic alcohol, for example, heptadecaethyleneoxycetanol; a condensation product of ethylene oxide with a partial ester derived from fatty acids and a hexitol such as polyoxyethylene sorbitol monooleate; or a condensation product of ethylene oxide with a partial ester derived from fatty acids and hexitol anhydrides, for example, polyoxyethylene sorbitan monooleate. The aqueous suspensions may also contain one or more preservatives, for example, ascorbic acid, ethyl, n-propyl, or p-hydroxybenzoate; or one or more coloring agents.

In one illustrative embodiment, dispersible powders and granules suitable for preparation of an aqueous suspension by the addition of water provide the active ingredient in admixture with a dispersing or wetting agent, suspending agent and one or more preservatives. Additional excipients, for example, coloring agents, may also be present.

Suitable emulsifying agents may be naturally-occurring gums, for example, gum acacia or gum tragacanth; naturally-occurring phosphatides, for example, soybean lecithin; and esters including partial esters derived from fatty acids and hexitol anhydrides, for example, sorbitan mono-oleate, and condensation products of the said partial esters with ethylene oxide, for example, polyoxyethylene sorbitan monooleate.

In other embodiments, isotonic agents, for example, sugars, polyalcohols such as mannitol, sorbitol, or sodium chloride can be included in the composition. Prolonged absorption of injectable compositions can be brought about by including in the composition an agent which delays absorption, for example, monostearate salts and gelatin.

Illustrative formats for oral administration include tablets, capsules, elixirs, syrups, and the like.

Depending upon the cancer type as described herein, the route of administration and/or whether the conjugates are administered locally or systemically, a wide range of permissible dosages are contemplated herein, including doses falling in the range from about 1 µg/kg to about 1 g/kg. The dosages may be single or divided, and may administered according to a wide variety of protocols, including q.d., b.i.d., t.i.d., or even every other day, biweekly (b.i.w.), once a week, once a month, once a quarter, and the like. In each of these cases it is understood that the therapeutically effective amounts described herein correspond to the instance of administration, or alternatively to the total daily, weekly, month, or quarterly dose, as determined by the dosing protocol.

In one aspect, a conjugate as described herein may be administered directly into the blood stream, into muscle, or into an internal organ. Suitable routes for such parenteral administration include intravenous, intraarterial, intraperitoneal, intrathecal, epidural, intracerebroventricular, intraurethral, intrasternal, intracranial, intratumoral, intramuscular and subcutaneous delivery. Suitable means for parenteral administration include needle (including microneedle) injectors, needle-free injectors and infusion techniques.

In one illustrative aspect, parenteral formulations are typically aqueous solutions which may contain carriers or excipients such as salts, carbohydrates and buffering agents (preferably at a pH of from 3 to 9), but, for some applications, they may be more suitably formulated as a sterile non-aqueous solution or as a dried form to be used in conjunction with a suitable vehicle such as sterile, pyrogen-free water. In other embodiments, any of the liquid formulations described herein may be adapted for parenteral administration of the conjugates described herein. The preparation of parenteral formulations under sterile conditions, for example, by lyophilization under sterile conditions, may be readily be accomplished using standard pharmaceutical techniques well known to those skilled in the art. In one embodiment, the solubility of a conjugate as described herein used in the preparation of a parenteral formulation may be increased by the use of appropriate formulation techniques, such as the incorporation of solubility-enhancing agents.

In various embodiments, formulations for parenteral administration may be formulated for immediate and/or modified release. In one illustrative aspect, active agents of the invention (i.e., the conjugates described herein) may be administered in a time release formulation, for example in a composition which includes a slow release polymer. The active agents can be prepared with carriers that will protect the conjugate against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PGLA). Methods for the preparation of such formulations are generally known to those skilled in the art. In another embodiment, the conjugates described herein or compositions comprising the conjugates may be continuously administered, where appropriate.

In one embodiment, a kit is provided. If a combination of active conjugates as described herein is to be administered, two or more pharmaceutical compositions may be combined in the form of a kit suitable for sequential administration or co-administration of the compositions. Such a kit comprises two or more separate pharmaceutical compositions, at least one of which contains a conjugate described herein, and means for separately retaining the compositions, such as a container, divided bottle, or divided foil packet. In another embodiment, compositions comprising one or more conjugates as described herein, in containers having labels that provide instructions for use of the conjugates as described herein for patient selection and/or treatment are provided.

In one embodiment, sterile injectable solutions can be prepared by incorporating the active agent in the required amount in an appropriate solvent with one or a combination of ingredients described above, as required, followed by filtered sterilization. Typically, dispersions are prepared by incorporating the conjugate into a sterile vehicle which contains a dispersion medium and any additional ingredients of those described above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof, or the ingredients may be sterile-filtered together.

The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. In one embodiment, the proper fluidity can be maintained, for example, by the use of a coating such as lecithin, by the maintenance of the required particle size in the case of dispersion and by the use of surfactants.

Any effective regimen for administering the conjugates described herein can be used. For example, conjugates described herein can be administered as single doses, or the doses can be divided and administered as a multiple-dose daily regimen. Further, a staggered regimen, for example, one to five days per week can be used as an alternative to daily treatment, and for the purpose of the methods described herein, such intermittent or staggered daily regimen is considered to be equivalent to every day treatment and is contemplated. In one illustrative embodiment the patient is treated with multiple injections of a conjugate described herein to treat the cancer. In one embodiment, the patient is injected multiple times (preferably about 2 up to about 50 times) with a conjugate described herein, for example, at 12-72 hour intervals or at 48-72 hour intervals. Additional injections of a conjugate described herein can be administered to the patient at an interval of days or months after the initial injections(s) and the additional injections can prevent recurrence of the cancer.

Any suitable course of therapy with the conjugates described herein can be used. In one embodiment, individual doses and dosage regimens are selected to provide a total dose administered during a month of about 15 mg. In one illustrative example, a conjugate described herein is administered in a single daily dose administered five days a week, in weeks 1, 2, and 3 of each 4 week cycle, with no dose administered in week 4. In an alternative example, a conjugate described herein is administered in a single daily dose administered three days a week, of weeks 1, and 3 of each 4 week cycle, with no dose administered in weeks 2 and 4. In an alternative example, a conjugate described herein is administered biweekly on weeks 1 and 2, i.e. on days 1, 4, 8, 11, of a 3-week cycle. In an alternative example, a conjugate described herein is administered and once weekly on weeks 1 and 2, i.e. days 1 and 8 of a 3-week cycle.

The unitary daily dosage of the conjugates described herein can vary significantly depending on the patient condition, the cancer being treated, the route of administration of the conjugates described herein and tissue distribution, and the possibility of co-usage of other therapeutic treatments, such as radiation therapy or additional drugs in combination therapies. The effective amount to be administered to a patient is based on body surface area, mass, and physician assessment of patient condition. Therapeutically effective doses (also referred to herein as "therapeutically effective amount") can range, for example, from about 0.5 mg/m$^2$ to about 20.0 mg/m$^2$.

The conjugates described herein may contain one or more chiral centers, or may otherwise be capable of existing as multiple stereoisomers. Accordingly, it is to be understood that the present invention includes pure stereoisomers as well as mixtures of stereoisomers, such as enantiomers, diastereomers, and enantiomerically or diastereomerically enriched mixtures. The conjugates described herein may be capable of existing as geometric isomers. Accordingly, it is to be understood that the present invention includes pure geometric isomers or mixtures of geometric isomers.

It is appreciated that the conjugates described herein may exist in unsolvated forms as well as solvated forms, including hydrated forms. In general, the solvated forms are equivalent to unsolvated forms and are encompassed within the scope of the present invention. The conjugates described herein may exist in multiple crystalline or amorphous forms. In general, all physical forms are equivalent for the uses contemplated by the present invention and are intended to be within the scope of the present invention.

In another embodiment, compositions and/or dosage forms for administration of a conjugate described herein are prepared from a conjugate described herein with a purity of at least about 90%, or about 95%, or about 96%, or about 97%, or about 98%, or about 99%, or about 99.5%. In another embodiment, compositions and or dosage forms for administration of a conjugate described herein are prepared from a conjugate described herein with a purity of at least 90%, or at least 95%, or at least 96%, or at least 97%, or at least 98%, or at least 99%, or at least 99.5%.

EXAMPLES

Materials.

Protected amino acids were purchased from Chem-Impex International (Chicago, Ill.). H-Cys (Trt)-2-Cl-Trt resin was obtained from Novabiochem (San Diego, Calif.). Tubulysin B and its activated derivatives were a kind gift from Endocyte Inc. (West Lafayette, Ind.). 2-(1H-7-Azabenzotriazole-1-yl)-1,1,3,3-tetramethyl uronium hexafluorophosphate methanaminium (HATU) was obtained from Genscript Inc. (Piscataway, N.J.). Sulfuric acid, methanol, DMSO, DMF, TFA, isopropyl alcohol, $NH_2$-$PEG_{12}$-COOH-tBu, diisopropylethylamine (DIPEA), piperidine, $CF_3COOH$, $CH_2Cl_2$, $K_2CO_3$, tyramine and all other chemical reagents were purchased from Sigma Aldrich. Pure coat Amine 24-well microtiter plates were purchased from BD Biosciences (San Jose, Calif.). All other cell culture reagents, syringes and disposable items were purchased from VWR (Chicago, Ill.).

CHEMISTRY EXAMPLES

Example 1: Preparation of EC2665

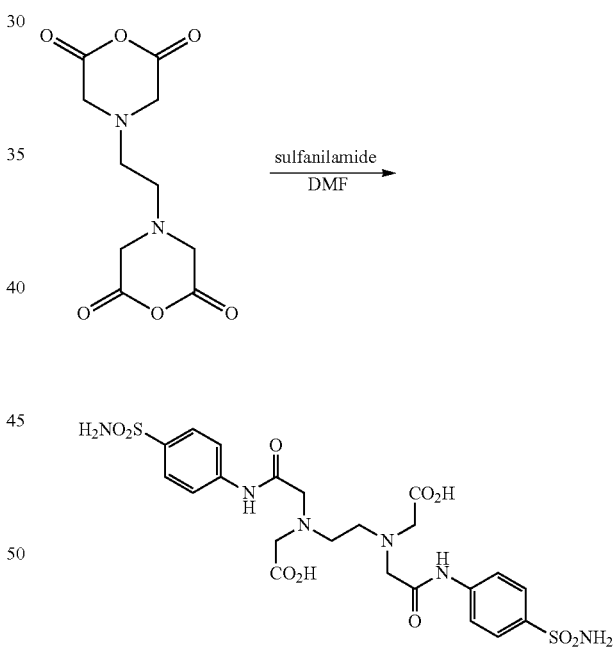

EC2665 was prepared according to the procedure described in J. Med. Chem (2002), 45, 1466. Briefly, to a solution of sulfanilamide (1.55 g, 9.0 mmol) in DMF (30 mL) was added EDTA-dianhydride (1.15 g, 4.5 mmol). The solution was allowed to stir at room temperature overnight. The reaction was then poured into dichloromethane (300 mL). The precipitate was recovered by Buchner funnel filtration. The resulting filter cake was washed with dichloromethane and acetone. After drying under vacuum, EC2665 was recovered as a white solid (2 g, 73% yield). ESI-MS [M+H]+=601.5.

Example 2: Preparation of EC2667

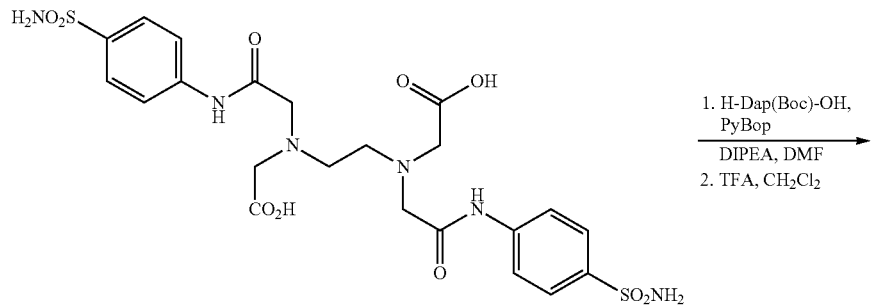

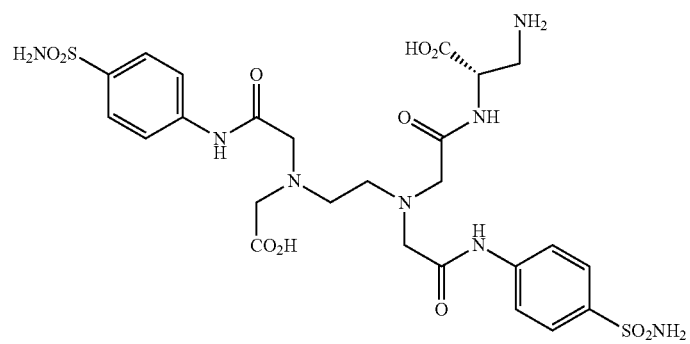

EC2665 (600 mg, 1.0 mmol) was dissolved in DMF (4 mL). To this solution was added DIPEA (504 μL, 3 eq.), followed by PyBop (520 mg, 1 eq.), dropwise over 5 minutes. The reaction was allowed to stir for 10 minutes, and then H-Dap(Boc)-OH (204 mg, 1 eq.) was added. The reaction was allowed to stir at room temperature for 2 hours. The reaction was poured into Et$_2$O and the solid recovered by centrifugation. The solid was re-dissolved in DMSO (6 mL) and loaded onto a Biotage C18 column (50 mM NH$_4$HCO$_3$ (pH=7)/ACN eluents) and purified. The pure product fractions were combined and lyophilized. Mixed fractions were re-purified by Biotage C18 column (0.1% TFA/ACN). Pure product fractions were combined and lyophilized. The resulting residue was treated with TFA/CH$_2$Cl$_2$ (1 mL, 6:4) for 25 minutes. The solvent was then removed under reduced pressure and the residue was purified by loading the material onto a Biotage C18 column (0.1% TFA/ACN). The clean fractions were combined and lyophilized to give EC2667 (89 mg, 13% yield) as a white powder. ESI-MS [M+H]$^+$=687.6. $^1$H NMR (500 MHz, DMSO-D$_6$/D$_2$O): δ 7.71 (m, 8H), 4.55 (dd, 1H), 3.63-3.77 (m, 7H), 3.24 (dd, 1H), 2.95-3.06 (m 6H).

Example 3: Preparation of EC2676

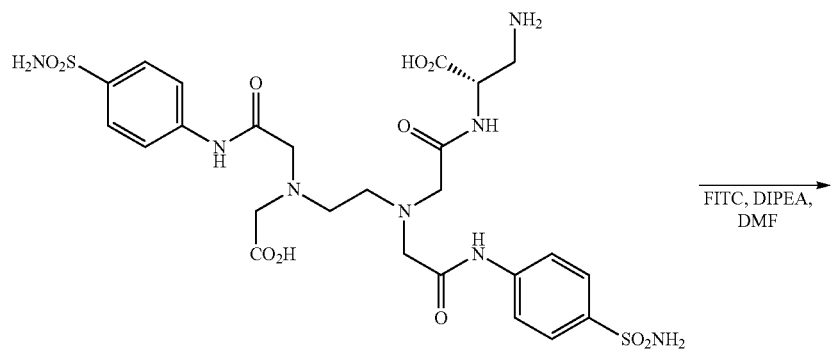

-continued

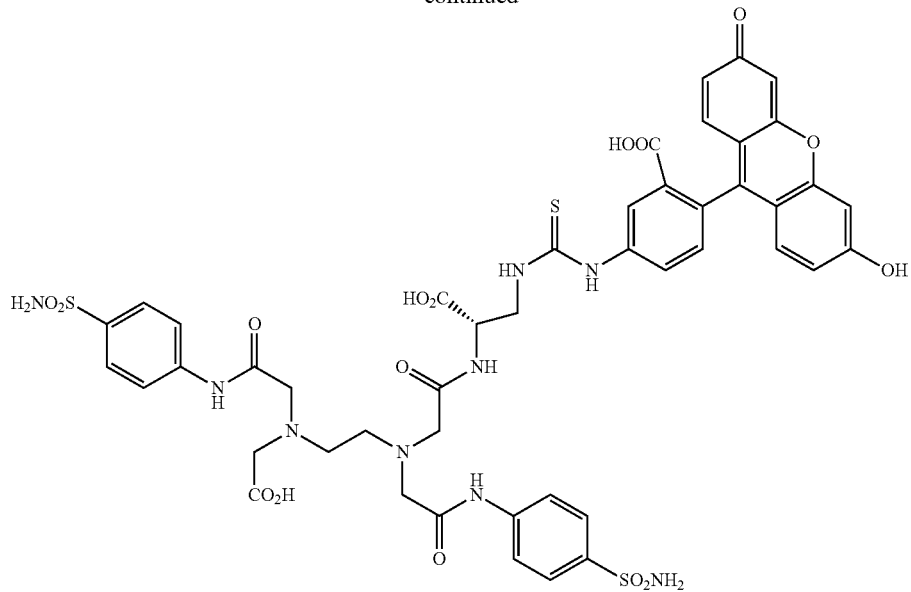

EC2667 (20 mg, 0.0291 mmol) was dissolved in DMF (600 μL) and DIPEA (26 μL, 5 eq.) was added. FITC (11.4 mg, 1 eq.) was then added in four portions over 4 minutes. After stirring for 25 minutes, the reaction was diluted with water and loaded onto a Biotage C18 column (50 mM $NH_4HCO_3$ (pH=7)/ACN eluents) and purified. Clean fractions were combined and lyophilized to give EC2676 (10 mg, 32% yield) as a yellow/orange solid. ESI-MS $[M+H]^+=1076.3$. Representative peaks $^1$H NMR (500 MHz, DMSO-$D_6$/$D_2O$): δ 8.55 (bs, 1H), 7.95-7.58 (m, 8H), 7.03 (bd, 1H), 6.63 (s, 2H), 6.58 (m, 4H), 4.33 (bs, 1H), 4.17 (bs, 1H).

Example 4: Preparation of EC2677

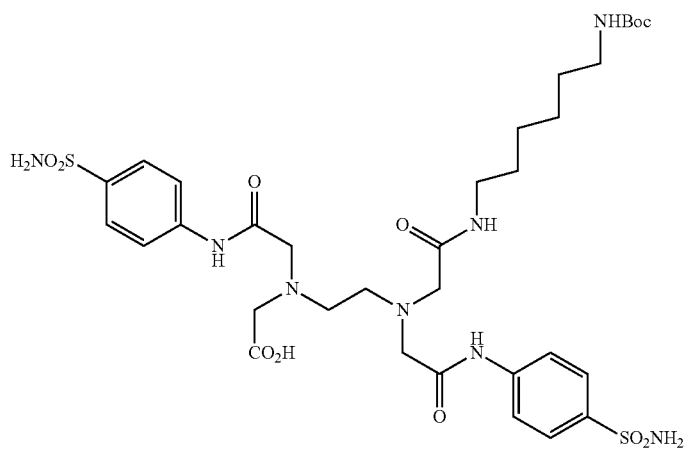

EC2665 (150 mg, 0.249 mmol) was dissolved in DMF. To this solution was added N-Boc-1,6-diaminohexane (54 mg, 1 eq.) and DIPEA (126 μL, 3 eq.). Finally, PyBop (130 mg, 1 eq.) was then added and the reaction was allowed to stir for 1 hr. The reaction was diluted with water and loaded directly onto a Biotage C18 column and purified using 0.1% TFA/ACN. After lyophilization of the combined pure fractions, EC2677 was recovered as a white powder (62 mg, 31% yield). ESI-MS [M+H]$^+$=799.6. Representative peaks $^1$H NMR (500 MHz, DMSO-D$_6$/D$_2$O): δ 7.82-7.68 (m, 8H), 3.39 (d, 4H), 3.23 (d, 4H), 2.99 (bs, 2H), 2.83-2.63 (m, 6H), 1.36 (s, 9H), 1.36-1.05 (m, 8H).

Example 5: Preparation of EC2680

EC2677 (15 mg, 0.0188 mmol) was treated with TFA/CH$_2$Cl$_2$ (1 mL, 6:4). The reaction was stirred for 30 min. The solvents were removed under reduced pressure and the residue was dried under vacuum for 2 hr. The residue was then re-dissolved in DMF (500 μL) and DIPEA (16 μL, 5 eq.) was then added. FITC (7.3 mg, 1 eq.) was then added in 4 portions over 4 minutes. The reaction was allowed to stir for an additional 4 minutes. The reaction was diluted with water and purified by Biotage C18 column (50 mM NH$_4$HCO$_3$ (pH=7)/ACN) to give EC2680 (6 mg, 29%) as a yellow/orange powder. ESI-MS [M+H]$^+$=1088.4 Representative peaks $^1$H NMR (500 MHz, DMSO-D$_6$/D$_2$O): δ 8.43 (bs, 1H), 7.83 (d, 1H), 7.8-7.63 (m, 10H), 7.05 (d, 1H), 6.63 (s, 2H), 6.56 (dd, 4H).

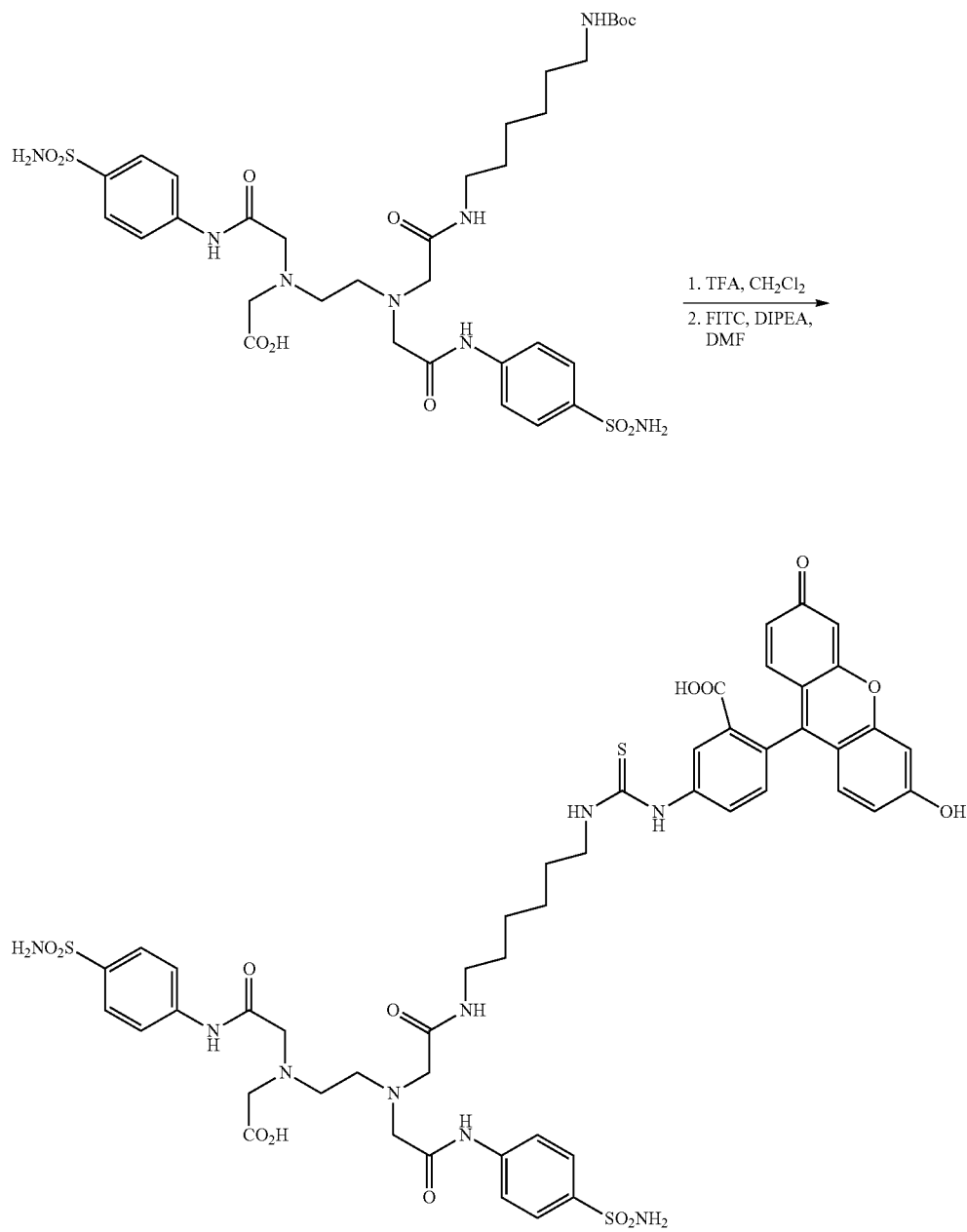 [SMILES: CC(C)(C)OC(=O)NCCCCCCNC(=O)CN(CCN(CC(=O)O)CC(=O)Nc1ccc(S(N)(=O)=O)cc1)CC(=O)Nc1ccc(S(N)(=O)=O)cc1 ; NS(=O)(=O)c1ccc(NC(=O)CN(CCN(CC(=O)NCCCCCCNC(=S)Nc2ccc(-c3c4ccc(=O)cc-4oc4cc(O)ccc34)c(C(=O)O)c2)CC(=O)Nc2ccc(S(N)(=O)=O)cc2)CC(=O)O)cc1]

Example 6: Preparation of EC2710

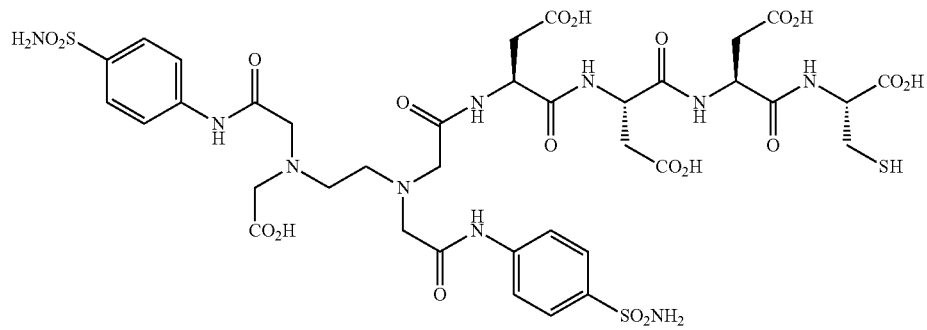 [SMILES: NS(=O)(=O)c1ccc(NC(=O)CN(CCN(CC(=O)Nc2ccc(S(N)(=O)=O)cc2)CC(=O)N[C@@H](CC(=O)O)C(=O)N[C@@H](CC(=O)O)C(=O)N[C@@H](CC(=O)O)C(=O)N[C@@H](CS)C(=O)O)CC(=O)O)cc1]

Peptidic spacer EC2710 was synthesized utilizing standard Fmoc-solid phase peptide synthesis techniques in a peptide synthesis vessel. H-Cys(Trt)-2-Cl-Trt-resin (1.5 g, 0.658 mmol/g, 1 mmol) was treated with Fmoc-Asp(Ot-Bu)-OH (824 mg, 2 eq.), PyBop (1.04 g, 2 eq.), and DIPEA (695 µL, 4 eq.) in DMF (~10 mL) for 1 hr. After washing with DMF and IPA, the Fmoc protecting group was removed with 20% piperidine in DMF (2×20 minutes). After washing again with DMF and IPA, the above sequence was repeated twice more to add two more Asp acid residues to the peptide. At this point, the partially completed on-resin peptide was dried under vacuum. 1.95 g of the resin (assumed 1 mmol) was recovered.

A portion of this resin (0.540 g, 0.277 mmol) was loaded into a peptide synthesis vessel, and the Fmoc protecting group was removed using the standard 20% piperidine in DMF (2×20 min) solution. After washing with DMF and IPA, EC2665 (250 mg, 0.42 mmol), PyBop (173 mg, 1.2 eq.) and DIPEA (193 µL, 4 eq.) were then added. The reaction was allowed to run for 1 hr. After removal of the solvent and washing with DMF and IPA, the peptide was cleaved from the resin using a TFA/$H_2O$/TIPS/DTT (92.5:2.5:2.5:2.5) cleavage solution. The peptide was precipitated using $Et_2O$ and the precipitate was recovered via centrifugation. The crude material was redissolved in DMSO and purified by Biotage C18 column (0.1% TFA/ACN) to give EC2710 (20 mg, 7% yield). ESI-MS $[M+H]^+$=1049.5. Representative peaks $^1$H NMR (500 MHz, DMSO-$D_6$/$D_2O$): δ 7.7 (s, 8H), 4.58 (dd, 1H), 4.55 (dd, 1H), 4.48 (dd, 1H), 4.38 (dd, 1H).

Example 7: Preparation of EC2711

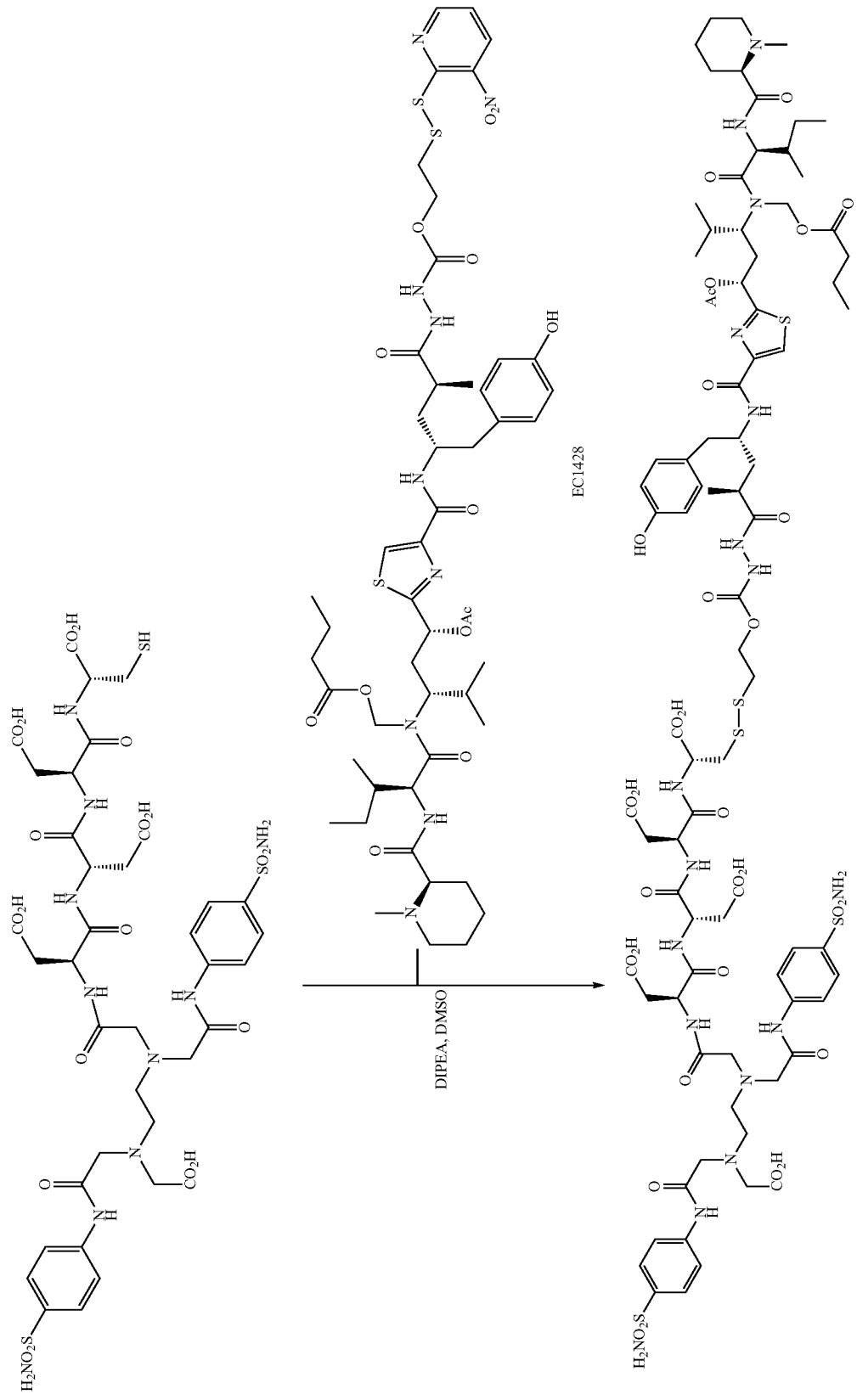

EC2710 (11.6 mg, 0.0111 mmol) was dissolved in DMSO (600 μL). To this solution was added DIPEA (19 μL, 10 eq.), followed by EC1428 (13 mg, 1.1 eq.). The reaction was stirred for 40 min. The reaction was loaded onto a Biotage C18 column (50 mM $NH_4HCO_3$ (pH=7)/ACN) and purified. After lyophilization, EC2711 (9 mg, 41% yield) was obtained as a white powder. ESI-MS $[M+H]^+=1995.2$. Representative peaks $^1H$ NMR (500 MHz, DMSO-$D_6$/$D_2O$): δ 8.17 (s, 1H), 7.83 (d, 1H), 7.78 (dd, 3H), 7.7 (dd, 4H), 6.96 (d, 2H), 6.59 (d, 2H), 6.18 (bd, 1H), 5.68 (d, 1H), 5.22 (d, 1H), 4.58 (dd, 1H), 4.48 (m, 2H), 4.4 (d, 1H).

Example 8: Preparation of EC2760

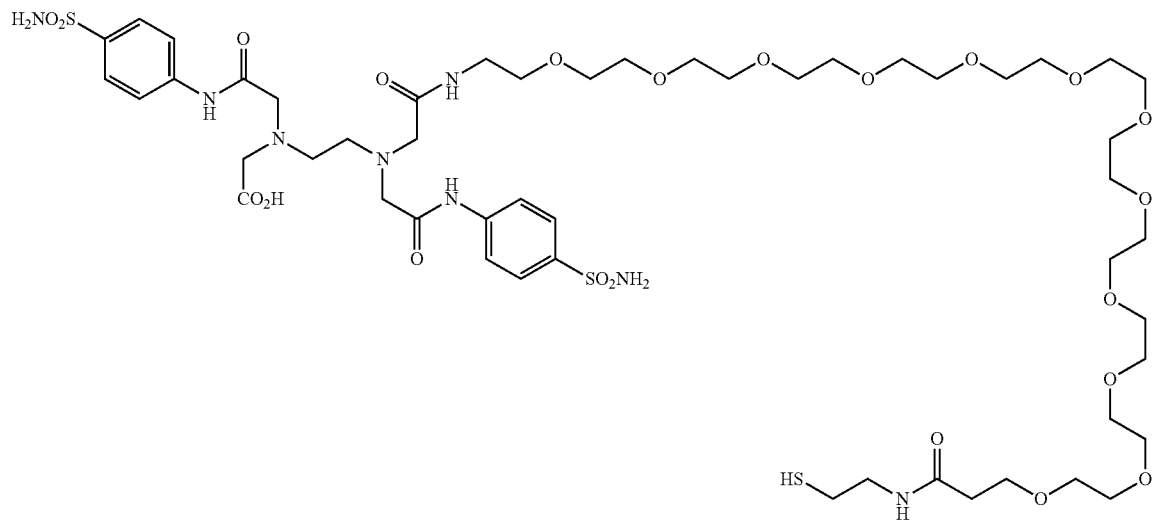 [SMILES: NS(=O)(=O)c1ccc(NC(=O)CN(CCN(CC(=O)NCCOCCOCCOCCOCCOCCOCCOCCOCCOCCOCCOCCOCCC(=O)NCCS)CC(=O)Nc2ccc(S(N)(=O)=O)cc2)CC(=O)O)cc1]

Followed standard Fmoc-solid phase peptide synthesis coupling techniques in a peptide synthesis vessel (see description for EC2710). Fmoc-cysteamine-SASRIN resin (663 mg, 0.470 mmol) was loaded into the peptide synthesis vessel. After removal of the Fmoc protecting group by 20% piperidine in DMF, the resin was treated with Fmoc-NH-Peg$_{12}$-acid (513 mg, 1.3 eq.), PyBop (318 mg, 1.3 eq.), and DIPEA (327 μL, 4 eq.). The reaction was allowed to agitate under argon bubbling overnight. After washing and Fmoc removal, the resin was treated with EC2665 (392 mg, 1.4 eq.), PyBop (293 mg, 1.2 eq.), and DIPEA (326 μL, 4 eq.). The reaction was allowed to agitate under argon bubbling for 1 hour. The resin was cleaved with TFA/$H_2O$/TIPS (94:4:2).

The cleavage solution was treated with $Et_2O$ to induce precipitation and the precipitate was recovered via centrifugation. The crude product was dissolved in DMSO and loaded onto a C18 Biotage column (0.1% TFA/ACN). After freeze-drying, EC2760 (30 mg, 5% yield) was recovered as a white powder. ESI-MS $[M+H]^+=1260.4$. Representative peaks $^1H$ NMR (500 MHz, methanol-$d_4$): δ 7.78 (m, 8H), 4.08 (s, 2H), 3.98 (s, 2H), 3.92 (bs, 2H), 3.79 (bs, 2H), 3.71 (t, 2H), 2.6 (t, 2H), 2.44 (t, 2H).

Example 9: Preparation of EC2761

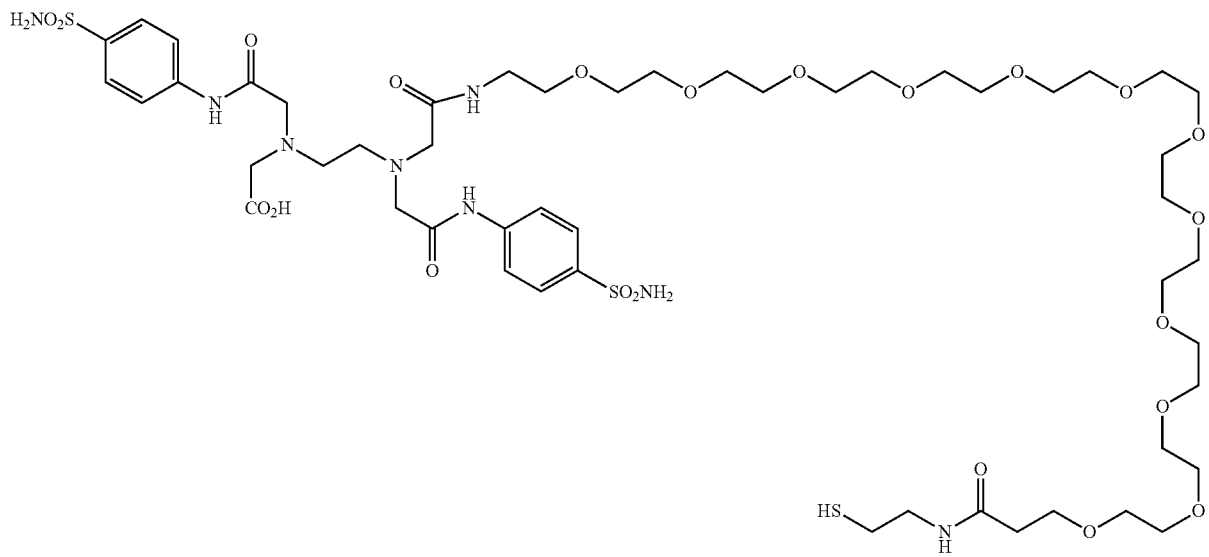

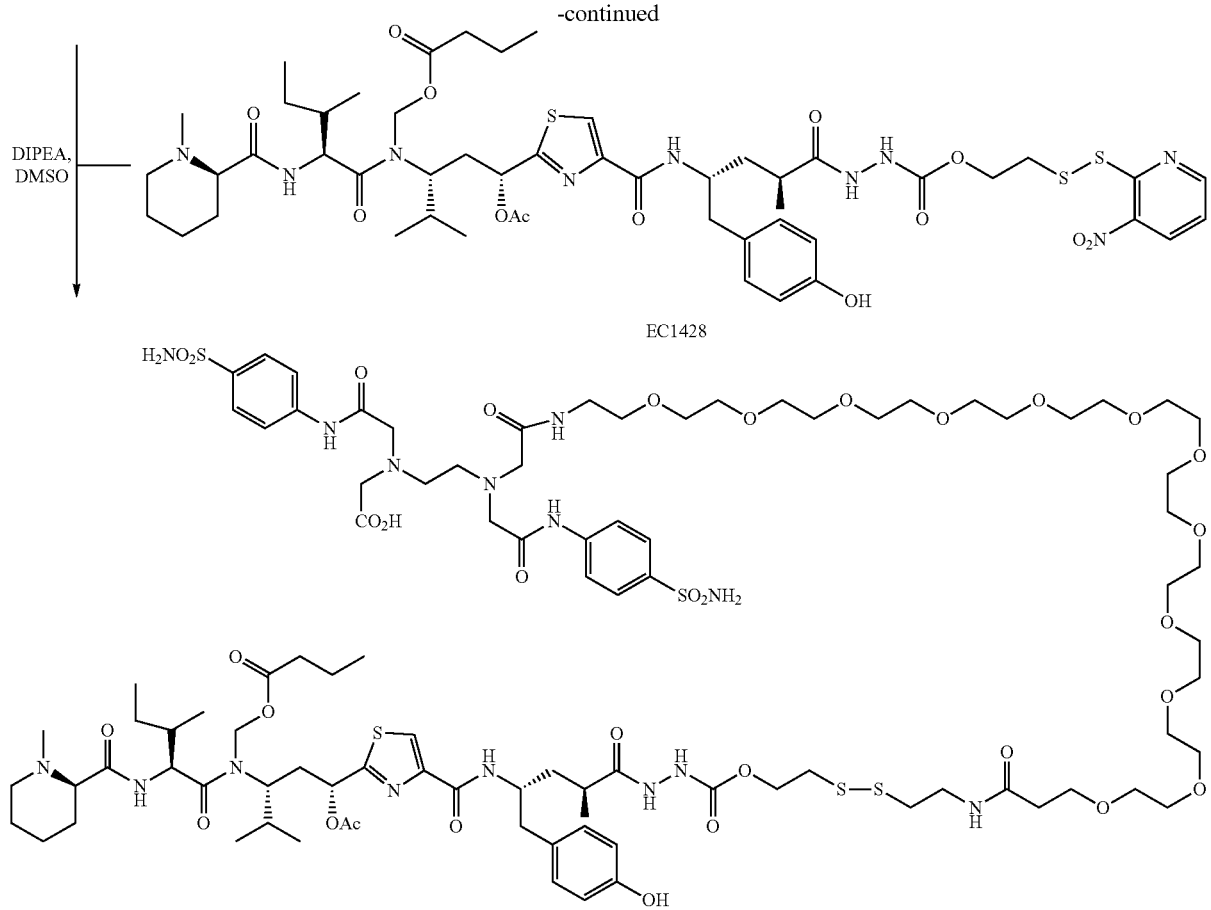

EC1428

To EC2760 (12.5 mg, 0.00992 mmol) in DMSO (500 uL) was added DIPEA (17 μL, 10 eq.), followed by EC1428 (12 mg, 1.1 eq.). The reaction was allowed to stir at room temperature for 30 min. The crude reaction was loaded onto a Biotage C18 column (50 mM $NH_4HCO_3$ (pH=7)/ACN). EC2761 (6 mg, 27% yield) was recovered as a white powder after freeze drying. ESI-MS $[M+2H]^{2+}$=1103.7. Representative peaks $^1$H NMR (500 MHz, DMSO-$D_6$/$D_2O$): δ 8.18 (s, 1H), 7.8 (d, 4H), 7.73 (dd, 4H), 6.95 (d, 2H), 6.59 (d, 2H), 6.2 (bd, 1H), 5.71 (d, 1H), 5.22 (d, 1H), 4.4 (d, 1H).

Example 10: Preparation of EC2762

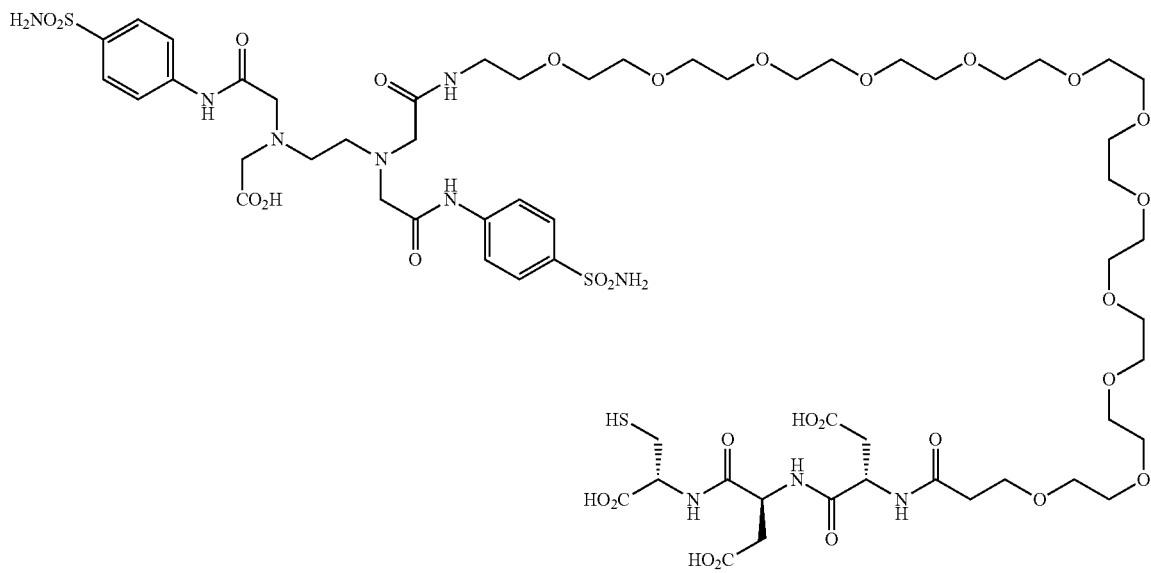 [SMILES: NS(=O)(=O)c1ccc(NC(=O)CN(CCN(CC(=O)NCCOCCOCCOCCOCCOCCOCCOCCOCCOCCOCCOCCOCCC(=O)N[C@@H](CC(=O)O)C(=O)N[C@@H](CC(=O)O)C(=O)N[C@@H](CS)C(=O)O)CC(=O)Nc2ccc(S(N)(=O)=O)cc2)CC(=O)O)cc1]

Followed standard Fmoc-solid phase peptide synthesis coupling techniques in a peptide synthesis vessel (see description for EC2710). H-Cys(Trt)-2-Cl-Trt-resin (0.760 g, 0.658 mmol/g, 0.5 mmol) was loaded into the solid phase vessel. Two cycles adding Fmoc-Asp(Ot-Bu)-OH (412 mg, 2 eq.) using the appropriate amounts of PyBop and DIPEA and a 1 hr coupling time were performed. Fmoc-NH-Peg$_{12}$-OH (546 mg, 1.3 eq.) was then added, along with PyBop (338 mg, 1.3 eq.) and DIPEA (260 µL, 3 eq.), and the reaction was allowed to agitate under argon bubbling overnight. The resin was then dried under vacuum to yield 1.2 g of partially loaded resin.

One half of the resin (600 mg, 0.25 mmol) was loaded into a peptide synthesis vessel and after Fmoc deprotection was treated with EC2665 (225 mg, 1.5 eq.), PyB op (163 mg, 1.5 eq.), and DIPEA (174 uL, 4 eq.). The reaction was agitated for 1 hr. After cleavage, precipitation, and purification via C18 Biotage column (0.1% TFA/ACN), EC2762 was recovered (68 mg, 17% yield). ESI-MS [M+H]$^+$=1534.5.

Example 11: Preparation of EC2763

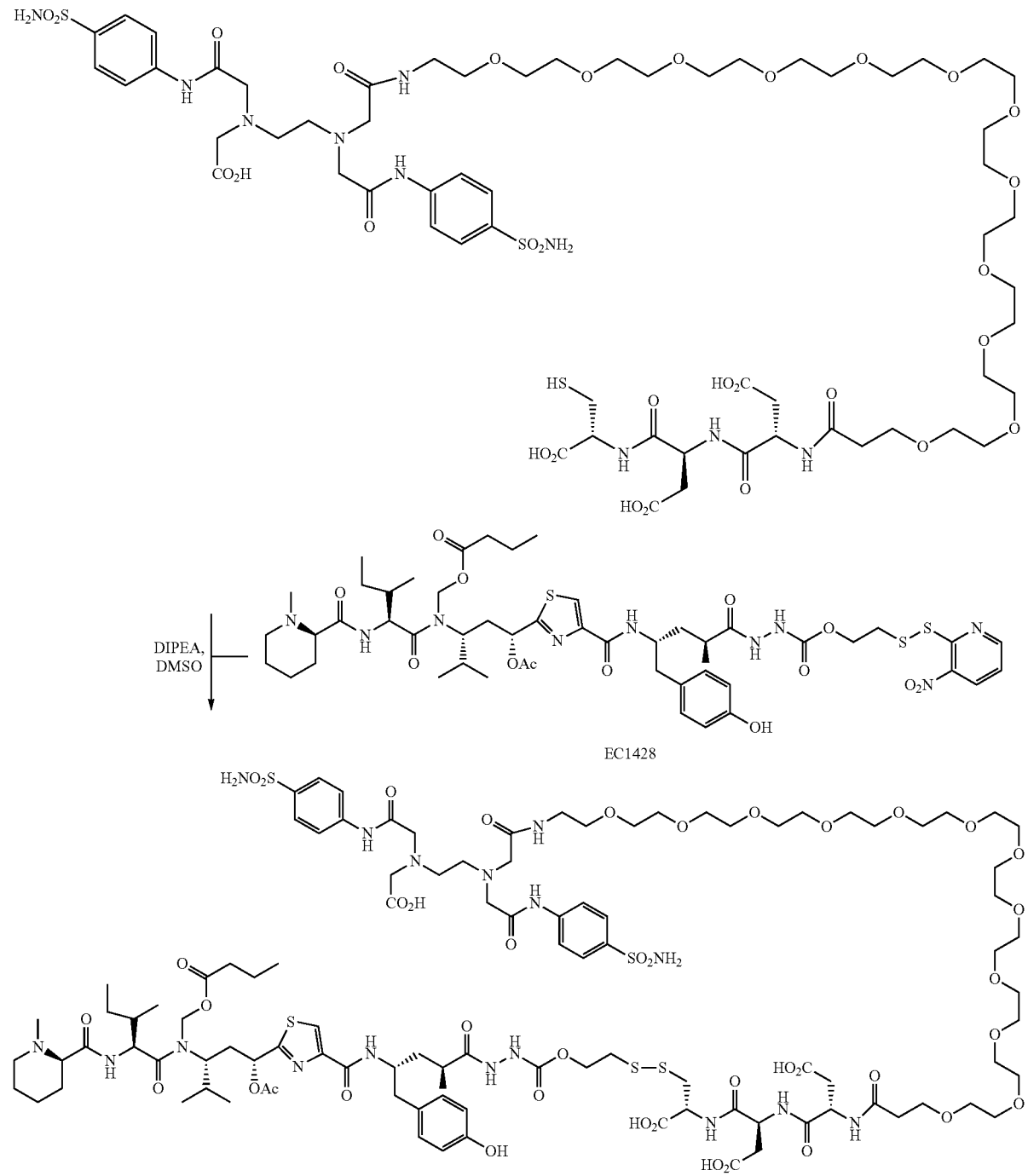

EC2762 (11.9 mg, 0.00776 mmol) was dissolved in DMSO (500 μL). To this solution was added DIPEA (13.5 μL, 10 eq.) and EC1428 (9.4 mg, 1.1 eq.). The reaction was allowed to stir for 30 minutes. The reaction was diluted with DMSO and loaded onto a preparative HPLC (Waters X-Bridge Prep C18 5 μM column 19×250 mm, 50 mM NH$_4$HCO$_3$ (pH=7)/ACN eluents). The fraction containing the target compound was freeze-dryed to give EC2763 (6 mg, 31% yield) as a white powder. ESI-MS [M+2H]$^{2+}$=1240.7. Representative peaks $^1$H NMR (500 MHz, DMSO-D$_6$/D$_2$O): δ 8.17 (s, 1H), 7.83 (d, 1H), 7.79 (d, 3H), 7.71 (d, 4H), 6.96 (d, 2H), 6.59 (d, 2H), 6.18 (bd, 1H), 5.71 (d, 1H), 5.22 (d, 1H), 4.55 (m, 2H), 4.4 (d, 1H).

Example 12: Preparation of EC2764

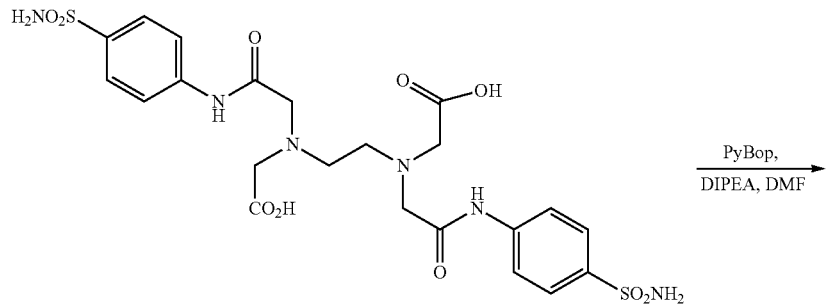

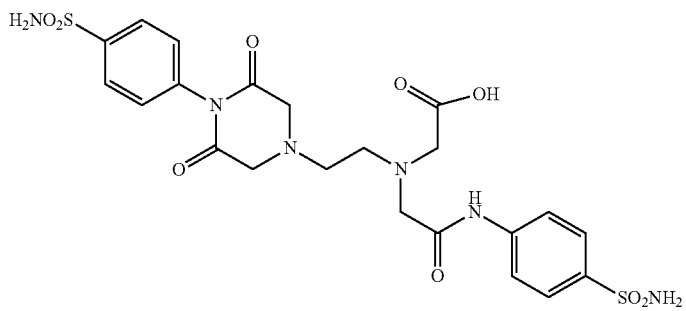

EC2665 (350 mg, 0.583 mmol) was dissolved in DMF (1 mL) and DIPEA (203 μL, 3.6 eq.) and finally, PyBop (303 mg, 1 eq.) was added. The reaction was allowed to stir for 1 hour. The reaction was diluted with water and loaded onto a Biotage C18 column (50 mM NH$_4$HCO$_3$ (pH=7)/ACN eluents). The pure product fractions were combined and the ACN was removed under reduced pressure. The resulting aqueous solution was loaded back onto a Biotage C18 column (H$_2$O/ACN eluents) to desalt the final product. After lyophilization, EC2764 (43 mg, 13% yield) was recovered as a white powder. ESI-MS [M+H]$^+$=583.4. Representative peaks $^1$H NMR (500 MHz, DMSO-D$_6$/D$_2$O): δ 7.85 (d, 2H), 7.77 (s, 4H), 7.25 (d, 2H), 2.99 (m, 1H), 2.91 (m, 2H), 2.69 (m, 2H).

Example 13: Preparation of EC2765

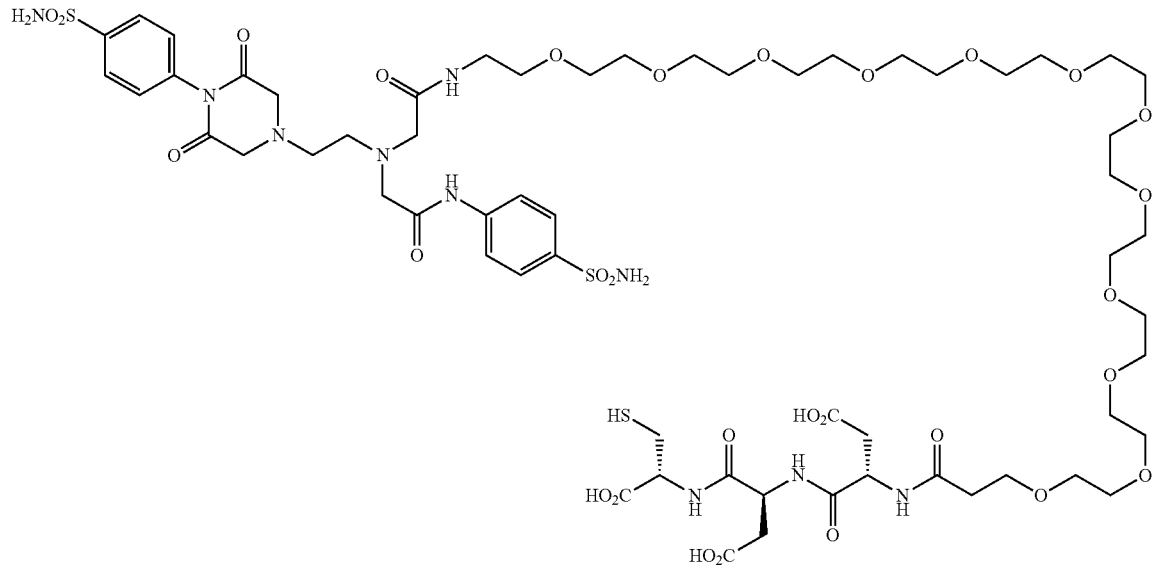 [SMILES: NS(=O)(=O)c1ccc(NC(=O)CN(CCN2CC(=O)N(c3ccc(S(N)(=O)=O)cc3)C(=O)C2)CC(=O)NCCOCCOCCOCCOCCOCCOCCOCCOCCOCCOCCOCCOCCC(=O)N[C@@H](CC(=O)O)C(=O)N[C@@H](CC(=O)O)C(=O)N[C@@H](CS)C(=O)O)cc1]

Partially loaded resin Fmoc-Peg$_{12}$-Asp-Asp-Cys-2-Cl-Trt-resin (155 mg, 0.25 mmol/600 mg, 0.0644 mmol) was treated with the standard 20% piperidine/DMF cleavage solution (2×20 min) in a peptide synthesis vessel. After washing with DMF and IPA, the deprotected resin was treated with EC2764 (45 mg, 1.2 eq.), PyBop (40 mg, 1.2 eq.), and DIPEA (54 µL, 5 eq.). The reaction was allowed to bubble under argon for 1 hour. After washing and drying, the peptide was cleaved from the resin using the standard TFA/H$_2$O/TIPS/DTT (92.5:2.5:2.5:2.5) cleavage solution. The peptide was precipitated with Et$_2$O and recovered by centrifugation. The crude peptide was re-dissolved in DMSO and loaded onto a Biotage C18 column (0.1% TFA/ACN) and purified to give EC2765 (24 mg, 25% yield) as a white powder after lyophilization. ESI-MS [M+H]$^+$=1515.7. Representative peaks $^1$H NMR (500 MHz, DMSO-D$_6$/D$_2$O): δ 7.87 (d, 2H), 7.77 (m, 4H), 7.32 (d, 2H), 4.55 (dd, 1H), 4.49 (dd, 1H), 4.39 (dd, 1H), 4.08 (bs, 2H), 3.91 (bs, 2H), 3.25 (t, 2H), 2.35 (t, 2H).

Example 14: Preparation of EC2766

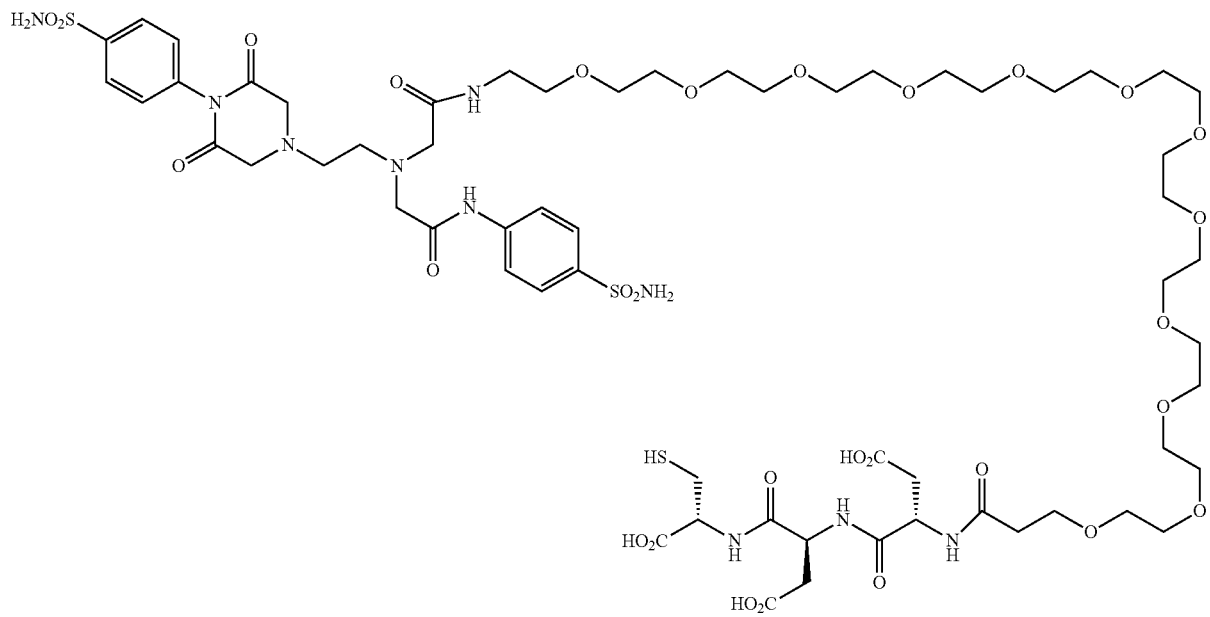

-continued

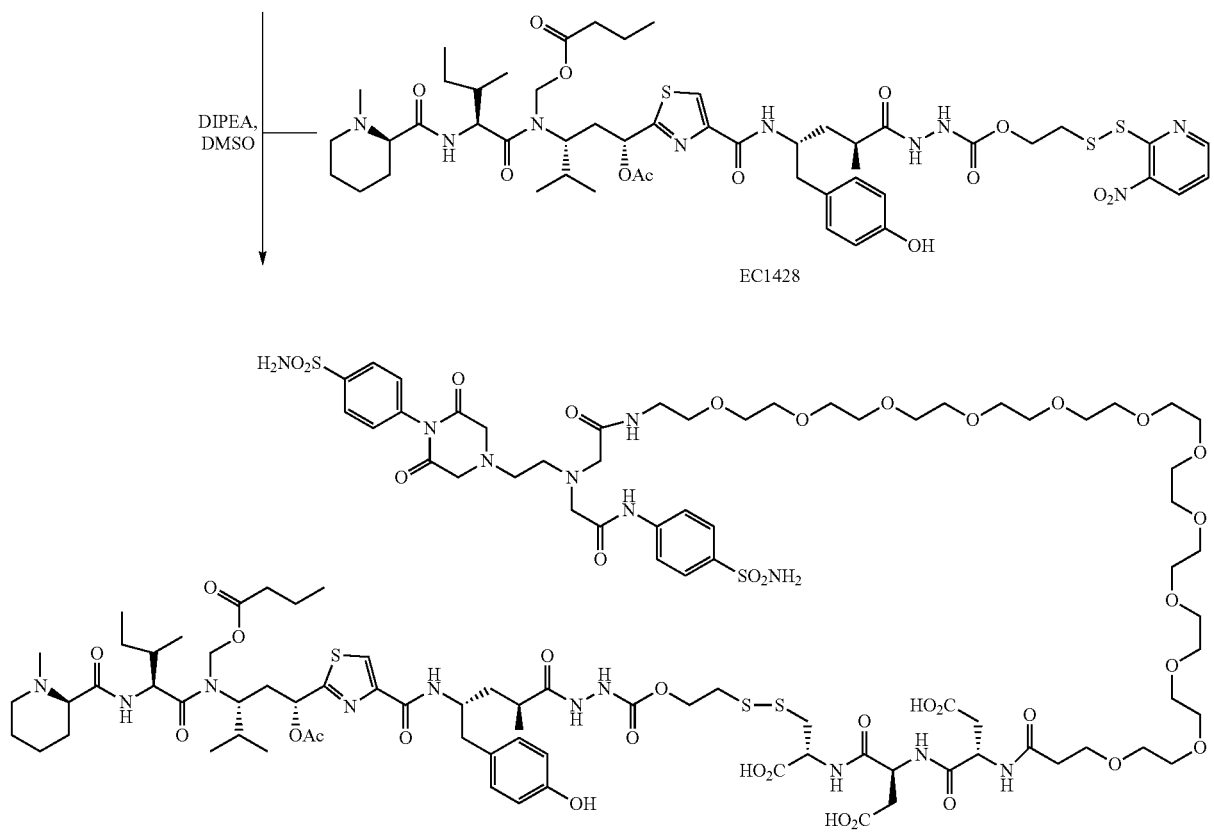

EC2765 (11.3 mg, 0.00745 mmol) was dissolved in DMSO (500 μL). To this solution was added DIPEA (13 μL, 10 eq.), followed by EC1428 (9.0 mg, 1.1 eq.) in DMSO (500 μL). The reaction was stirred for 40 minutes. The reaction was diluted with DMSO and loaded directly onto a Biotage C18 column (50 mM NH$_4$HCO$_3$ (pH=7)/ACN) and purified. Clean fractions were combined and lyophilized to give EC2766 (6 mg, 32% yield) as a white powder. ESI-MS [M+2H]$^{2+}$=1231.4

Example 15: Preparation of EC2767

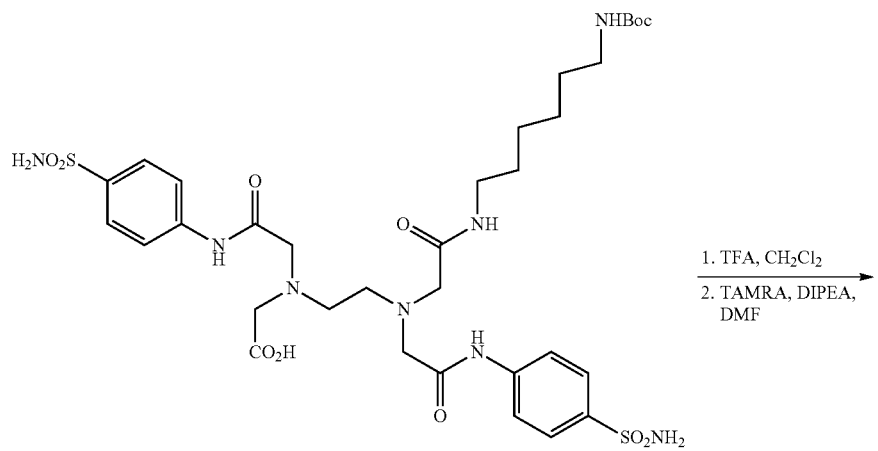

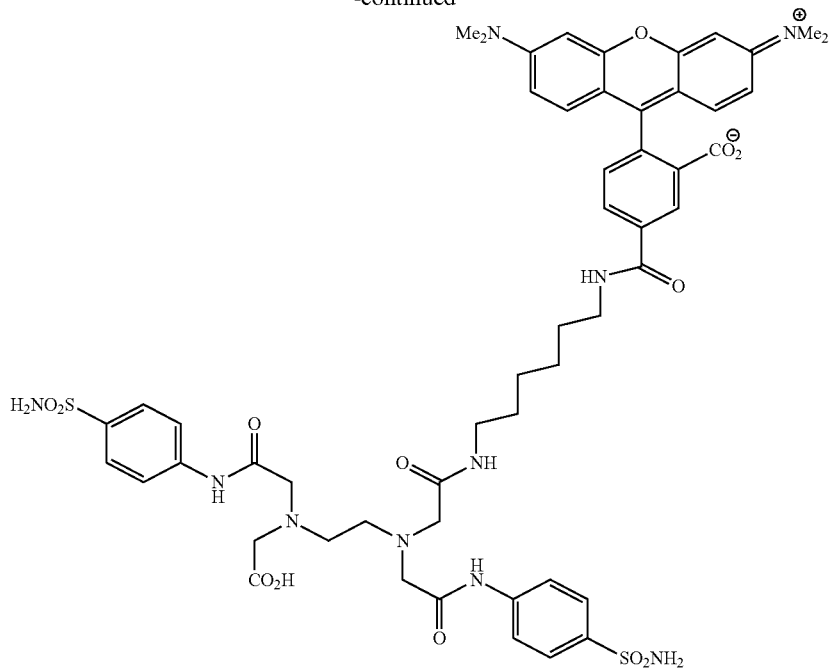

EC2677 (4.8 mg, 0.0060 mmol) was treated with TFA/CH₂Cl₂ (1 mL, 6:4) for 40 minutes. The solution was concentrated under reduced pressure and the residue was placed on the high vacuum for 2 hours. The residue was re-dissolved in DMF (500 μL) and treated with DIPEA (5 μL, 5 eq.) and TAMRA (2.6 mg, 0.8 eq) in DMF (500 μL). The reaction was allowed to stir for 1 hour. The reaction was diluted with DMSO and purified on a Biotage C18 column (50 mM NH₄HCO₃ (pH=7)/ACN). The pure fractions were combined and lyophilized to give EC2767 (3 mg, 56% yield) as a red powder. ESI-MS [M+H]⁺=1111.9

Example 16: Preparation of EC2798

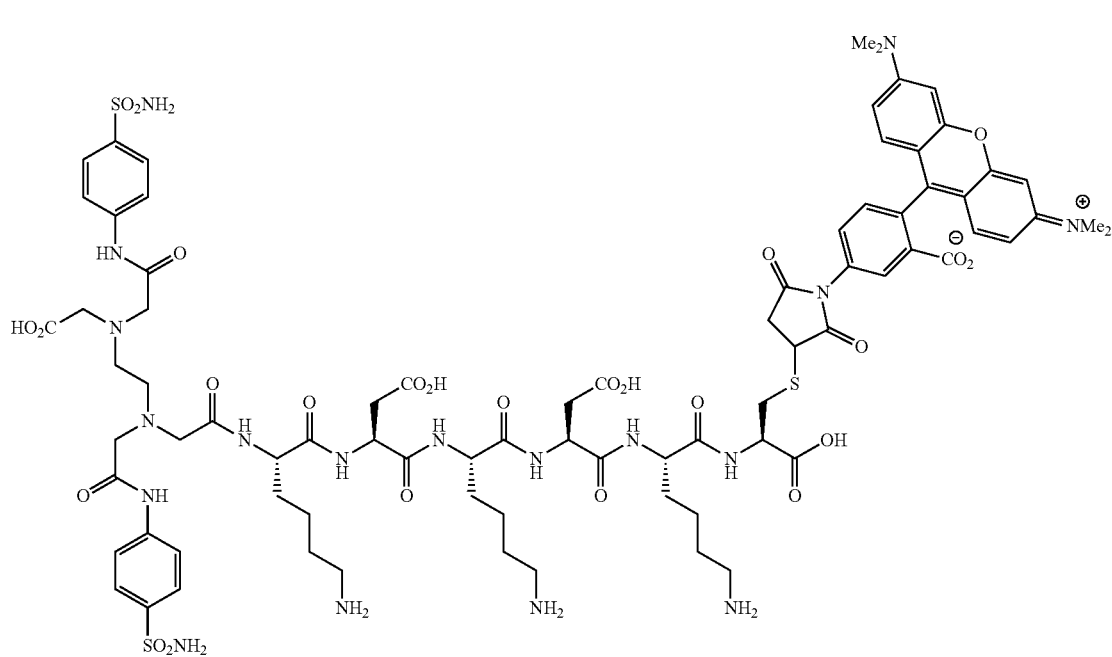

H-Cys(Trt)-2-Cl-Trt-resin (304 mg, 0.658 mmol/g, 0.2 mmol) was loaded into a peptide synthesis vessel and placed on the peptide synthesizer. Following standard Fmoc-solid phase peptide synthesis protocols, Fmoc-Lys(Boc)-OH (188 mg, 2 eq.) and Fmoc-Asp(Ot-Bu)-OH (165 mg, 2 eq.) were added alternately, in sequence, until three Lys residues and two Asp residues were added to the peptide chain. PyBop and DIPEA were used during each coupling step and 20% piperidine/DMF was used for each Fmoc deprotection step. After the final Lys residue was coupled and its Fmoc protecting group was removed, EC2665 (180 mg, 1.5 eq.), PyBop (156 mg, 1.5 eq.), and DIPEA (104 μL, 3 eq.) was added and the reaction was agitated under argon bubbling for 1 hour. After washing and drying, the peptide was cleaved from the resin with TFA/H$_2$O/TIPS/DTT (92.5:2.5: 2.5:2.5). The peptide was precipitated from the cleavage solution upon addition of Et$_2$O and was recovered by centrifugation. The crude peptide was re-dissolved in DMSO and purified by Biotage C18 column (0.1% TFA/ACN) to give, after recovery and lyophilization, purified cysteine terminating-CA IX targeting peptide (6 mg, 2.3% yield). ESI-MS [M+2H]$^{2+}$=660.0

A portion of this peptide (1.3 mg, 0.90 mol) was dissolved in 20 mM phosphate buffer (500 μL, pH=7) under argon bubbling. To this solution was added tetramethylrhodamine-5-maleimide (0.4 mg, 1 eq.) in DMSO (500 μL). The reaction was stirred under argon bubbling for 1 hour. The reaction was loaded into a Biotage C18 column (50 mM NH$_4$HCO$_3$ (pH=7)/ACN) and the clean fractions pooled and lyophilized to give EC2798 (0.8 mg, 44% yield) as a red solid. ESI-MS [M+2H]$^{2+}$=900.7

Example 17: Preparation of EC2668

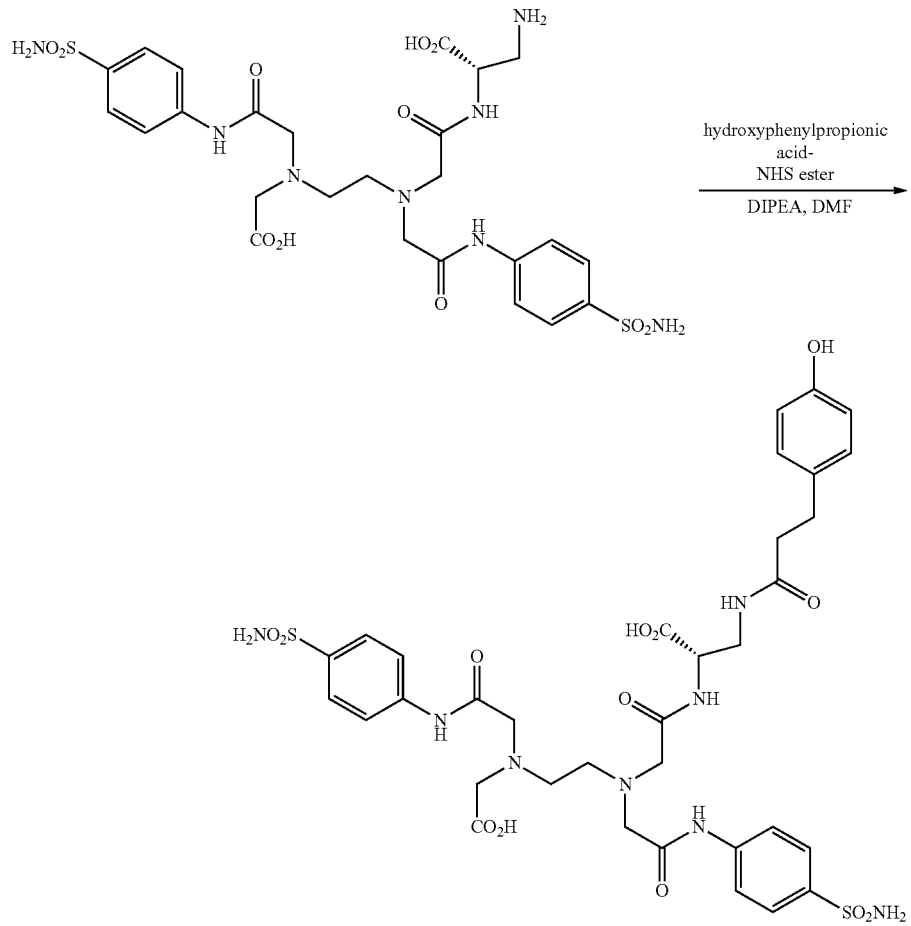

EC2667 (15 mg, 0.022 mmol) was dissolved in DMF (500 μL). To this solution was added DIPEA (15 μL, 4 eq.), followed by 3-(4-hydroxyphenyl)propionic acid N-hydroxysuccinimide ester (8.7 mg, 1.5 eq.) The reaction was allowed to stir for 40 minutes. The reaction was loaded directly onto a Biotage C18 column (50 mM NH$_4$HCO$_3$/ACN). Pure fractions were combined and lyophilized to give EC2668 (10 mg, 50% yield) as a white powder. ESI-MS [M+H]$^{+}$=835.8. Representative peaks $^1$H NMR (500 MHz, DMSO-D$_6$/D$_2$O): δ 7.82 (dd, 4H), 7.71 (d, 4H), 6.95 (d, 2H), 6.6 (d, 2H), 4.18 (m, 1H), 2.25 (t, 2H).

Example 18: Preparation of EC2673

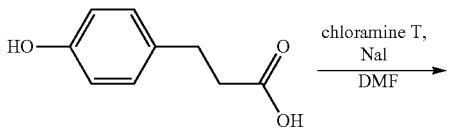

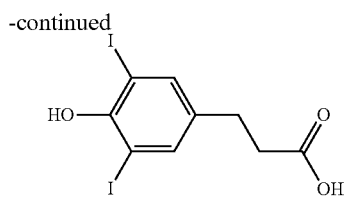

EC2673 was prepared based on the procedure described on Tet. Lett. (1985), 26, 2043. Briefly, to a solution of 3-(4-hydroxyphenyl)propionic acid (249 mg, 1.49 mmol) and NaI (269 mg, 1.2 eq.) in DMF (1 mL) was added chloramine T (500 mg, 1.2 eq.). The reaction was stirred for 1 hr. UPLC-MS analysis showed the formation of both mono-iodo-hydroxyphenylpropionic acid (EC2672) and bis-iodo-hydroxyphenylpropionic acid (EC2673). The reaction was diluted with water and acidified with 2N aqueous HCl solution. The aqueous layer was extracted with ethyl acetate. The organic layer was washed with 5% sodium thiosulfate, brine, dried over sodium sulfate, and concentrated under reduced pressure. The crude residue was dissolved in DMSO and purified by C18 Biotage column (0.1% TFA/ACN). Fractions containing pure EC2673 were pooled and the ACN removed under reduced pressure. The product was extracted from the remaining aqueous mixture with ethyl acetate. The organic layer was washed with brine, dried over sodium sulfate, and concentrated under reduced pressure to give EC2673 (136 mg, 22% yield) was a white solid. LC-MS [M−H]⁻=417.2

Example 19: Preparation of EC2674

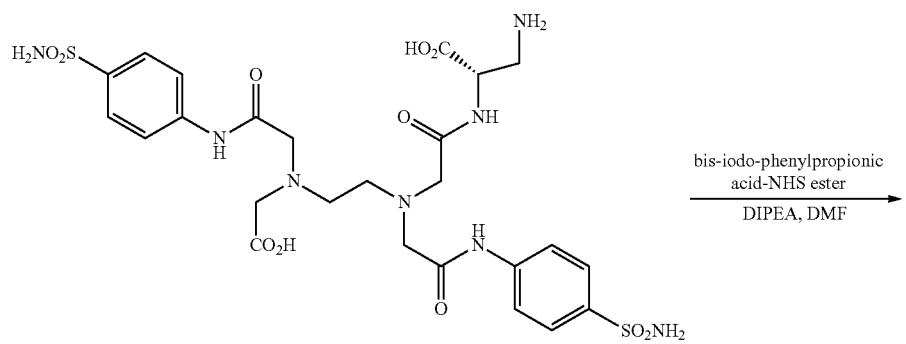

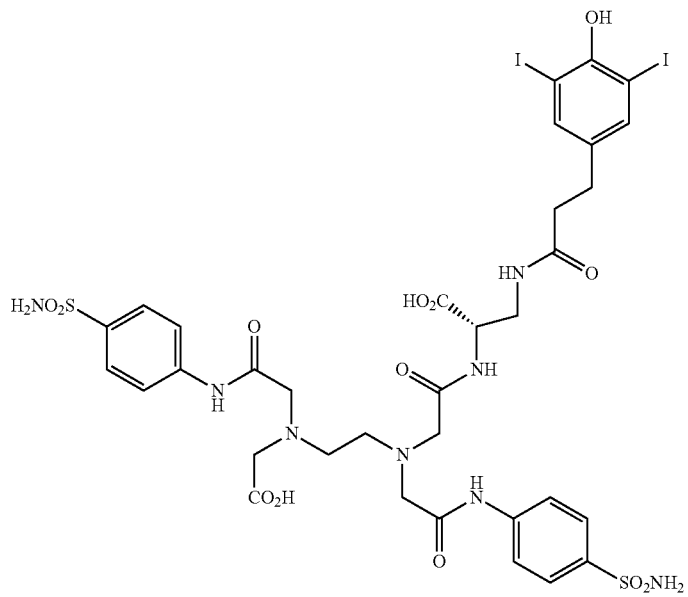

EC2673 (34 mg, 0.0813 mmol) was dissolved in dioxane (500 μL) and N-hydroxysuccinimide (18.7 mg, 2 eq., NHS) and DCC-resin (177 mg, 5 eq.) were added. The reaction was allowed to stir for 90 minutes. UPLC-MS showed complete conversion of the EC2673 to its NHS activated ester.

In another flask, EC2667 (22 mg, 0.5 eq.) was dissolved in DMF (500 μL) and DIPEA (42 μL, 3 eq.) was added. To this solution was added the solution of the NHS activated EC2673 via a syringe fitted with a syringe filter. The reaction was allowed to stir at room temperature for 1 hour. The reaction was loaded into a C18 Biotage column (NH$_4$HCO$_3$/ACN). The clean fractions were pooled and lyophilized to give EC2674 (12 mg, 27% yield) as a white powder. ESI-MS [M−H]$^−$=1084.9. Representative peaks $^1$H NMR (500 MHz, DMSO-D$_6$/D$_2$O): δ 7.81 (m, 4H), 7.73 (d, 4H), 7.55 (s, 2H), 4.08 (m, 1H), 2.58 (t, 2H), 2.25 (t, 2H).

Example 20: Preparation of EC3105

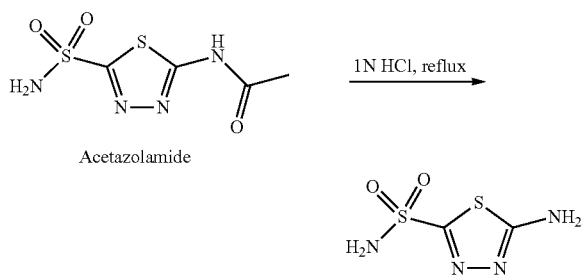

Acetazolamide

Acetazolimide (3.6 g, 16 mmol) was suspended in 1N HCl solution (80 mL) and heated to reflux for 3 hours. The reaction was cooled in an ice bath to room temperature and 10 N NaOH solution was added to raise the pH~6. The reaction was cooled in the refrigerator over the weekend. The resulting white solid was filtered through a Buchner funnel, washed with a small amount of water, and dried under reduced pressure to give EC3105 (2.6 g, 88% yield). ESI-MS [M+H]$^+$=180.8. $^{13}$C NMR (125 MHz, DMSO-d$_6$): δ 172, 158.

Example 21: Preparation of EC3108

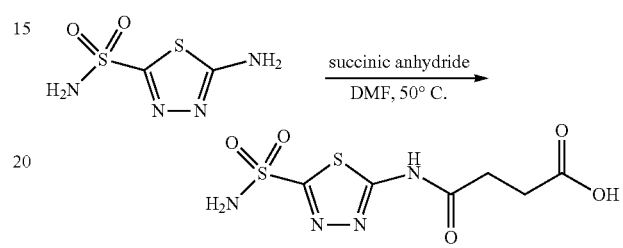

EC3105 (178 mg, 0.988 mmol) was dissolved in DMF (1.6 mL). To this solution was added succinic anhydride (98.8 mg, 1 eq.) The solution was heated to 50° C. overnight. The reaction was diluted with water and loaded onto a Biotage C18 column (0.1% TFA/ACN) and purified. After freeze drying, EC3108 (92 mg, 33% yield) was recovered as a white solid. ESI-MS [M+H]$^+$=281.1. $^{13}$C NMR (125 MHz, DMSO-d$_6$): δ 173.5, 171.9, 164.9, 161.2, 30.4, 28.5.

Example 22: Preparation of EC3114

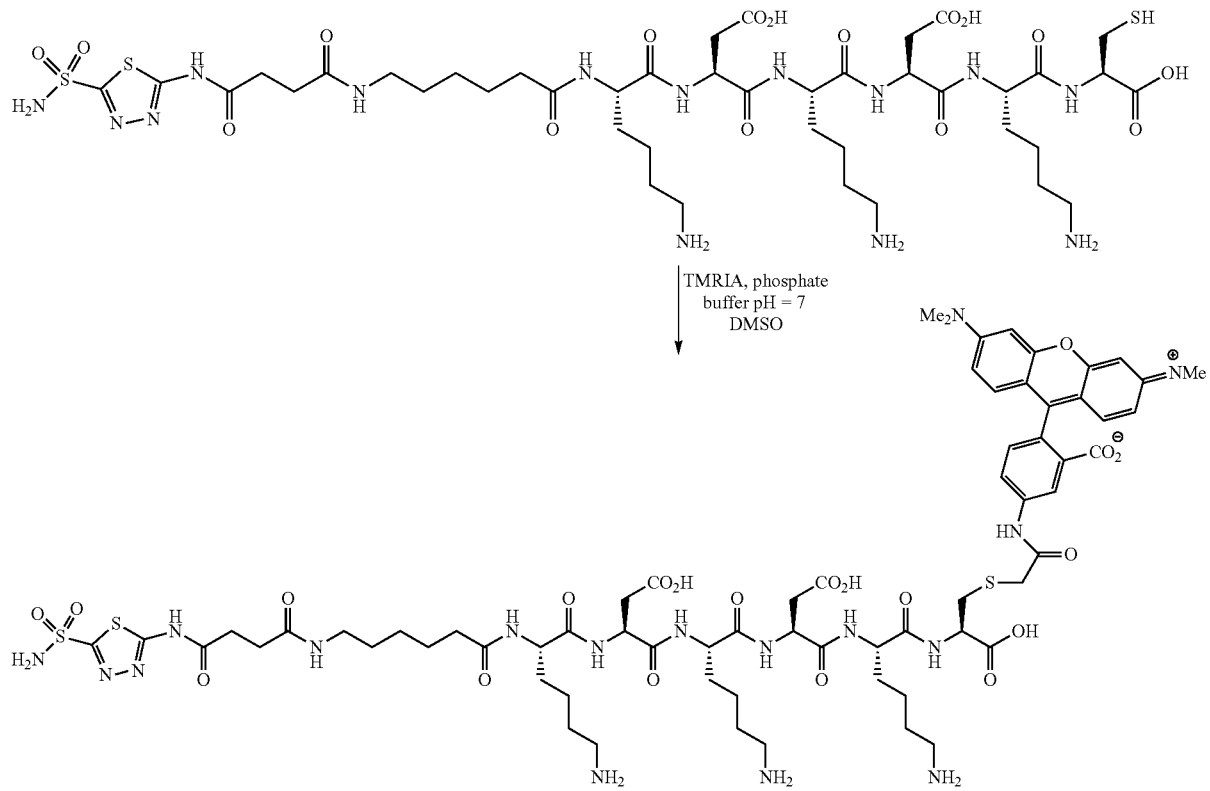

H-Cys(Trt)-2-Cl-Trt-resin (608 mg, 0.658 mmol/g, 0.4 mmol) was loaded into a peptide synthesis vessel. Following standard Fmoc-solid phase peptide synthesis protocols, Fmoc-Lys(Boc)-OH (374 mg, 2 eq.) and Fmoc-Asp(Ot-Bu)-OH (329 mg, 2 eq.) were added alternately, in sequence, until three Lys residues and two Asp residues were added to the peptide chain. PyBop (416 mg, 2 eq.) and DIPEA (278 µL, 4 eq.) were used during each coupling step (1 hour coupling time) and 20% piperidine/DMF was used for each Fmoc deprotection step (2×20 minutes deprotection time).

To ½ of this resin (0.2 mmol) was then added 6-aminohexanoic acid (141 mg, 2 eq.) with PyBop (208 mg, 2 eq.) and DIPEA (139 µL, 4 eq.), after the Fmoc protecting group was removed. To ½ of this resin (0.1 mmol), after a final Fmoc deprotection, was added EC3108 (42 mg, 1.5 eq.), PyBop (78 mg, 1.5 eq.), and DIPEA (35 µL, 3 eq.). After washing and drying, the peptide was cleaved from the resin with TFA/H$_2$O/TIPS/DTT (92.5:2.5:2.5:2.5). The peptide was precipitated from the cleavage solution upon addition of Et$_2$O and was recovered by centrifugation. The crude peptide was re-dissolved in DMSO and purified by Biotage C18 column (0.1% TFA/ACN) to give, after recovery and lyophilization, purified cysteine terminating-CA IX targeting peptide EC3109 (72 mg, 60% yield). ESI-MS [M+2H]$^{2+}$=556.3

A portion of EC3109 (3.5 mg, 1.3 eq.) was dissolved in 50 mM phosphate buffer (1 mL, pH=7) under argon bubbling. To this solution was added tetramethylrhodamine-5-iodoacetimide (0.4 mg, 0.0024 mmol, TMRIA) in DMSO (1 mL). The reaction was stirred under argon bubbling for 1.5 hours. The reaction was loaded into a Biotage C18 column (50 mM phosphate buffer (pH=7)/ACN). The clean fractions were pooled, the ACN removed, and were desalted with a Biotage C18 column (H$_2$O/ACN) followed by lyophilization to give EC3114 (1.8 mg, 46% yield) as a red solid. ESI-MS [M+2H]$^{2+}$=777.8

Example 23: Synthesis of EC3156

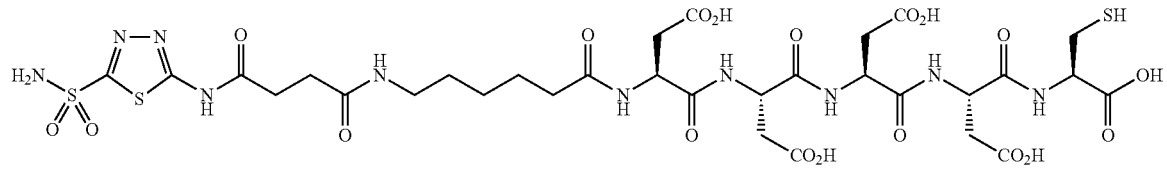 [SMILES: NS(=O)(=O)c1nnc(NC(=O)CCC(=O)NCCCCCC(=O)N[C@@H](CC(=O)O)C(=O)N[C@@H](CC(=O)O)C(=O)N[C@@H](CC(=O)O)C(=O)N[C@@H](CC(=O)O)C(=O)N[C@@H](CS)C(=O)O)s1]

H-Cys(Trt)-2-Cl-Trt-resin (760 mg, 0.658 mmol/g, 0.5 mmol) was loaded into a peptide synthesis vessel and placed on the peptide synthesizer. Following standard Fmoc-solid phase peptide synthesis protocols, Fmoc-Asp(Ot-Bu)-OH (412 mg, 2 eq.) were added four times followed by Fmoc-6-aminohexanoic acid (353 mg, 2 eq.) PyBop and DIPEA were used during each coupling step (1 hour duration) and 20% piperidine/DMF was used for each Fmoc deprotection step (2×20 minutes duration).

A portion of this resin (184 mg, 0.09 mmol) was treated with EC3108 (30 mg, 1.2 eq.), DIPEA (39 mL, 2.5 eq.) and PyBop (56 mg, 1.2 eq.), after the final Fmoc protecting group had been removed, for 1 hour. After washing and drying, the peptide was cleaved from the resin with TFA/H$_2$O/TIPS/DTT (92.5:2.5:2.5:2.5). The peptide was precipitated from the cleavage solution upon addition of Et$_2$O and was recovered by centrifugation. The crude peptide was re-dissolved in DMSO and purified by Biotage C18 column (0.1% TFA/ACN) to give, after recovery and lyophilization, purified peptide EC3156 (45 mg, 52% yield). ESI-MS [M+H]$^+$=957.6 Representative peaks $^1$H NMR (500 MHz, DMSO-d$_6$/D$_2$O): δ 4.6-4.4 (m, 4H), 3.8 (m, 1H), 2.99 (t, 2H), 2.9-2.6 (m, 8H), 2.08 (t, 2H), 1.45 (dt, 2H), 1.35 (dt, 2H), 1.2 (dt, 2H).

Example 24: Synthesis of EC3157

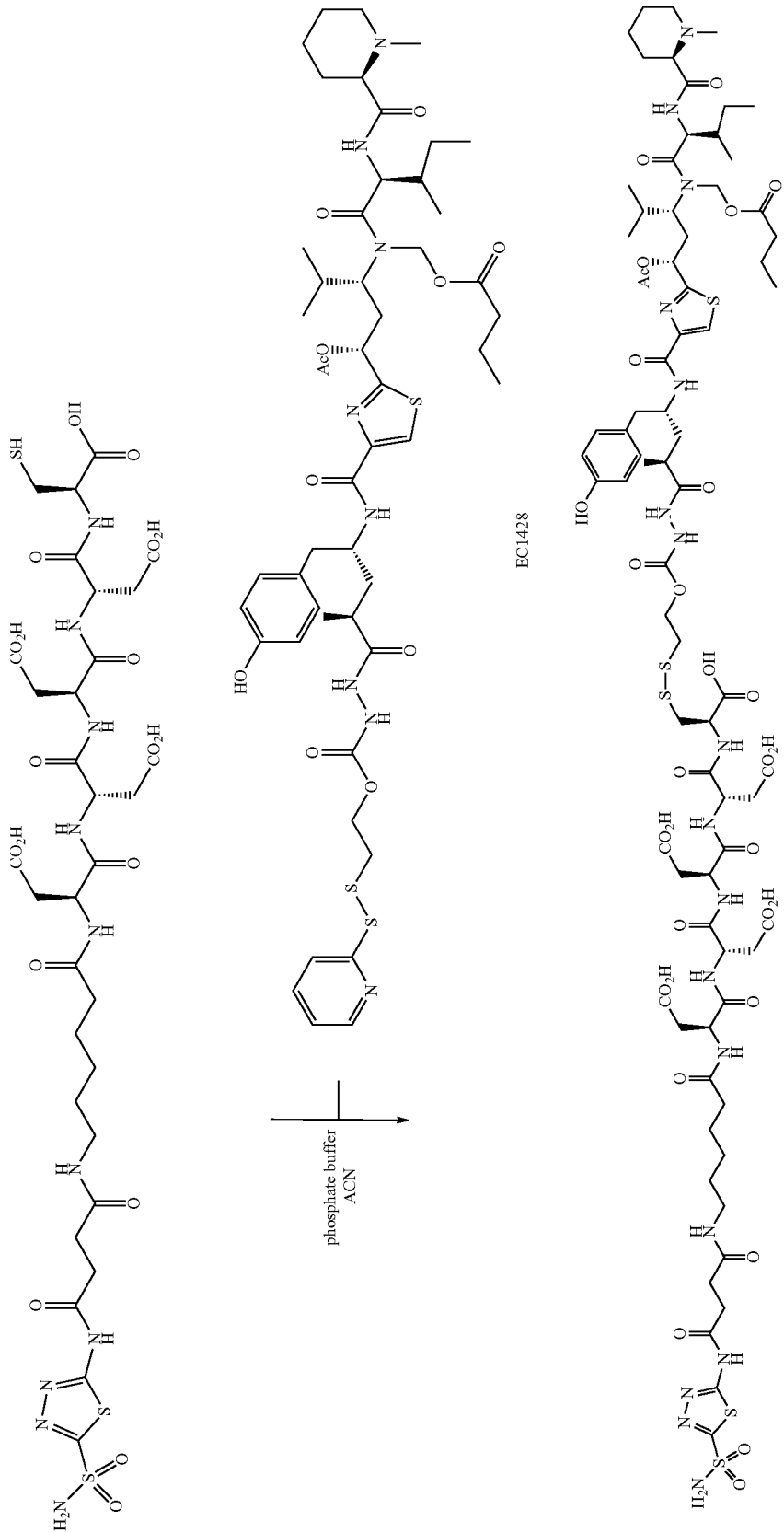

EC3156 (10 mg, assumed to be 0.0104 mmol) was dissolved in 50 mM phosphate buffer (1.5 mL, pH=7, previously sparged with Ar). To this solution was added EC1428 (12.7 mg, 1.1 eq.) in ACN (2.5 mL). The reaction was allowed to proceed under argon bubbling for 1 hour. The reaction was diluted with $H_2O$ and loaded onto a Biotage C18 column (50 mM $NH_4HCO_3$/ACN). After lyophilization, EC3157 (6.5 mg, 33% yield) was recovered as a white solid. ESI-MS $[M+H]^+$=1903, $[M+2H]^{2+}$=951.9. Representative peaks $^1H$ NMR (500 MHz, DMSO-$d_6$/$D_2O$): δ 8.19 (s, 1H), 7.88 (bd, 1H), 6.98 (d, 2H), 6.78 (d, 2H), 6.18 (db, 1H), 5.73 (d, 1H), 5.23 (d, 1H), 4.55-4.4 (m, 5H), 4.6-4.0 (m, 4H), 3.2-2.8 (m, 9H), 2.75-2.6 (m, 8H), 1.0 (d, 3H), 0.95 (d, 3H), 0.8 (m, 10H), 0.65 (d, 3H).

In Vitro Experiments

Example 25: Detection of CAIX in RCC4 and HT29 Cells by Western Blot

Cell lysates of RCC4+vector and RCC4+VHL were prepared by dissociating one T150 flask of confluent cells with cell dissociation solution. Cell pellets were washed with PBS, pH 7.4 and were then lysed in 500 μL of RIPA lysis buffer containing 1× Halt Protease Inhibitor Cocktail (Pierce). Lysates were incubated on ice for 30 min prior to centrifugation at 14,000×g for 15 min at 4° C. to remove insoluble material.

For HT29 cells, one confluent T-25 flask was placed under hypoxic conditions overnight (0.13% $O_2$, 5% $CO_2$, 37° C.) and another confluent T-25 was placed under normoxic conditions (5% $CO_2$, 95% air, 37° C.). The next day, both flasks were processed as described above for the RCC4 cells with the exception that the cell pellets were lysed with 200 μL of RIPA buffer containing protease inhibitors.

Protein concentrations were determined using the Qubit fluorimeter. Fifty micrograms per lane of cell lysates were loaded onto an Any KD Mini PROTEAN TGX Ready Gel (Bio-Rad). PageRuler Prestained Protein Ladder was used as a molecular weight marker (10 μL/lane). Samples were electrophoresed at 100 V for 90 min in Tris/Glycine/SDS buffer (Bio-Rad). Gels were removed from the casing, and protein was transferred onto 0.2 μm nitrocellulose membrane at 300 mA for 75 min in Tris/Glycine buffer (Bio-Rad). Membranes were incubated briefly in Ponceau S solution to visualize the protein bands. They were then blocked using Superblock blocking buffer (Pierce, TBS-based) for 1 h at RT. Membranes were washed 3 times for 5 min in Tris-buffered saline, pH 7.5/0.05% Tween-20 (Wash Buffer).

Figure 1B:
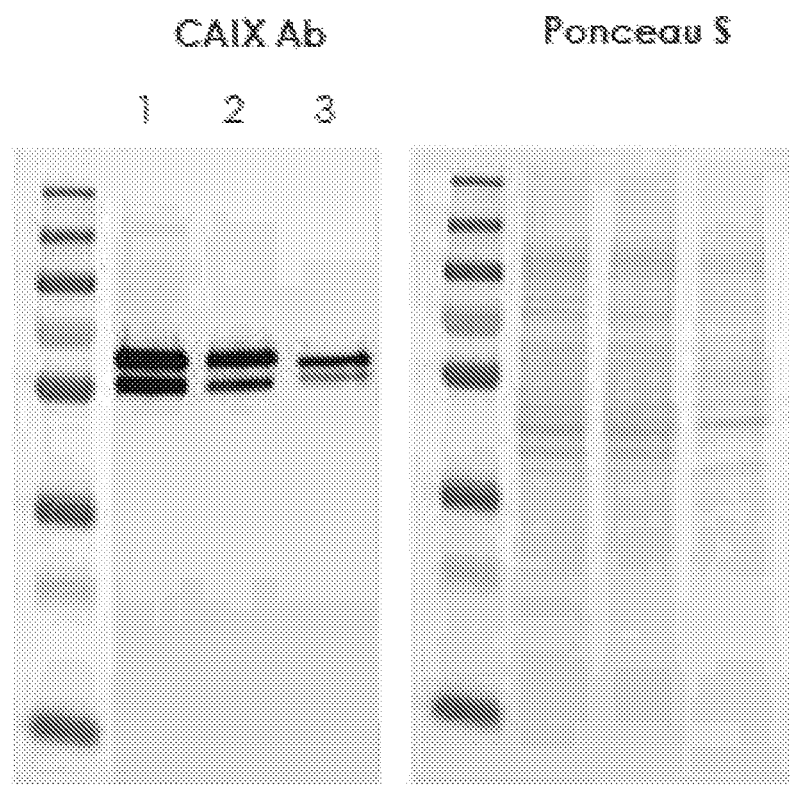
FIG. 1B shows results of CA IX expression analysis in HT29 cells. Lane 1: HT29 cells, hypoxic (0.1% $O_2$ overnight); Lane 2: HT29 cells; normoxic; Lane 3: RCC4 cells+vector alone.

Primary antibody (anti-CAIX monoclonal antibody GT12, Genetex) was prepared in Wash Buffer+5% BSA at a dilution of 1:500 (50% glycerol stock). Membranes were incubated in primary antibody overnight at 4° C. The following day, membranes were washed 3 times with Wash Buffer. Secondary antibody (goat anti-mouse IgG-HRP conjugate, Jackson Immunoresearch) was diluted 1:10,000 in Wash Buffer+5% milk. Membranes were incubated in secondary antibody for 1 hour at RT followed by 3 washes in Wash Buffer. Membranes were washed 2 additional times in TBS (no Tween-20). Bands were visualized using Supersignal West Pico Chemiluminescent Substrate (Pierce). Results are shown in FIG. 1.

Example 26: CAIX Saturation Ligand Binding Assay

Figure 2:
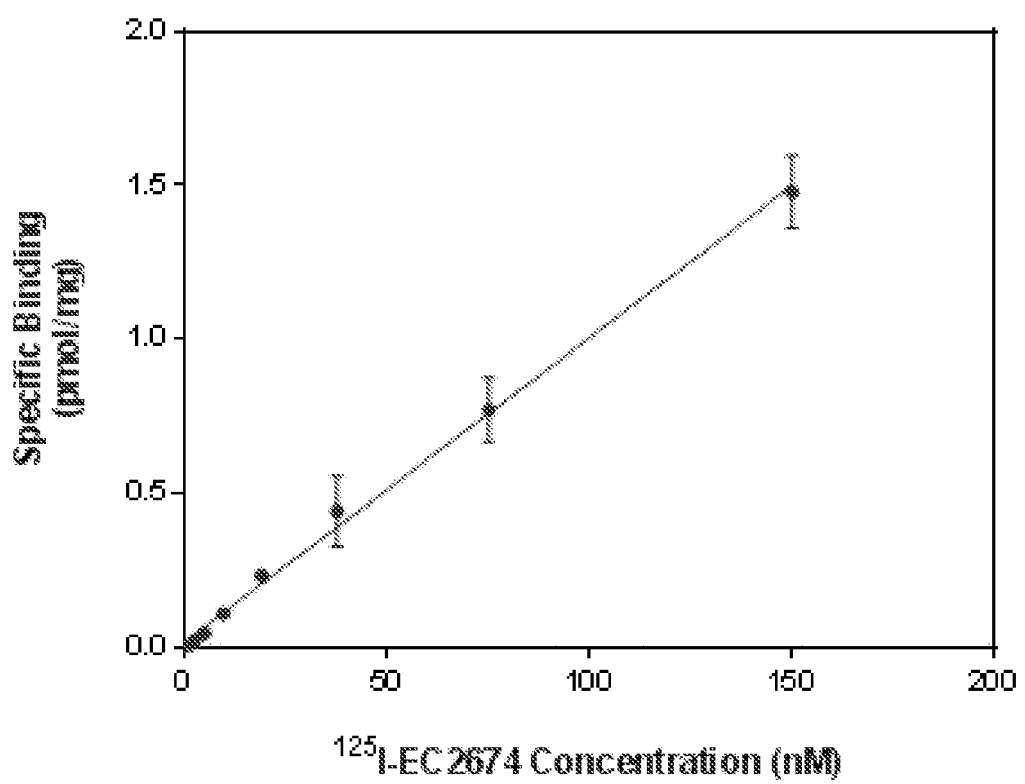
FIG. 2 shows the results for the CA IX Saturation Ligand Binding Assay. Binding of $^{125}$I-CAIX ligand ($^{125}$I-EC2674) to HT29 cells where $^{125}$I-EC2674, 2 hr, 37° C., 1.3% $O_2$, McCoy's Medium+10% FBS.

HT29 cells were seeded into 24-well plates at 1×10⁶ cells per well in McCoy's 5A medium containing 10% fetal bovine serum (FBS) and were allowed to attach for 48 h in an incubator with an atmosphere of 5% $CO_2$/95% air and 37° C. The evening prior to the binding assay, cells were placed in a Hypoxylab workstation (Oxford Optronix) set at 10 mm Hg (1.3% $O_2$), 5% $CO_2$, and 37° C. (hypoxic conditions). Dilutions of $^{125}I$-CAIX radioligand were prepared in McCoy's 5A medium/10% FBS with and without 30 μM CAIX competitor. Cells were placed in the Hypoxylab workstation and were incubated for 2 h under hypoxic conditions. Cells were then removed from the Hypoxylab, were washed 3 times with ice-cold PBS, pH 7.4, and were solubilized with 500 μL 0.1N NaOH/0.1% Triton X-100. Cell lysates (450 μL) were counted in a Wizard2 gamma counter (Perkin Elmer). The remaining lysates were used to determine protein content using the BCA Protein Assay (Pierce). To determine specific binding, CPM from competition groups were subtracted from non-competition groups, and data were normalized with respect to protein content. Results are shown in FIG. 2.

Example 27: CAIX Competitive Binding Assay

Figure 3:
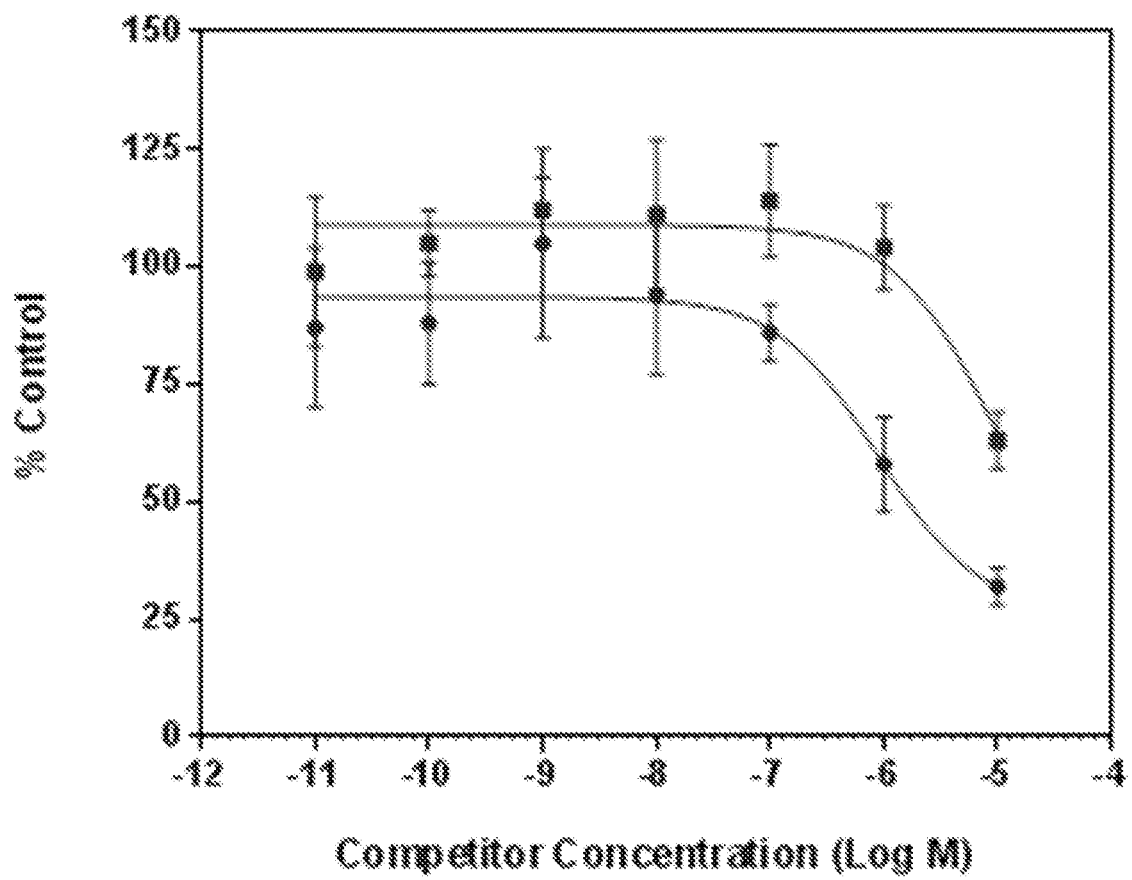
FIG. 3 shows results for the CA IX competitive binding assay in HT29 cells where 2 nM $^{125}$I-EC2674 or EC2711, 2 hr, 37° C., 1.3% $O_2$, McCoy's Medium+10% FBS. (●) EC2674 ($IC_{50}$=852 nM); (■) EC2711 ($IC_{50}$=9 nM).

HT29 cells were seeded into 24-well plates at 0.5×10⁶ cells per well in McCoy's 5A medium containing 10% fetal bovine serum (FBS) and were allowed to attach for 48 h in an incubator with an atmosphere of 5% $CO_2$/95% air and 37° C. The evening prior to the binding assay, cells were placed in a Hypoxylab workstation set at 10 mm Hg (1.3% $O_2$), 5% $CO_2$, and 37° C. (hypoxic conditions). A single concentration of $^{125}I$-CAIX radioligand was used (2 nM). Serial dilutions of competitors (EC2674 and EC2711) were prepared in McCoy's 5A medium/10% FBS. Binding solutions (500 μL) containing the radioligand and competitor dilutions were placed on the cells, and cells were incubated in the Hypoxylab workstation for 2 h under hypoxic conditions. Cells were then removed from the Hypoxylab and were washed 3 times with ice-cold PBS, pH 7.4. Cells were solubilized with 500 μL of 0.1N NaOH/0.1% Triton X-100. Cell lysates (450 μL) were counted in a Wizard2 gamma counter (Perkin Elmer). CPM values for each competitor concentration were normalized to values for radioligand binding in the absence of competitor. Results are shown in FIG. 3.

Example 28: CA IX Competitive Binding Assay (pH 6.8 vs. 7.4 Buffers+$Zn^{2+}$)

Figure 4:
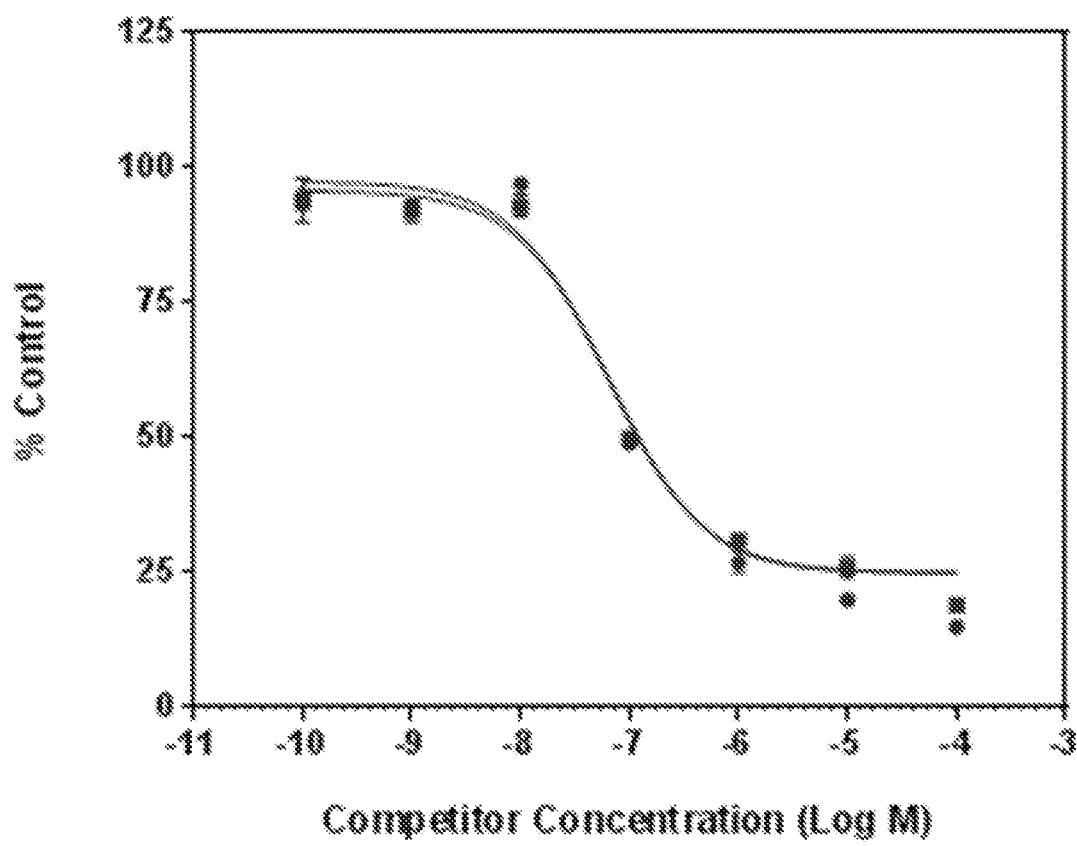
FIG. 4 shows results for the CA IX competitive binding assay (pH 6.8 vs. 7.4 Buffers+$Zn^{2+}$) in HT29 cells where 2 nM $^{125}$I-EC2674, 2 hr, 37° C., 1.3% $O_2$, pH 6.8 v. pH 7.4 buffers. (●) pH 6.8 ($IC_{50}$=62.5 nM); (■) pH 7.4 ($IC_{50}$=66.5 nM).

Following the procedure for the previous competitive binding assay (Example 22), the CAIX Competitive Binding Assay (pH 6.8 vs. 7.4 Buffers+$Zn^{2+}$) was carried out with the following modifications from Example 22. Two different buffers were tested: 1) 20 mM BES, pH 6.8, 140 mM NaCl, 1 mM $ZnSO_4$ and 2) 20 mM Tris, pH 7.4, 140 mM NaCl, 1 mM $ZnSO_4$. These buffers were used for both binding and washing. Only the homologous cold-iodine labeled CAIX ligand, EC2674, was assessed for competitive binding. Results are shown in FIG. 4.

Example 29: CAIX Competitive Binding Assay (McCoy's 5A Medium+$Zn^{2+}$)

Figure 5A:
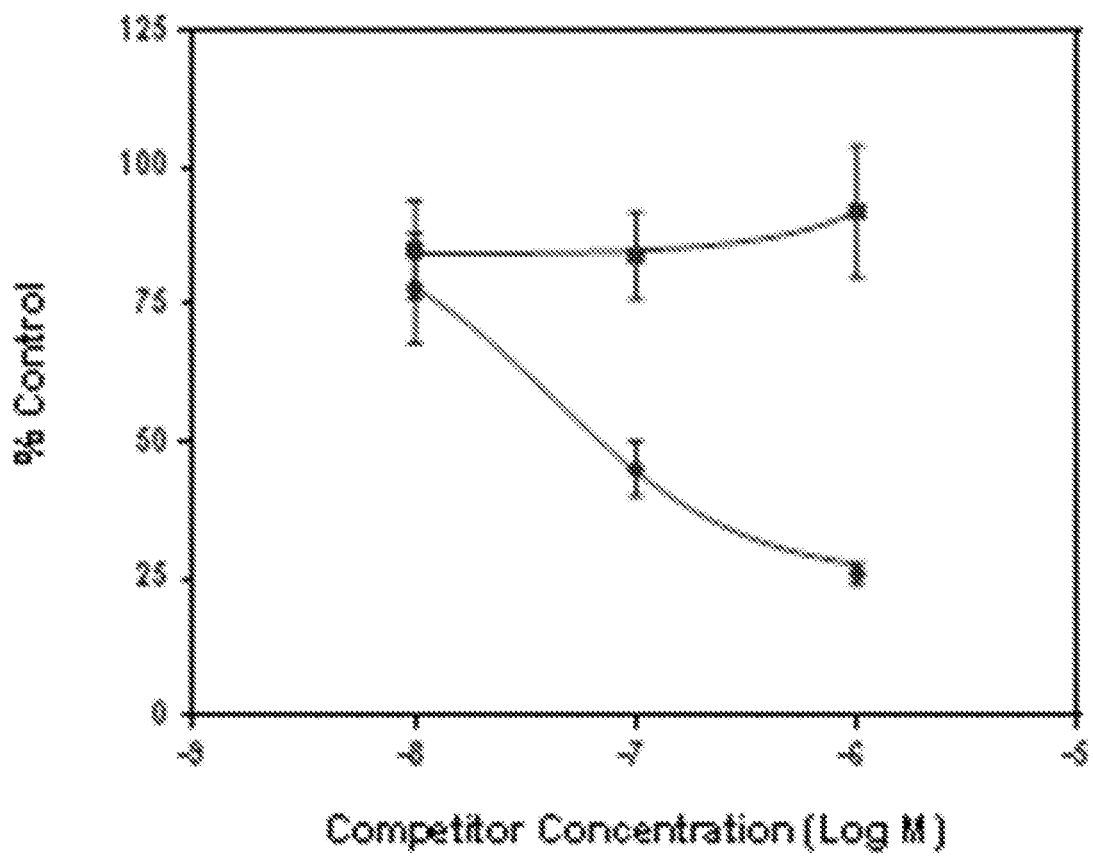
FIG. 5A; (●) McCoy's+10% FBS+Zn; (■) McCoy's+10% FBS+no Zn.
Figure 5B:
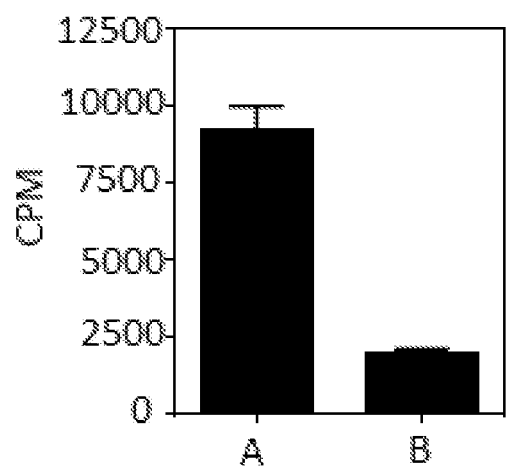
FIG. 5B; $^{125}$I-EC2674 ligand binding; (A) McCoy's+10% FBS+Zn; (B) McCoy's+10% FBS+no Zn.

Following the procedure for the previous competitive binding assay (Example 22), the CAIX Competitive Binding Assay (McCoy's 5A Medium+$Zn^{2+}$) was carried out with the following modifications from Example 22. The binding medium consisted of McCoy's 5A medium containing 10% FBS and 1 mM $ZnSO_4$. This modified medium was used for both binding and washing. Only the homologous cold-iodine labeled CAIX ligand, EC2674, was assessed for competitive binding. Results are shown in FIG. 5A and FIG. 5B.

Figure 6:
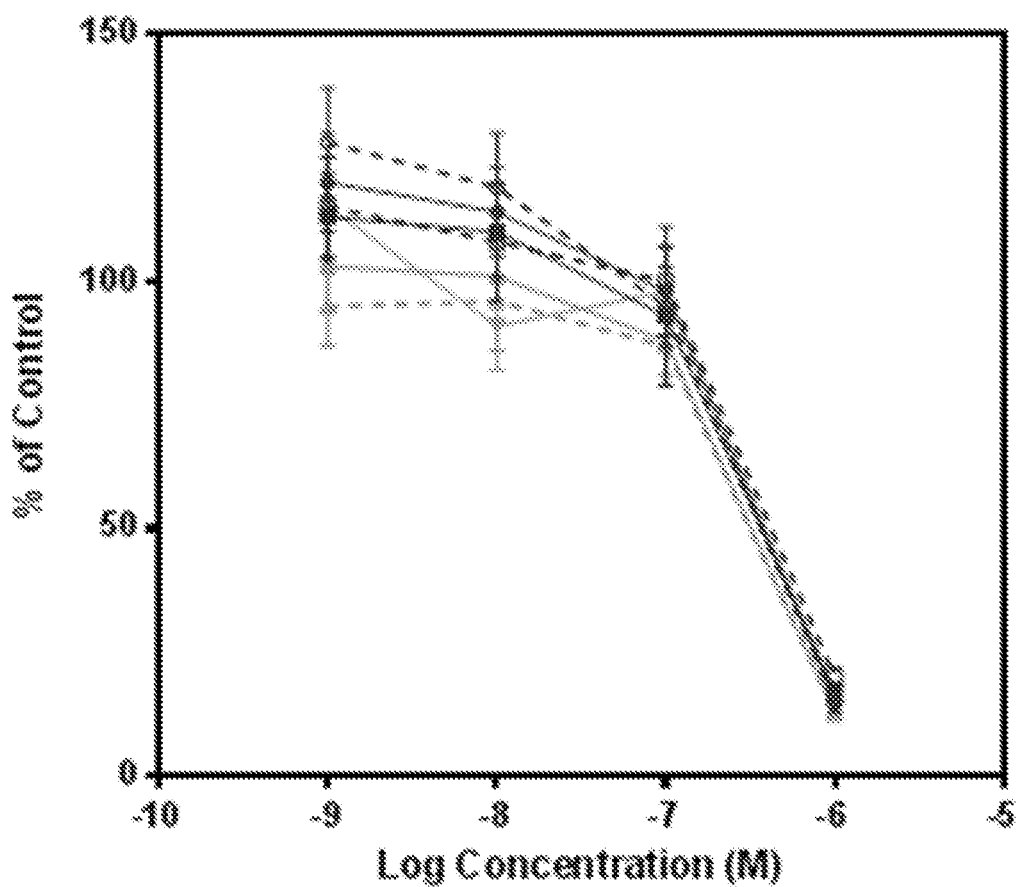
FIG. 6 shows results for the cytotoxicity of CA IX, folate receptor, and non-targeted Tubulysin B conjugates on HT29 cells. (●) EC2711 (CA IX); (○) EC2711+competition; (■) EC2763 (CA IX); (□) EC2763+Competition; (▲) EC1456; (Δ) EC1456+Competition; (▼) EC2752 (non-targeted Tubulysin).

Example 30: Cytotoxicity of CAIX, FR, and Non-Targeted Tubulysin B Conjugates on HT29 Cells HT29 cells were seeded into 24-well plates at $1.5 \times 10^6$ cells per well in McCoy's 5A medium containing 10% FBS and were allowed to attach for 48 h in an incubator with an atmosphere of 5% $CO_2$/95% air and 37° C. Test compounds included tubulysin B conjugates targeted to CAIX (EC2711 and EC2763), FR (EC1456), and untargeted tubulysin B (EC2752). Dilutions of test compounds were made in McCoy's 5A medium/10% FBS. For each targeted agent, competition groups were prepared using the appropriate competitor at 100 µM (EC2665 as the CAIX competitor and FA as the FR competitor). Drug solutions (500 µL) were added to cells, and cells were placed in a standard tissue culture incubator (5% $CO_2$, 37° C., normoxic) and incubated for 2 h. Cells were then washed 2 times with McCoy's 5A medium/10% FBS. Fresh medium was placed in each well, and cells were placed in the tissue culture incubator for 72 h. To assess cytotoxicity by $^3$H-thymidine incorporation, $^3$H-thymidine solution (1 µCi/mL) was prepared in McCoy's 5A medium/10% FBS. $^3$H-Thymidine solution (500 µL) was added to each well and cells were incubated in the tissue culture incubator for 4 h. Cells were then washed 2 times with PBS, pH 7.4, followed by precipitation with 5% TCA. Cells were solubilized with 500 µL of 0.25 N NaOH, and 450 µL of each cell lysate was counted in a Tri-Carb Liquid Scintillation Analyzer (Perkin Elmer). CPM values for treated groups were normalized with respect to untreated controls. Results are shown in FIG. 6.

Example 31: Binding of a CAIX Imaging Conjugate to HT29 Cells

Figure 7A:
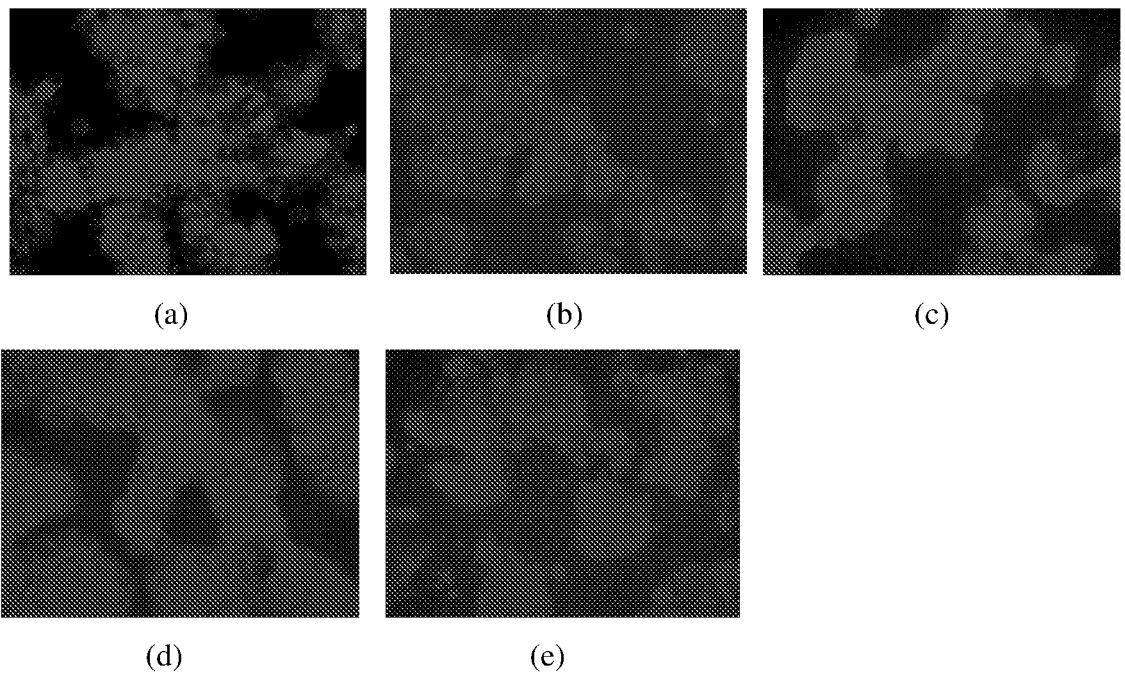
FIG. 7A shows binding of EC3114 to HT-29 cells after 4 h incubations with (a) 10 nM, (b) 40 nM, (c) 120 nM, (d) 360 nM, and (e) 40 nM+100-fold (4 μM) excess CA IX ligand, respectively.
Figure 7B:
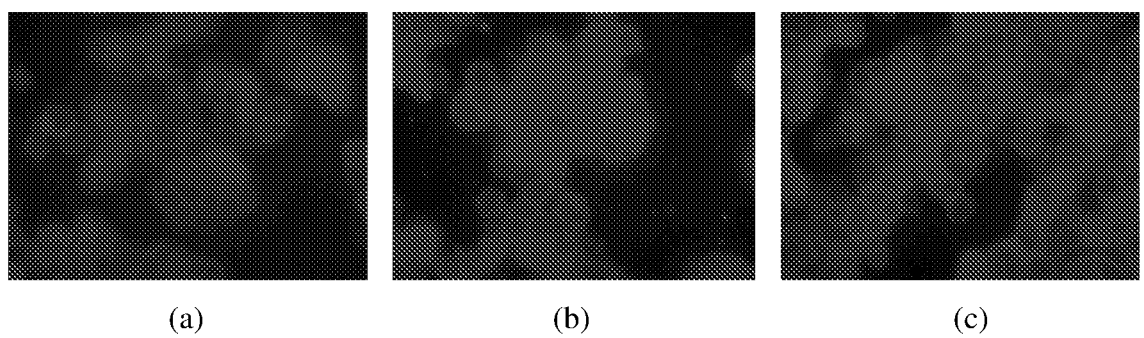
FIG. 7B shows binding of 40 nM of EC3114 at (a) 1 h, (b) 2 h, and (c) 4 h post-incubation, respectively. Note the predominant membrane surface binding of EC3114 with little evidence of cell internalization.
Figure 8A:
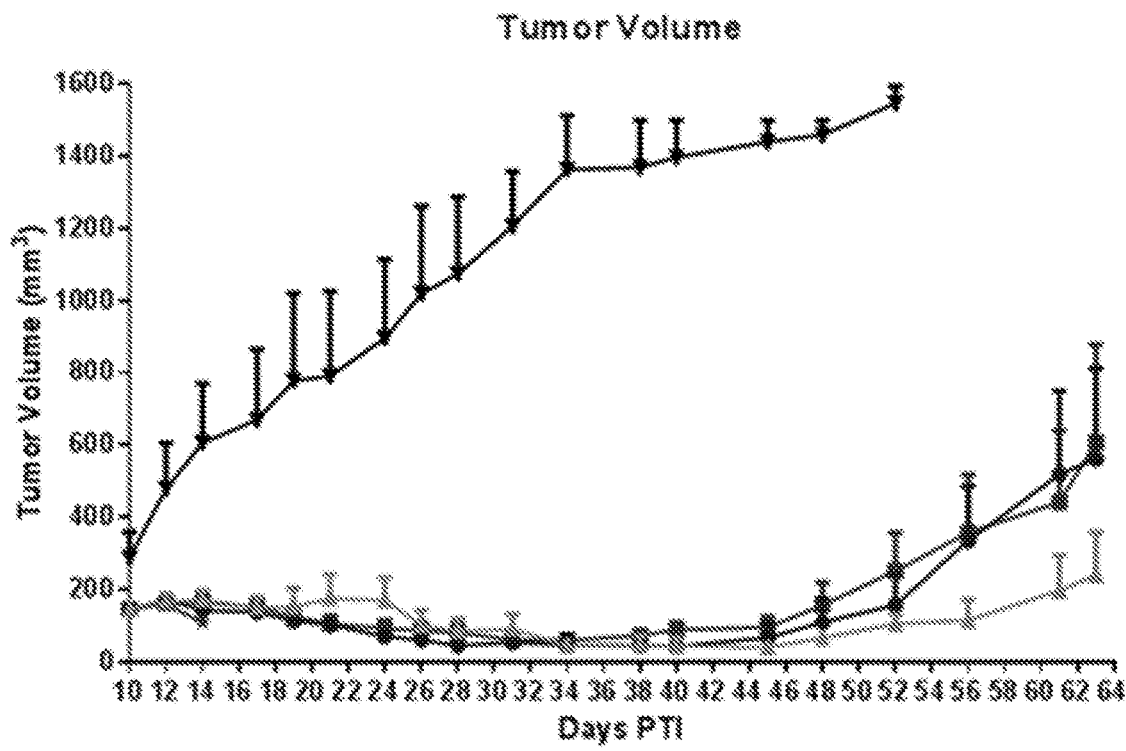
FIG. 8A shows tumor volumes after treatment with CA IX targeted conjugates (▼) Control; (▲) EC2711 {2,2,0}; (●) EC2763 {0,2,2}; (■) EC2766 {2,1,1}; (*) EC2761.
Figure 8B:
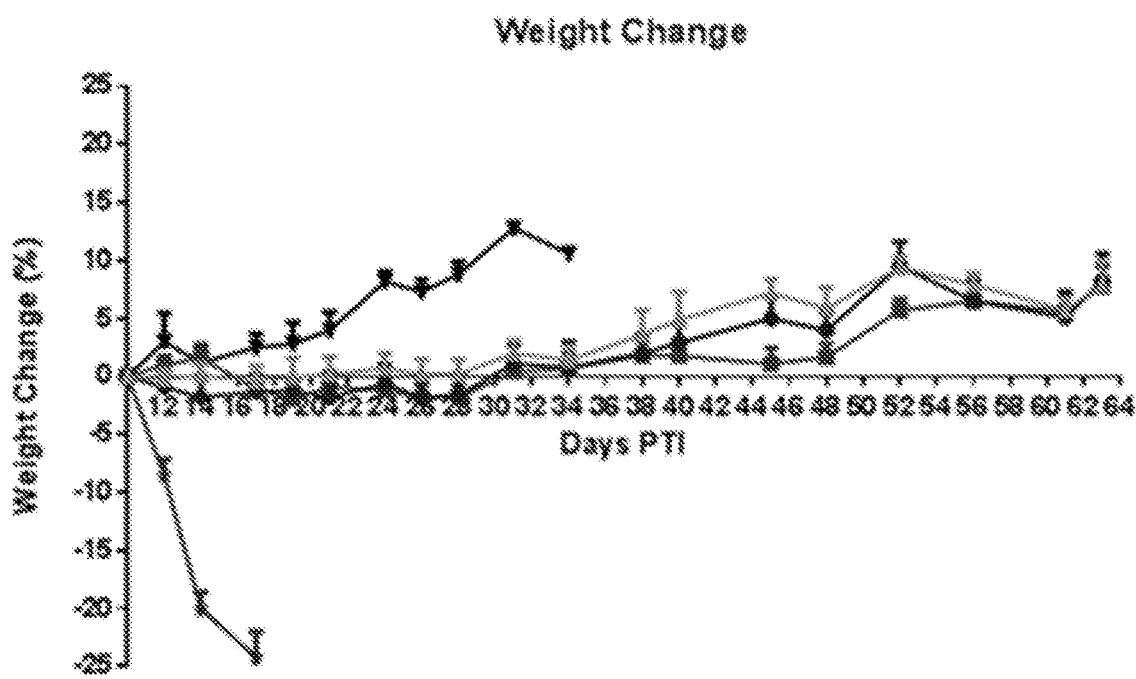
FIG. 8B shows % weight change after treatment with CA IX targeted conjugates (▼) Control; (▲) EC2711 {2,2,0}; (●) EC2763 {0,2,2}; (■) EC2766 {2,1,1}; (*) EC2761.
Figure 9A:
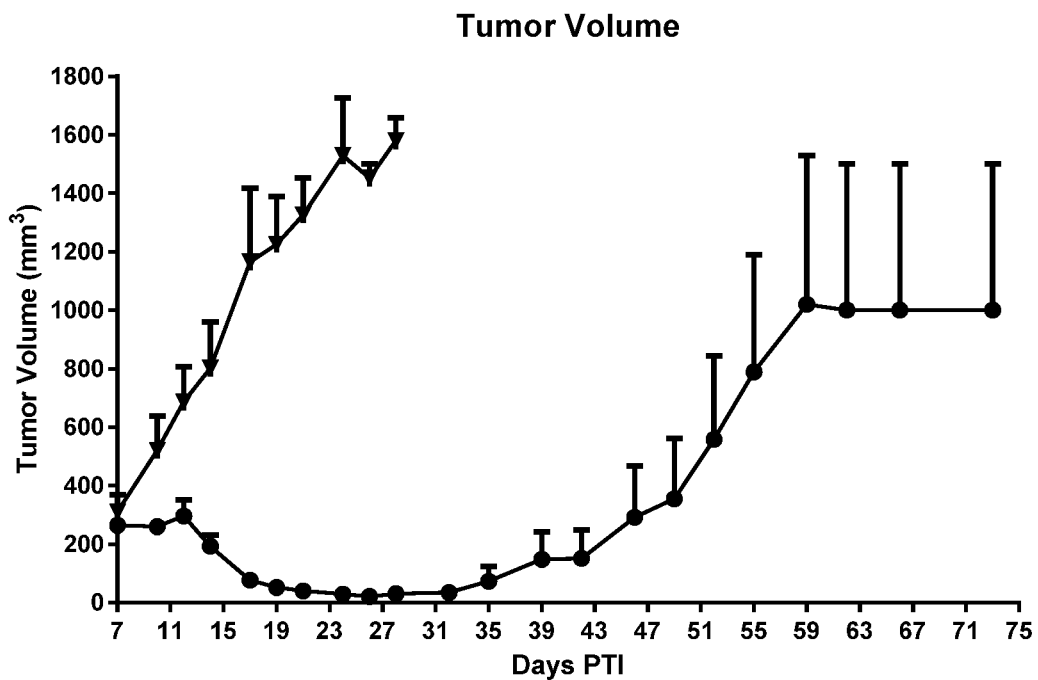
FIG. 9A shows tumor volumes after treatment with a CA IX targeted conjugate (▼) Control; (●) EC3157 {2,0,1}.
Figure 9B:
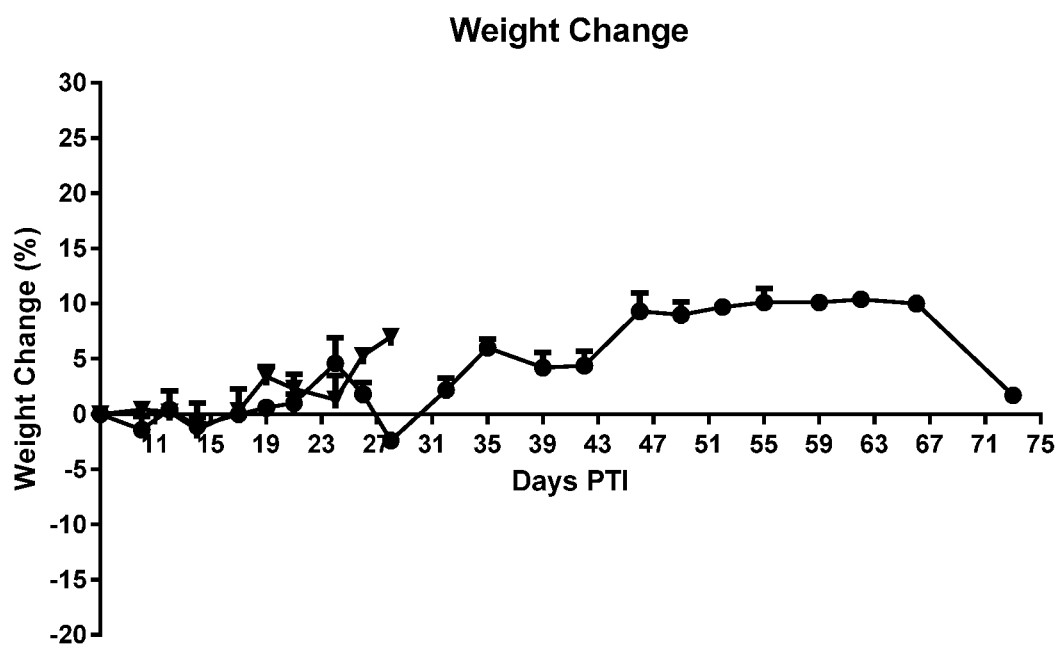
FIG. 9B shows % weight change after treatment with a CA IX targeted conjugate (▼) Control; (●) EC3157 {2,0,1}.

HT-29 cells were seeded in 8-well glass chamber slides in McCoy's 5A medium containing 10% FBS and were allowed to attach for 48 h in an incubator with an atmosphere of 5% $CO_2$/95% air and 37° C. Media was removed and replaced with fresh media containing final concentrations of 10 nM, 40 nM, 120 nM or 360 nM of the CAIX imaging conjugate (EC3114). Cells were incubated for 4 h in the presence of EC3114 at the aforementioned concentrations or 40 nM EC3114+100-fold (4 µM) excess acetazolamide ligand prior to removing the media and washing the each well 2× with FluoroBrite DMEM (ThermoFisher Scientific) to remove unbound conjugate. The chamber was removed from the glass slides and a drop of ProLong Diamond Antifade Mountant with DAPI (ThermoFisher Scientific) was applied to each well. Following the application of a glass coverslip, cells were visualized with a Leica DMLB microscope equipped with a mercury lamp to excite the imaging conjugate and a filter set to detect emission from the rhodamine dye. Representative images were acquired with a Leica DFC310 FX camera utilizing Leica Application Suite software, version 3.5.0, using either the 20× (FIG. 7A) or 40× objective (FIG. 7B). All images were identically post-edited with GIMP 2.8.18 software to optimize image clarity and brightness. Results are shown in FIGS. 7A and 7B.

In Vivo Experiments

Example 26: Conjugate Efficacy Studies

HT-29 cells were cultured in vitro in 6× T150 flasks in McCoys 5A medium supplemented with 10% BSA. Cells were trypsinized with 0.25% Trypsin/2.21 mM EDTA, resuspended in fresh medium, and counted with a hemocytometer. Approximately 8 million cells were implanted into the flank of nu/nu mice in a 100 ml volume, which were monitored every day with calipers to determine tumor volume. Once the tumors reached ~150-200 mm$^3$ in volume, the identified SMDCs were administered three times per week for two weeks at a dose of 2 mmoles/kg (or 2 mmoles/kg TIW×2) by intravenous injection via the tail vein. Tumor volume and animal weights were monitored throughout the course of the study, as indicated. Results are shown in FIGS. 8A and 8B, and FIGS. 9A and 9B.

What is claimed is:

1. A conjugate of the formula B-L-I, wherein B is a binding ligand of the formula

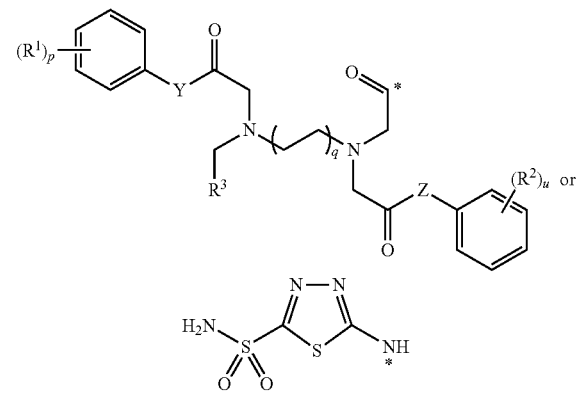

wherein
wherein each $R^1$ and $R^2$ is independently selected from the group consisting of H, $-OR^4$, $-OC(O)R^4$, $-OC(O)NR^4R^5$, $-OS(O)R^4$, $-OS(O)_2R^4$, $-SR^4$, $-S(O)R^4$, $-S(O)_2R^4$, $-S(O)NR^4R^5$, $-S(O)_2NR^4R^5$, $-OS(O)NR^4R^5$, $-OS(O)_2NR^4R^5$, $-NR^4R^5$, $-NR^4C(O)R^5$, $-NR^4C(O)OR^5$, $-NR^4C(O)NR^4'R^5'$, $-NR^4S(O)R^{5'}$, $-NR^4S(O)_2R^{5'}$, $-NR^4S(O)NR^{4'}R^{5'}$, $-NR^4S(O)_2NR^{4'}R^{5'}$, $-C(O)R^4$, $-C(O)OR^4$, and $-C(O)NR^4R^5$;

$R^3$ is selected from the group consisting of H, $C_1$-$C_6$ alkyl, $C_2$-$C_6$ alkenyl, and $C_2$-$C_6$ alkynyl, $-C(O)R^6$, $-C(O)OR^7$, and $-C(O)NR^7R^8$;

Y is $-O-$, $-CH_2-$ or $-NR^8-$;

Z is $-O-$, $-CH_2-$ or $-NR^9-$;

each $R^4$, $R^5$, $R^{4'}$, $R^{5'}$, $R^6$, $R^7$, $R^{7'}$, $R^8$ and $R^9$ is independently selected from the group consisting of H, $C_1$-$C_6$ alkyl, $C_2$-$C_6$ alkenyl, and $C_2$-$C_6$ alkynyl, or $R^6$ and $R^8$ taken together form a covalent bond from $R^3$ to Y to form a six-membered ring;

p is an integer from 1 to 4;

u is an integer from 0 to 4;

q is an integer from 1 to 3; and

* represents a covalent bond to the rest of the conjugate;

L is a linker comprising at least one amino acid, one or more spacer linkers ($L^2$), or a combination thereof, wherein $L^2$ is selected from the group consisting of C1-C6 alkyl, $-(CR^{39}R^{39'})_rOC(O)-$, $-C(O)O(CR^{39}R^{39'})_r-$, $-NR^{39}C(O)CR^{39}R^{39'})_r-$, $-(CH_2)_rNR^{39}-$, $-NR^{39}(CH_2)_r-$, $-NR^{39}(CH_2)_rNR^{39'}-$, $-(OCR^{39}R^{39'}CR^{39}R^{39'})_rC(O)-$, $-OCR^{39}R^{39'}CR^{39}R^{39'}CR^{39}R^{39'})_rC(O)-$, $-OC(O)(CR^{44}R^{44'})_r-$, $-C(O)(CR^{44}R^{44'})_r-$, $-NR^{42}CR^{43}R^{43'}CR^{43}R^{43'}(OCR^{44}R^{44'}CR^{44}R^{44'})_r-$, $-CR^{43}R^{43'}CR^{43}R^{43'}(OCR^{44}R^{44'}CR^{44}R^{44'})_rNR^{42}-$, —NR⁴²C₆-C₁₀ aryl(C₁-C₆ alkyl)OC(O)—, —C(O)CR⁴³R⁴³'CR⁴³R⁴³'(OCR⁴⁴R⁴⁴'CR⁴⁴R⁴⁴')NR⁴²—, and —NR⁴²CR⁴³R⁴³'CR⁴³R⁴³'(CR⁴⁴=CR⁴⁴')ₜ—;

wherein
each R³⁹ and R³⁹' is independently selected from the group consisting of H, halogen, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, 5- to 7-membered heteroaryl, —OC(O)R⁴⁰, —OC(O)NR⁴⁰R⁴⁰', —OS(O)R⁴⁰, —OS(O)₂R⁴⁰, —SR⁴⁰, —S(O)R⁴⁰, —S(O)₂R⁴⁰, —S(O)NR⁴⁰R⁴⁰', —S(O)₂NR⁴⁰R⁴⁰', —OS(O)NR⁴⁰R⁴⁰', —OS(O)₂NR⁴⁰R⁴⁰', —NR⁴⁰R⁴⁰', —NR⁴⁰C(O)R⁴¹, —NR⁴⁰C(O)OR⁴¹, —NR⁴⁰C(O)NR⁴¹R⁴¹', —NR⁴⁰S(O)R⁴¹, —NR⁴⁰S(O)₂R⁴¹, —NR⁴⁰S(O)NR⁴¹R⁴¹', —NR⁴⁰S(O)₂NR⁴¹R⁴¹', —C(O)R⁴⁰, —C(O)OR⁴⁰ and —C(O)NR⁴⁰R⁴⁰';

R⁴⁰, R⁴⁰', R⁴¹ and R⁴¹' are each independently selected from the group consisting of H, C₁-C₇ alkyl, C₂-C₇ alkenyl, C₂-C₇ alkynyl, C₃-C₆ cycloalkyl, 3- to 7-membered heterocycloalkyl, C₆-C₁₀ aryl, and 5- to 7-membered heteroaryl; and r in each instance is an integer from 1 to 40;

R⁴² is selected from the group consisting of H, C₁-C₆ alkyl, C₂-C₆ alkenyl, C₂-C₆ alkynyl and C₃-C₆ cycloalkyl, wherein each hydrogen atom in C₁-C₆ alkyl, C₂-C₆ alkenyl, C₂-C₆ alkynyl and C₃-C₆ cycloalkyl is independently optionally substituted by halogen, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, 5- to 7-membered heteroaryl, —OR⁴⁵, —OC(O)R⁴⁵, —OC(O)NR⁴⁵R⁴⁵', —OS(O)R⁴⁵, —OS(O)₂R⁴⁵, —SR⁴⁵, —S(O)R⁴⁵, —S(O)₂R⁴⁵, —S(O)NR⁴⁵R⁴⁵', —S(O)₂NR⁴⁵R⁴⁵', —OS(O)NR⁴⁵R⁴⁵', —OS(O)₂NR⁴⁵R⁴⁵', —NR⁴⁵R⁴⁵', —NR⁴⁵C(O)R⁴⁶, —NR⁴⁵C(O)OR⁴⁶, —NR⁴⁵C(O)NR⁴⁶R⁴⁶', —NR⁴⁵S(O)R⁴⁶, —NR⁴⁵S(O)₂R⁴⁶, —NR⁴⁵S(O)NR⁴⁶R⁴⁶', —NR⁴⁵S(O)₂NR⁴⁶R⁴⁶', —C(O)R⁴⁵, —C(O)OR⁴⁵ or —C(O)NR⁴⁵R⁴⁵', each R⁴³, R⁴³', R⁴⁴ and R⁴⁴' is independently selected from the group consisting of H, C₁-C₆ alkyl, C₂-C₆ alkenyl, C₂-C₆ alkynyl and C₃-C₆ cycloalkyl, wherein each hydrogen atom in C₁-C₆ alkyl, C₂-C₆ alkenyl, C₂-C₆ alkynyl and C₃-C₆ cycloalkyl is independently optionally substituted by halogen, C₁-C₆ alkyl, C₂-C₆ alkenyl, C₂-C₆ alkynyl, C₃-C₆ cycloalkyl, 3- to 7-membered heterocycloalkyl, C₆-C₁₀ aryl, 5- to 7-membered heteroaryl, —OC(O)R⁴⁷, —OC(O)NR⁴⁷R⁴⁷', —OS(O)R⁴⁷, —OS(O)₂R⁴⁷, —SR⁴⁷, —S(O)R⁴⁷, —S(O)₂R⁴⁷, —S(O)NR⁴⁷R⁴⁷', —S(O)₂NR⁴⁷R⁴⁷', —OS(O)NR⁴⁷R⁴⁷', —OS(O)₂NR⁴⁷R⁴⁷', —NR⁴⁷R⁴⁷', —NR⁴⁷C(O)R⁴⁸, —NR⁴⁷C(O)OR⁴⁸, —NR⁴⁷C(O)NR⁴⁸R⁴⁸', —NR⁴⁷S(O)R⁴⁸, —NR⁴⁷S(O)₂R⁴⁸, —NR⁴⁷S(O)NR⁴⁸R⁴⁸', —NR⁴⁷S(O)₂NR⁴⁸R⁴⁸', —C(O)R⁴⁷, —C(O)OR⁴⁷ or —C(O)NR⁴⁷R⁴⁷';

R⁴⁵, R⁴⁵', R⁴⁶, R⁴⁶', R⁴⁷, R⁴⁷', R⁴⁸ and R⁴⁸' are each independently selected from the group consisting of H, C₁-C₇ alkyl, C₂-C₇ alkenyl, C₂-C₇ alkynyl, C₃-C₆ cycloalkyl, 3- to 7-membered heterocycloalkyl, C₆-C₁₀ aryl and 5- to 7-membered heteroaryl;

t is in each instance an integer from 1 to 40; and
I is an imaging agent;

or a pharmaceutically acceptable salt thereof.

2. The conjugate of claim 1, or a pharmaceutically acceptable salt thereof, wherein B is of the formula

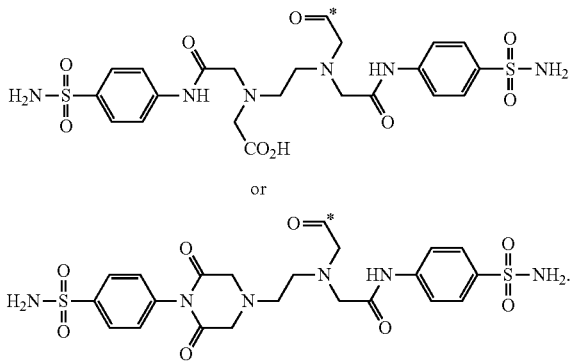

3. The conjugate of claim 1, selected from the group consisting of

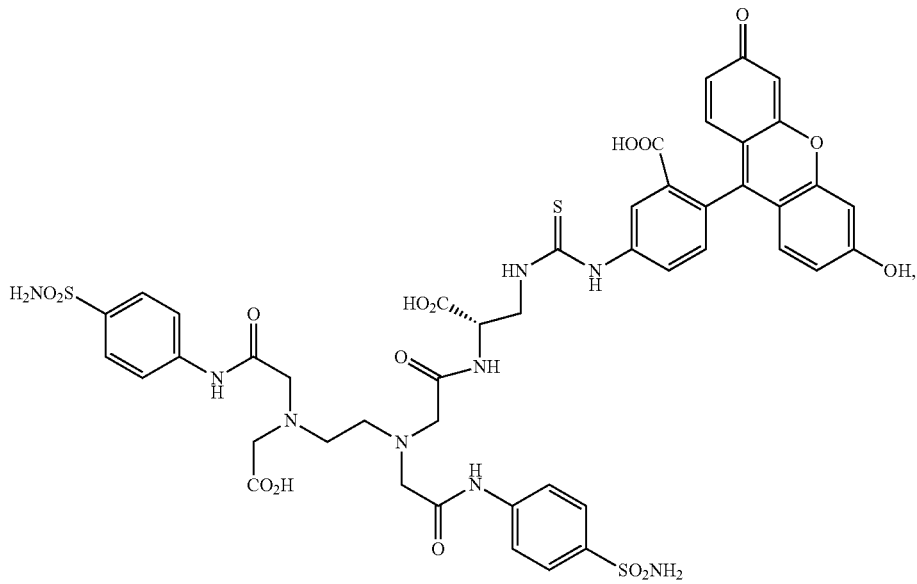

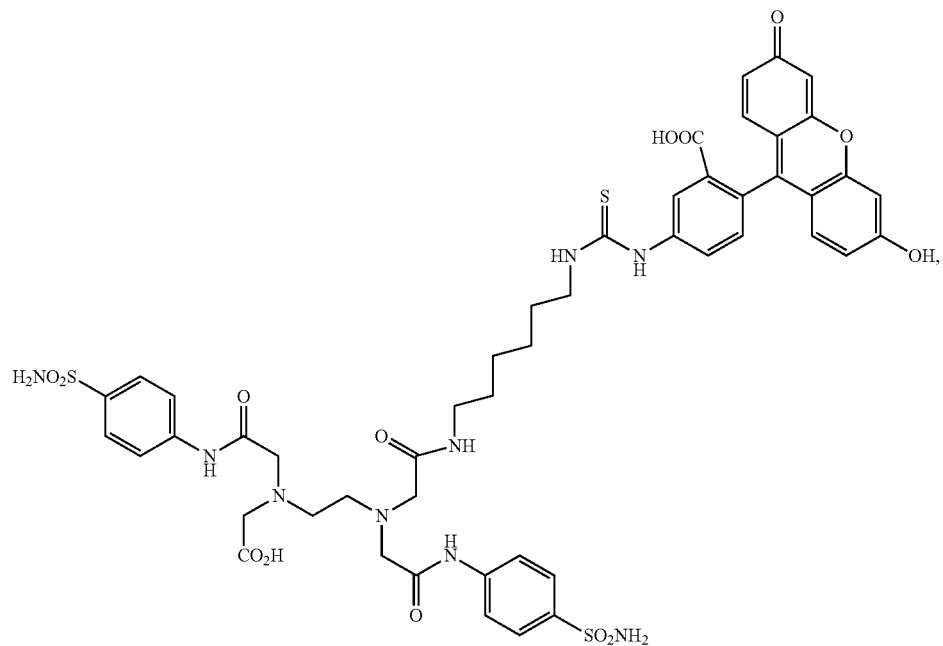
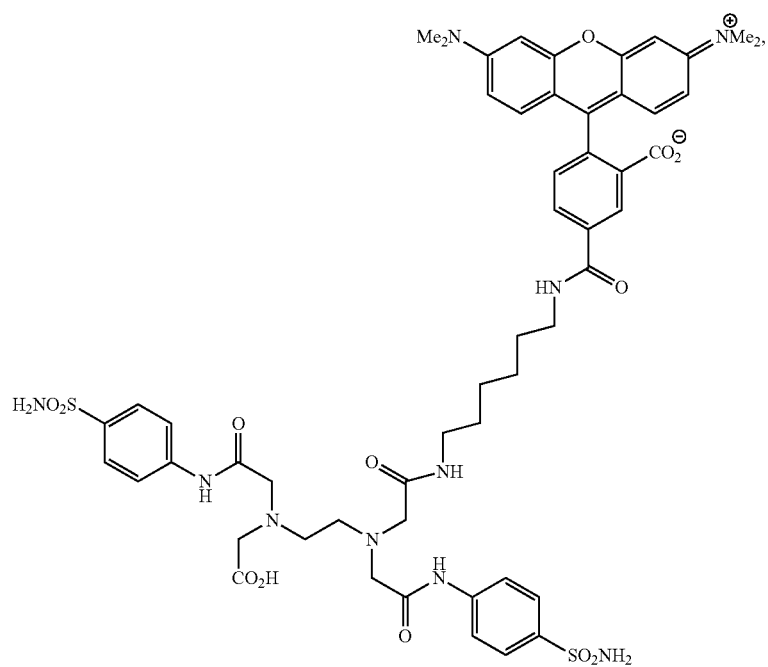

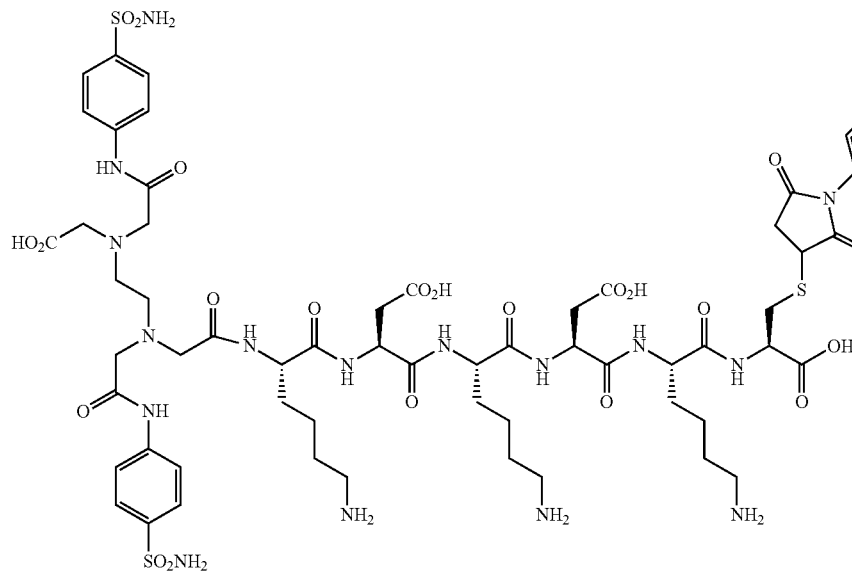

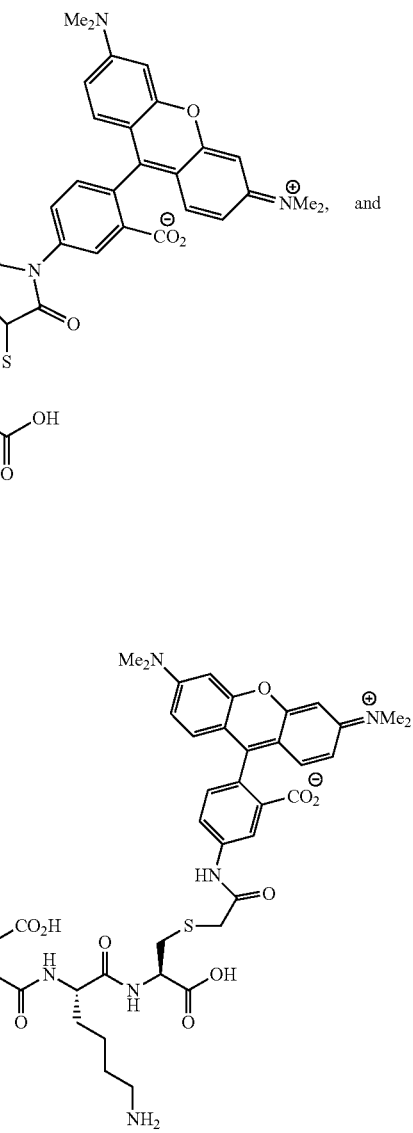

or a pharmaceutically acceptable salt thereof.

4. The conjugate of claim 1, or a pharmaceutically acceptable salt thereof, wherein p is 1.

5. The conjugate of claim 4, or a pharmaceutically acceptable salt thereof, wherein u is 1.

6. The conjugate of claim 1, or a pharmaceutically acceptable salt thereof, wherein q is 1.

7. The conjugate of claim 1, or a pharmaceutically acceptable salt thereof, wherein $R^1$ is —S(O)$_2$NR$^4$R$^5$.

8. The conjugate of claim 1, or a pharmaceutically acceptable salt thereof, wherein $R^2$ is —S(O)$_2$NR$^4$R$^5$.

9. The conjugate of claim 1, or a pharmaceutically acceptable salt thereof, wherein $R^3$ is —C(O)OR$^7$.

10. The conjugate of claim 1, or a pharmaceutically acceptable salt thereof, wherein Y is —NR$^8$—.

11. The conjugate of claim 1, or a pharmaceutically acceptable salt thereof, wherein Z is —NR$^9$—.

12. The conjugate of claim 1, or a pharmaceutically acceptable salt thereof, wherein $R^4$ is H.

13. The conjugate of claim 1, or a pharmaceutically acceptable salt thereof, wherein $R^5$ is H.

14. The conjugate of claim 1, or a pharmaceutically acceptable salt thereof, wherein $R^7$ is H.

15. The conjugate of claim 1, or a pharmaceutically acceptable salt thereof, wherein $R^8$ is H.

16. The conjugate of claim 1, or a pharmaceutically acceptable salt thereof, wherein $R^9$ is H.

17. The conjugate of claim 1, or a pharmaceutically acceptable salt thereof, wherein the linker comprises at least one amino acid.

18. The conjugate of claim 1, or a pharmaceutically acceptable salt thereof, wherein the imaging agent is selected from the group consisting of a dye, a PET imaging agent, and a radiolabeled agent.

19. The conjugate of claim 18, or a pharmaceutically acceptable salt thereof, wherein the imaging agent is a dye, and wherein the dye is a fluorescein dye.

20. The conjugate of claim 1, wherein $R^1$ is —S(O)$_2$NR$^4$R$^5$; $R^2$ is —S(O)$_2$NR$^4$R$^5$; $R^3$ is —C(O)OR$^7$; Y is —NR$^8$—; Z is —NR$^9$—; $R^4$ is H; $R^5$ is H; $R^7$ is H; $R^8$ is H; $R^9$ is H; p is 1; u is 1; and q is 1;
or a pharmaceutically acceptable salt thereof.

* * * * *